US005618720A

United States Patent [19]
Ellis et al.

[11] Patent Number: 5,618,720
[45] Date of Patent: *Apr. 8, 1997

[54] CELLS EXPRESSING CALCIUM CHANNEL α2 SUBUNIT-ENCODING DNA, OPTIONALLY WITH A REPORTER GENE FOR SCREENING ASSAYS

[75] Inventors: Steven B. Ellis, San Diego; Mark E. Williams, Carlsbad; Michael M. Harpold, San Diego, all of Calif.; Arnold Schwartz, Cincinnati, Ohio; Jean Sartor; Robert Brenner, both of San Diego, Calif.

[73] Assignee: Sibia Neurosciences, Inc., La Jolla, Calif.

[ * ] Notice: The term of this patent shall not extend beyond the expiration date of Pat. No. 5,407,820.

[21] Appl. No.: 404,354

[22] Filed: Feb. 15, 1995

Related U.S. Application Data

[60] Continuation of Ser. No. 314,083, Sep. 28, 1994, which is a division of Ser. No. 914,231, Jul. 13, 1992, Pat. No. 5,407,820, which is a continuation of Ser. No. 603,751, filed as PCT/US89/01408, Apr. 4, 1989, which is a continuation-in-part of Ser. No. 176,899, Apr. 4, 1988, abandoned.

[51] Int. Cl.$^6$ .............................. C12N 15/12; C12N 5/10; G01N 33/50
[52] U.S. Cl. .................. 435/325; 435/254.11; 435/7.21; 435/7.9; 435/8; 435/15
[58] Field of Search .......................... 435/240.2, 254.11, 435/69.1, 69.7, 7.21, 8, 15, 7–9; 536/23.5

[56] References Cited

U.S. PATENT DOCUMENTS

| | | | |
|---|---|---|---|
| 4,788,135 | 11/1988 | Davis et al. | 435/6 |
| 4,912,202 | 3/1990 | Campbell et al. | 530/388.22 |
| 4,950,739 | 8/1990 | Cherksey et al. | 530/350 |
| 4,954,436 | 9/1990 | Froehner et al. | 424/1.49 |
| 5,051,403 | 9/1991 | Miljanich et al. | 514/12 |
| 5,189,020 | 2/1993 | Mijanich et al. | 514/12 |
| 5,264,371 | 11/1993 | Miljanich et al. | 436/503 |
| 5,407,820 | 4/1995 | Ellis et al. | 435/240.2 |
| 5,424,218 | 6/1995 | Maljanich et al. | 436/503 |
| 5,436,128 | 7/1995 | Harpold et al. | 435/6 |

FOREIGN PATENT DOCUMENTS

| | | |
|---|---|---|
| 2085502 | 2/1993 | Canada. |
| 0507170 | 3/1992 | European Pat. Off.. |
| 9113077 | 9/1991 | WIPO. |
| 9202639 | 2/1992 | WIPO. |
| 9308469 | 4/1993 | WIPO. |
| 9314098 | 7/1993 | WIPO. |
| 9402511 | 2/1994 | WIPO. |

OTHER PUBLICATIONS

Blackshear et al., "Proteins kinase C–dependent and –independent pathways of protooncogene induction in human astrocytma cells," *J. Biol. Chem.* 262(16):7774–7781 (1987).

Boulter et al., "Functional expression of two neuronal nicotinic acetylcholine receptors from cDNA clones identifies a gene family," *Proc. Natl. Acad. Sci. USA* 84:7763–7767 (1987).

Ellis et al., "Replacement of insulin receptor tyrosine residues 1162 and 1163 compromises insulin–stimulated kinase activity and uptake of 2–deoxyglucose," *Cell* 45:721–732 (1986).

Green berg et al., "Stimulation of neuronal acetylcholine receptors induces rapid gene transcription," *Science* 234:80–83 (1986).

Peralta et al., "Distinct primary structures, ligand–binding properties and tissue–specific expression of four human muscarinic acetylcholine receptors," *EMBO J.* 6(13):3923–3929 (1987).

Stumpo et al., "Induction of c–fos sequences involved in induction by insulin and phorbol esters," *J. Biol. Chem.* 264(4):1611–1614 (1988).

Borsotto et al. (1985) "The 1,4–dihydropyridine receptor associated with the skeletal muscle voltage–dependent $Ca^{2+}$ channel," *J. Biol. Chem.*, 260(26): 14255–14263.

Claudio et al. (1987) "Genetic reconstitution of functional acetylcholine receptor channels in mouse fibroblasts," *Science*, 238: 1688–1694.

Claudio et al. (1987) "Stable expression of transfected *Torpedo* acetylcholine receptor α subunits in mouse fibroblast L cells," *Proc. Natl. Acad. Sci.*, 84:5967–5971.

Cooper et al. (1987) "Purification and characterization of the dihydropyridine–sensitive voltage–dependent calcium channel from cardiac tissue," *J. Biol. Chem.*, 262(2): 509–512.

Dascal et al. (1986) Expression of modulation of voltage–gated calcium channels after RNA injection in *Xenopus* oocytes, *Science*, 231: 1147–1150.

Leung et al. (1988) "Monoclonal antibody characterization of the 1,4–dihydropyridine receptor of rabbit skeletal muscle," *Ann. N.Y. Acad. Sci.*, 522: 43–46.

Nakayama et al. (1987) "Purification of a putative $Ca^{2+}$ channel protein from rabbit skeletal muscle," *J. Biol. Chem.*, 262: 6572–6576.

(List continued on next page.)

*Primary Examiner*—David L. Fitzgerald
*Attorney, Agent, or Firm*—Stephanie L. Seidman; Brown, Martin, Haller & McClain

[57] ABSTRACT

[DNAs] DNA molecules encoding mammalian calcium channel $a_1$ and $a_2$ subunits are provided. The [DNAs] DNA molecules are used to transform host cells which may also contain a reporter gene, the transcription of which is responsive to an ion or molecule capable of entering the cell through a calcium channel.

5 Claims, 25 Drawing Sheets

OTHER PUBLICATIONS

Leung, et al. "Structural characterization of the 1,4–dihydropyridine receptor of the voltage–dependent $Ca^{2+}$ channel from rabbit skeletal muscle," *J. Biol. Chem.*, 262(17): 7943–7946 (1987).

Curtis et al. (1984) "Purification of the calcium antagonist receptor of the voltage–sensitive calcium channel from skeletal muscle transverse tubules," *Biochemistry*, 23(10): 2113–2118.

Schmid et al. (1986), "Immunochemical analysis of subunit structure of 1,4–dihydropyridine receptors associated with voltage–dependent $Ca^{2+}$ channels in skeletal, cardiac, and smooth muscles," *Biochemistry*, 25: 3492–3495.

Seager, et al., *Ann. N.Y. Acad. Sci.* 522:43–46 (1988).

Takahashi et al. (1987) "Dihydropyridine–sensitive calcium channels in cardiac and skeletal muscle membranes: studies with antibodies against the α–subunits," *Biochemistry*, 26(17): 1518–1526.

Vaghy et al. (1988) "Mechanism of action of calcium channel modulator drugs," *Ann. N.Y. Acad. Sci.*, 522: 176–186.

Wood (1987) Wood, "Gene cloning based on long oligonucleotide probes," *Methods in Enzymology*, 152: 443–447.

Brust et al., "Human Neuronal Voltage–Dependent Calcium Channels: Studies on Subunit Structure and Role in Channel Assembly", *Neuropharmacology* 32(11):1089–1102 (1993).

Williams, et al., "Structure and functional expression of $\alpha_1$, $\alpha_2$ and β subunits of a novel human neuronal calcium channel subtype," *Neuron*, 8:71–84 (1992).

Williams et al., "Structure and Functional Expression of an ω–Conotoxin–Sensitive Human N–Type Calcium Channel", *Science* 257:389–395 (1992).

Williams et al., "Structure and Functional Characterization of Neuronal $\alpha_{1E}$ Calcium Channel Subtypes," *J. Biol. Chem.* 269(35):22347–22357 (1994).

Leung, et al., "Biochemical and ultrastructural characterization of the 1,4–dihydropyridine receptor from rabbit skeletal muscle," *J. Biol. Chem.* 263(2):994–1101 (1988).

Imagawa, et al., "Phosphorylation of the 1,4–dihydropyridine receptor of the voltage–dependent $Ca^{2+}$ channel by an intrinsic protein kinase in isolated triads from rabbit skeletal muscle," *J. Biol. Chem.* 262(17):8333–8339 (1987).

Miller, "Multiple calcium channels and neuronal function," *Science* 234:46–52 (1987)Miller (1987) Multiple calcium channels and neuronal function, *Science*, 235: 46–52.

Kozak, "An analysis of 5'–noncoding sequences from 699 vertebrate messenger RNAs," *Nucleic Acids Research* 15(20):8125–8148 (1987).

von Heijne, "Signal sequences: the limits of variation," *J. Mol. Biol.* 184:99–105 (1985).

Hubbard, et al., "Synthesis and processing of asparagine–linked oligosacchardes[1,2]," *Ann. Rev. Biochem.* 50:555–583 (1981).

Faramisco, et al., "Optimal spatial requirements for the location of basic residues in peptide substrates for the cyclic AMP–dependent protein kinase," *J. Biol. Chem.* 225(9):4240–4245 (1980).

Takahashi & Catterall, "Identification of an α subunit of dihydropyridine–sensitive brain calcium channels," *Science* 236:88–91 (1987).

Hofmann, et al., "Regulation of the L–type calcium channel," *TIPS* 8:393–398 (1987).

Curtis, et al., "Reconstitution of the voltage–sensitive calcium channel purified from skeletal muscle transverse tubules," *Biochemistry* 25:3077–3083 (1986).

Smith, et al., "Calcium channel activity in a purified dihydropyridine–receptor preparation of skeletal muscle," *Biochemistry* 26:7182–7188 (1987).

Ellis, et al, "Sequence and expression of mRNAs encoding the $\alpha_1$ and $\alpha_2$ subunits of DHP–sensitive calcium channel," *Science* 241:1661–1664 (1988).

Vaghy, et al., "Identification of a Novel 1,4–Dihydropyridine–and Phenylalkylamine–binding Polypeptide in Calcium Channel Preparations," *J. Biol. Chem.* 262:14337–14342 (1987).

Meshi, et al., "Nucleotide sequence of the 30K protein cistron of cowpea strain of tobacco mosaic virus," *Nucleic Acids Research* 10:6111–6117 (1982).

Nikaido, et al., "Molecular cloning of cDNA encoding human interleukin–2 receptor," *Nature* 311:631–636 (1984).

Noda, et al., "Existence of distinct sodium channel messenger RNAs in rat brain," *Nature* 320:188–192 (1986).

Noda, et al., "Expression of functional sodium channels from cloned cDNA," *Nature* 322:826–828 (1986).

Mierendorf, et al., "Gene Isolation by Screening γgt11 Libraries with Antibodies," *Methods in Enzymology* 152:458–469 (1986).

Gustin, et al., "Ion Channels in Yeast," *Science* 233:1195–1197 (1986).

Striessnig, et al., "Photoaffinity labelling of the phenylalkylamine receptor of the skeletal muscle transverse–tubule calcium channel," *FEBS Letters* 212:247–253 (1987).

Curran and Morgan, "Barium Modulates c–fos Expression and Post–Translational Modification," *Proc. Natl. Acad. Sci. USA* 83:8521–8524 (1986).

Fisch, et al., "c–fos Sequences Necessary for Basal Expression and Induction by Epidermal Growth Factor, 12–O–Tetradecanoyl Phorbol–13–Acetate, and the Calcium Ionophore," *Mol. Cell. Biol.* 7:3490–3502 (1987).

Barhanin, et al., "The Calcium Channel Antagonists Receptor from Rabbit Skeletal Muscle: Reconstitution after Purification and Subunit Characterization" *Eur. J. Biochem.* 164:525–531 (1987).

Sieber, et al., "The 165–KDa Peptide of the Purified Skeletal Muscle Dihydropyridine REceptor Contains the Known Regulatory Sites of the Calcium Channel," *Eur. J. Biochem.* 167:117–122 (1987).

Lang, et al., "The Effect of Myasthenic Syndrome Antibody on Presynaptic Channels in the Mouse," *J. Physiol.* 390:257–270 (1987).

Catterall, et al., "Molecular Properties of Dihydropyridine–sensitive Calcium Channels in Skeletal Muscle," *J. Biol. Chem.* 263:3535–3538 (1988).

Takahashi and Catterall, "Dihydropyridine–sensitive Calcium Channels in Cardiac and Skeletal Muscle Membranes: Studies with Antibodies against the Alpha Subunits," *Biochemistry* 26:5518–5526 (1987).

Morton and Froehner, "Monoclonal Antibody Identifies a 200–kDA Subunit of the Dihydropyridine–sensitive Calcium Channel," *J. Biol. Chem.* 262:11904–11907 (1987).

Sharp, et al, "Identification and Characterization of the Dihydropyridine–binding Subunit of the Skeletal Muscle Dihydropyridine Receptor," *J. Biol. Chem.* 62:12309–12315 (1987).

Takahashi, et al., "Subunit Structure of Dihydropyridine–sensitive Calcium Channels from Skeletal Muscle," *Proc. Natl. Acad. Sci. USA* 84:5478–5482 (1987).

Tanabe, et al., "Primary Structure of the Receptor for Calcium Channel Blockers from Skeletal Muscle," *Nature* 328:313–318 (1987).

Nakayama, et al., "Purification of a Putative $Ca^{+2}$ Channel Protein from Rabbit Skeletal Muscle," *J. Biol. Chem.* 262:6572–6576 (1987).

Williams et al., "Structure and Functional Expression of an ω–Contoxin–Sensitive Human N–Type Calcium Channel", *Science* 257:389–395 (1992).

Williams, et al., "Structure and functional characterization of neuronal $\alpha_{1E}$ calcium channel subtypes," *J. Biol. Chem.* 269(35):22347–22357 (1994).

Brust, et al., "Human Neuronal Voltage–Dependent Calcium Channels: Studies on Subunit Structure and Role in Channel Assembly", *Neuropharmacology* 32(11):1089–1102 (1993).

FIGURE 1a

```
                                              GCGGGGAA CACTGGGGAC-61
GCAGGGAAGA GAGGGCCGCG GGGTGGGGGA GCAGCAGGAA GCGCCGTGGC CAGGGAAGCC-1
```

| | | | | | | | | | | | | | | | | |
|---|---|---|---|---|---|---|---|---|---|---|---|---|---|---|---|---|
| ATG | GAG | CCA | TCC | TCA | CCC | CAG | GAT | GAG | GGC | CTG | AGG | AAG | AAA | CAG | CCC | 48 |
| MET | GLU | PRO | SER | SER | PRO | GLN | ASP | GLU | GLY | LEU | ARG | LYS | LYS | GLN | PRO | |
| | | | | 5 | | | | 10 | | | | | 15 | | | |

| AAG | AAG | CCC | CTG | CCC | GAG | GTC | CTG | CCC | AGG | CCG | CCG | CGG | GCT | CTG | TTC | 96 |
|---|---|---|---|---|---|---|---|---|---|---|---|---|---|---|---|---|
| LYS | LYS | PRO | LEU | PRO | GLU | VAL | LEU | PRO | ARG | PRO | PRO | ARG | ALA | LEU | PHE | |
| | | | 20 | | | | | 25 | | | | | 30 | | | |

| TGC | CTG | ACC | CTG | CAG | AAC | CCG | CTG | AGG | AAG | GCG | TGC | ATC | AGC | ATC | GTG | 144 |
|---|---|---|---|---|---|---|---|---|---|---|---|---|---|---|---|---|
| CYS | LEU | THR | LEU | GLN | ASN | PRO | LEU | ARG | LYS | ALA | CYS | ILE | SER | ILE | VAL | |
| 35 | | | | | 40 | | | | | 45 | | | | | | |

| GAA | TGG | AAA | CCC | TTC | GAG | ACC | ATC | ATC | CTG | CTC | ACC | ATC | TTT | GCC | AAC | 192 |
|---|---|---|---|---|---|---|---|---|---|---|---|---|---|---|---|---|
| GLU | TRP | LYS | PRO | PHE | GLU | THR | ILE | ILE | LEU | LEU | THR | ILE | PHE | ALA | ASN | |
| | 50 | | | | | 55 | | | | | 60 | | | | | |

| TGT | GTG | GCC | CTG | GCC | GTG | TAC | CTG | CCC | ATG | CCC | GAG | GAT | GAC | AAC | AAC | 240 |
|---|---|---|---|---|---|---|---|---|---|---|---|---|---|---|---|---|
| CYS | VAL | ALA | LEU | ALA | VAL | TYR | LEU | PRO | MET | PRO | GLU | ASP | ASP | ASN | ASN | |
| 65 | | | | | 70 | | | | | 75 | | | | * | 80 | |

| TCC | CTG | AAC | CTG | GGC | CTG | GAG | AAG | CTG | GAG | TAC | TTC | TTC | CTC | ACC | GTC | 288 |
|---|---|---|---|---|---|---|---|---|---|---|---|---|---|---|---|---|
| SER | LEU | ASN | LEU | GLY | LEU | GLU | LYS | LEU | GLU | TYR | PHE | PHE | LEU | THR | VAL | |
| | | | | 85 | | | | | 90 | | | | | 95 | | |

| TTC | TCC | ATC | GAA | GCC | GCC | ATG | AAG | ATC | ATC | GCC | TAC | GGC | TTC | CTG | TTC | 336 |
|---|---|---|---|---|---|---|---|---|---|---|---|---|---|---|---|---|
| PHE | SER | ILE | GLU | ALA | ALA | MET | LYS | ILE | ILE | ALA | TYR | GLY | PHE | LEU | PHE | |
| | | | 100 | | | | | 105 | | | | | 110 | | | |

| CAC | CAG | GAC | GCC | TAC | CTG | CGC | AGC | GGC | TGG | AAC | GTG | CTG | GAC | TTC | ATC | 384 |
|---|---|---|---|---|---|---|---|---|---|---|---|---|---|---|---|---|
| HIS | GLN | ASP | ALA | TYR | LEU | ARG | SER | GLY | TRP | ASN | VAL | LEU | ASP | PHE | ILE | |
| | | 115 | | | | | 120 | | | | | 125 | | | | |

| ATC | GTC | TTC | CTG | GGG | GTC | TTC | ACG | GCG | ATT | CTG | GAA | CAG | GTC | AAC | GTC | 432 |
|---|---|---|---|---|---|---|---|---|---|---|---|---|---|---|---|---|
| ILE | VAL | PHE | LEU | GLY | VAL | PHE | THR | ALA | ILE | LEU | GLU | GLN | VAL | ASN | VAL | |
| | | 130 | | | | | 135 | | | | | 140 | | | | |

| ATC | CAG | AGC | AAC | ACG | GCC | CCG | ATG | AGC | AGC | AAA | GGA | GCC | GGC | CTG | GAC | 480 |
|---|---|---|---|---|---|---|---|---|---|---|---|---|---|---|---|---|
| ILE | GLN | SER | ASN | THR | ALA | PRO | MET | SER | SER | LYS | GLY | ALA | GLY | LEU | ASP | |
| 145 | | | | | 150 | | | | | 155 | | | | | 160 | |

| GTC | AAG | GCC | CTG | AGG | GCC | TTC | CGT | GTG | CTC | AGA | CCC | CTC | CGG | CTG | GTG | 528 |
|---|---|---|---|---|---|---|---|---|---|---|---|---|---|---|---|---|
| VAL | LYS | ALA | LEU | ARG | ALA | PHE | ARG | VAL | LEU | ARG | PRO | LEU | ARG | LEU | VAL | |
| | | | 165 | | | | | 170 | | | | | 175 | | | |

FIGURE 1b

```
TCG GGG GTG|CCT AGT TTG CAG GTG GTC CTC AAC TCC ATC TTC AAG GCC   576
SER GLY VAL|PRO SER LEU GLN VAL VAL LEU ASN SER ILE PHE LYS ALA
    180         185                         190

ATG CTC CCC CTG TTC CAC|ATC GCC CTG CTC GTC CTC TTC ATG GTC ATC   624
MET LEU PRO LEU PHE HIS|ILE ALA LEU LEU VAL LEU PHE MET VAL ILE
        195                 200                 205

ATC TAC GCC ATC ATC GGG CTG GAG CTC TTC|AAG GGC AAG ATG CAC AAG   672
ILE TYR ALA ILE ILE GLY LEU GLU LEU PHE|LYS GLY LYS MET HIS LYS
        210             215                 220

ACC TGC TAC TAC ATC GGG ACA GAC ATC GTG GCC ACA GTG GAG AAT GAG   720
THR CYS TYR TYR ILE GLY THR ASP ILE VAL ALA THR VAL GLU ASN GLU
225                 230                 235                 240

AAG CCC TCG CCC TGC GCT AGG ACG GGC TCG GGG CGC CCC TGC ACC ATC   768
LYS PRO SER PRO CYS ALA ARG THR GLY SER GLY ARG PRO CYS THR ILE
            245                 250                 255

AAC GGC AGC GAG TGC CGG GGC GGC TGG CCG GGG CCC AAC CAC GGC ATC   816
ASN GLY SER GLU CYS ARG GLY GLY TRP PRO GLY PRO ASN HIS GLY ILE
 *          260                 265                 270

ACG CAC TTC GAC AAC TTC GGC TTC TCC ATG CTC ACC GTG TAC CAG TGC   864
THR HIS PHE ASP ASN PHE GLY PHE SER MET LEU THR VAL TYR GLN CYS
            275                 280                 285

ATC ACC ATG GAG GGC TGG ACA GAT GTC CTC TAC TGG GTC AAC GAT GCC   912
ILE THR MET GLU GLY TRP THR ASP VAL LEU TYR TRP VAL ASN ASP ALA
            290                 295                 300

ATC GGG AAC GAG TGG|CCC TGG ATC TAC TTT GTC ACT CTC ATC CTG CTG   960
ILE GLY ASN GLU TRP|PRO TRP ILE TYR PHE VAL THR LEU ILE LEU LEU
305                 310                 315                 320

GGG TCC TTC TTC ATC CTC AAC CTG GTG CTG GGC GTC CTG AGT|GGG GAA  1008
GLY SER PHE PHE ILE LEU ASN LEU VAL LEU GLY VAL LEU SER|GLY GLU
            325                 330                 335

TTC ACC AAG GAG CGG GAG AAG GCC AAG TCC AGG GGA ACC TTC CAG AAG  1056
PHE THR LYS GLU ARG GLU LYS ALA LYS SER ARG GLY THR PHE GLN LYS
            340                 345                 350

CTG CGG GAG AAG CAG CAG CTG GAG GAG GAC CTT CGG GGC TAC ATG AGC  1104
LEU ARG GLU LYS GLN GLN LEU GLU GLU ASP LEU ARG GLY TYR MET SER
            355                 360                 365
```

FIGURE 1c

```
TGG ATC ACG CAG GGC GAG GTC ATG GAC GTG GAG GAC CTG AGA GAA GGA 1152
TRP ILE THR GLN GLY GLU VAL MET ASP VAL GLU ASP LEU ARG GLU GLY
    370             375             380

AAG CTG TCC TTG GAA GAG GGA GGC TCC GAC ACG GAA AGC CTG TAC GAA 1200
LYS LEU SER LEU GLU GLU GLY GLY SER ASP THR GLU SER LEU TYR GLU
385             390             395             400

ATC GAG GGC TTG AAC AAA ATC ATC CAG TTC ATC CGA CAC TGG AGG CAG 1248
ILE GLU GLY LEU ASN LYS ILE ILE GLN PHE ILE ARG HIS TRP ARG GLN
                405             410             415

TGG AAC CGT GTC TTT CGC TGG AAG TGC CAT GAC CTG GTG AAG TCG AGA 1296
TRP ASN ARG VAL PHE ARG TRP LYS CYS HIS ASP LEU VAL LYS SER ARG
            420             425             430

GTC TTC TAC TGG CTG GTC ATC CTG ATC GTG GCC CTC AAC ACC CTG TCC 1344
VAL PHE TYR TRP LEU VAL ILE LEU ILE VAL ALA LEU ASN THR LEU SER
        435             440             445

ATC GCC TCG GAG CAC CAC AAC CAG CCG CTC TGG CTG ACC CAC TTG CAA 1392
ILE ALA SER GLU HIS HIS ASN GLN PRO LEU TRP LEU THR HIS LEU GLN
        450             455             460

GAC ATC GCC AAT CGA GTG CTG CTG TCA CTC TTC ACC ATC GAG ATG CTG 1440
ASP ILE ALA ASN ARG VAL LEU LEU SER LEU PHE THR ILE GLU MET LEU
465             470             475             480

CTG AAG ATG TAC GGG CTG GGC CTG CGC CAG TAC TTC ATG TCC ATC TTC 1488
LEU LYS MET TYR GLY LEU GLY LEU ARG GLN TYR PHE MET SER ILE PHE
                485             490             495

AAC CGC TTC GAC TGC TTC GTG GTG TGC AGC GGC ATC CTG GAG CTG CTG 1536
ASN ARG PHE ASP CYS PHE VAL VAL CYS SER GLY ILE LEU GLU LEU LEU
            500             505             510

CTG GTG GAG TCG GGC GCC ATG ACG CCG CTG GGC ATC TCC GTG TTG CGC 1584
LEU VAL GLU SER GLY ALA MET THR PRO LEU GLY ILE SER VAL LEU ARG
            515             520             525

TGC ATC CGC CTC CTG AGG CTC TTC AAG ATC ACC AAG TAC TGG ACG TCG 1632
CYS ILE ARG LEU LEU ARG LEU PHE LYS ILE THR LYS TYR TRP THR SER
        530             535             540
```

FIGURE 1d

```
CTC AGC AAC CTG GTG GCC TCC CTG CTC AAC TCC ATC CGC TCC ATC GCC 1680
LEU SER ASN LEU VAL ALA SER LEU LEU ASN SER ILE ARG SER ILE ALA
545                 550                 555                 560

TCG|CTG CTG CTG CTG CTC TTC CTC TTC ATC ATC ATC TTC GCC CTG CTG 1728
SER|LEU LEU LEU LEU LEU PHE LEU PHE ILE ILE ILE PHE ALA LEU LEU
            565                 570                 575

GGC ATG CAG CTC TTC|GGG GGG CGG TAC GAC TTC GAG GAC ACG GAA GTG 1766
GLY MET GLN LEU PHE|GLY GLY ARG TYR ASP PHE GLU ASP THR GLU VAL
            580                 585                 590

CGA CGC AGC AAC TTC GAC AAC TTC CCC CAG GCC CTC ATC AGC GTC TTC 1824
ARG ARG SER ASN PHE ASP ASN PHE PRO GLN ALA LEU ILE SER VAL PHE
            595                 600                 605

CAG GTG CTG ACG GGT GAG GAC TGG AAC TCC GTG ATG TAC AAC GGG ATC 1872
GLN VAL LEU THR GLY GLU ASP TRP ASN SER VAL MET TYR ASN GLY ILE
        610                 615                 620

ATG GCC TAC GGA GGC CCG TCC TAC CCG GGC GTT CTC|GTG TGC ATC TAT 1920
MET ALA TYR GLY GLY PRO SER TYR PRO GLY VAL LEU|VAL CYS ILE TYR
625                 630                 635                 640

TTC ATC ATC CTT TTT GTC TGC GGC AAC TAT ATC CTG CTG AAT GTC TTC 1968
PHE ILE ILE LEU PHE VAL CYS GLY ASN TYR ILE LEU LEU ASN VAL PHE
                645                 650                 655

CTG GCC ATC GCC GTG|GAC AAC CTG GCC GAG GCC GAG AGC CTG ACT TCC 2016
LEU ALA ILE ALA VAL|ASP ASN LEU ALA GLU ALA GLU SER LEU THR SER
            660                 665                 670

GCG CAA AAG GCC AAG GCC GAG GAG AGG AAA CGT AGG AAG ATG TCC AGG 2064
ALA GLN LYS ALA LYS ALA GLU GLU ARG LYS ARG ARG LYS MET SER ARG
            675                 680                 685     P

GGT CTC CCT GAC AAG ACG GAG GAG GAG AAG TCT GTG ATG GCC AAG AAG 2112
GLY LEU PRO ASP LYS THR GLU GLU GLU LYS SER VAL MET ALA LYS LYS
        690                 695                 700

CTG GAG CAG AAG CCC AAG GGG GAG GGC ATC CCC ACC ACT GCC AAG CTC 2160
LEU GLU GLN LYS PRO LYS GLY GLU GLY ILE PRO THR THR ALA LYS LEU
705                 710                 715                 720

AAG GTC GAT GAG TTC GAA TCT AAC GTC AAC GAG GTG AAG GAC CCC TAC 2208
LYS VAL ASP GLU PHE GLU SER ASN VAL ASN GLU VAL LYS ASP PRO TYR
            725                 730                 735
```

FIGURE 1e

```
CCT TCA GCT GAC TTC CCA GGG GAT GAT GAG GAG GAC GAG CCT GAG ATC 2256
PRO SER ALA ASP PHE PRO GLY ASP ASP GLU GLU ASP GLU PRO GLU ILE
        740                 745                 750

CCA GTG AGC CCC CGA CCG CGC CCG CTG GCC GAG CTG CAG CTC AAA GAG 2304
PRO VAL SER PRO ARG PRO ARG PRO LEU ALA GLU LEU GLN LEU LYS GLU
        755                 760                 765

AAG GCA GTG CCC ATC CCG GAA GCC AGC TCC TTC TTC ATC TTC AGT CCC 2352
LYS ALA VAL PRO ILE PRO GLU ALA SER SER PHE PHE ILE PHE SER PRO
        770                 775                 780

ACC AAT AAG GTC CGT GTC CTG TGT CAC CGC ATC GTC AAC GCC ACC TGG 2400
THR ASN LYS VAL ARG VAL LEU CYS HIS ARG ILE VAL ASN ALA THR TRP
785                 790                 795      *          800

TTC ACC AAC TTC ATC CTG CTC TTC ATC CTG CTC AGC AGT GCT GCG CTG 2448
PHE THR ASN PHE ILE LEU LEU PHE ILE LEU LEU SER SER ALA ALA LEU
                805                 810                 815

GCC GCC GAG GAC CCC ATC CGG GCG GAG TCC GTG AGG AAT CAG ATC CTT 2496
ALA ALA GLU ASP PRO ILE ARG ALA GLU SER VAL ARG ASN GLN ILE LEU
        820                 825                 830

GGA TAT TTT GAT ATT GCC TTC ACC TCT GTC TTC ACT GTG GAG ATT GTC 2544
GLY TYR PHE ASP ILE ALA PHE THR SER VAL PHE THR VAL GLU ILE VAL
        835                 840                 845

CTC AAG ATG ACA ACC TAC GGC GCC TTC CTG CAC AAG GGC TCC TTC TGC 2592
LEU LYS MET THR THR TYR GLY ALA PHE LEU HIS LYS GLY SER PHE CYS
        850                 855                 860

CGC AAC TAC TTC AAC ATC CTG GAC CTG CTG GTG GTG GCC GTG TCT CTC 2640
ARG ASN TYR PHE ASN ILE LEU ASP LEU LEU VAL VAL ALA VAL SER LEU
865             870                 875                 880

ATC TCC ATG GGT CTC GAG TCC AGC ACC ATC TCC GTG GTA AAG ATC CTG 2688
ILE SER MET GLY LEU GLU SER SER THR ILE SER VAL VAL LYS ILE LEU
                885                 890                 895

AGA GTG CTA AGG GTG CTC CGG CCC CTG CGA GCC ATC AAC AGA GCC AAA 2736
ARG VAL LEU ARG VAL LEU ARG PRO LEU ARG ALA ILE ASN ARG ALA LYS
        900                 905                 910
```

FIGURE 1f

```
GGG TTG AAG CAC GTG GTC CAG TGC GTG TTC GTG GCC ATC CGC ACC ATC  2784
GLY LEU LYS HIS VAL VAL GLN CYS VAL PHE VAL ALA ILE ARG THR ILE
        915                 920                 925

GGG AAC|ATC GTC CTG GTC ACC ACG CTC CTG CAG TTC ATG TTC GCC TGC  2832
GLY ASN|ILE VAL LEU VAL THR THR LEU LEU GLN PHE MET PHE ALA CYS
    930                 935                 940

ATC GGT GTC CAG CTC TTC|AAG GGC AAG TTC TTC AGC TGC AAT GAC CTA  2880
ILE GLY VAL GLN LEU PHE|LYS GLY LYS PHE PHE SER CYS ASN ASP LEU
945             950                 955                 960

TCC AAG ATG ACA GAA GAG GAG TGC AGG GGC TAC TAC TAT GTG TAC AAG  2928
SER LYS MET THR GLU GLU GLU CYS ARG GLY TYR TYR TYR VAL TYR LYS
            965                 970                 975

GAC GGG GAC CCC ACG CAG ATG GAG CTG CGC CCC CGC CAG TGG ATA CAC  2976
ASP GLY ASP PRO THR GLN MET GLU LEU ARG PRO ARG GLN TRP ILE HIS
            980                 985                 990

AAT GAC TTC CAC TTT GAC AAC GTG CTG TCG GCC ATG ATG TCG CTC TTC  3024
ASN ASP PHE HIS PHE ASP ASN VAL LEU SER ALA MET MET SER LEU PHE
        995                 1000                1005

ACG GTG TCC ACC TTC GAG GGA TGG CCC CAG CTG CTG TAC AGG GCC ATA  3072
THR VAL SER THR PHE GLU GLY TRP PRO GLN LEU LEU TYR ARG ALA ILE
    1010                1015                1020

GAC TCC AAC GAG GAG GAC ATG GGC CCC GTT TAC AAC AAC CGA GTG GAG  3120
ASP SER ASN GLU GLU ASP MET GLY PRO VAL TYR ASN ASN ARG VAL GLU
1025                1030                1035                1040

|ATG GCC ATC TTC TTC ATC ATC TAC ATC ATC CTC ATT GCC TTC TTC ATG  3168
|MET ALA ILE PHE PHE ILE ILE TYR ILE ILE LEU ILE ALA PHE PHE MET
            1045                1050                1055

ATG AAC ATC TTT GTG GGC TTT GTC ATC|GTC ACC TTC CAG GAG CAG GGG  3216
MET ASN ILE PHE VAL GLY PHE VAL ILE|VAL THR PHE GLN GLU GLN GLY
            1060                1065                1070

GAG ACG GAG TAC AAG AAC TGC GAG CTG GAC AAG AAC CAG CGC CAG TGT  3264
GLU THR GLU TYR LYS ASN CYS GLU LEU ASP LYS ASN GLN ARG GLN CYS
        1075                1080                1085

GTG CAG TAT GCC CTG AAG GCC CGC CCA CTT CGG TGC TAC ATC CCC AAG  3312
VAL GLN TYR ALA LEU LYS ALA ARG PRO LEU ARG CYS TYR ILE PRO LYS
        1090                1095                1100
```

FIGURE 1g

```
AAC CCA TAC CAG TAC CAG GTG TGG TAC GTC GTC ACC TCC TCC TAC TTT  3360
ASN PRO TYR GLN TYR GLN VAL TRP TYR VAL VAL THR SER SER TYR PHE
1105            1110                1115                1120

GAA TAC CTG ATG TTC GCC CTC ATC ATG CTC AAC ACC ATC TGC CTG GGC  3408
GLU TYR LEU MET PHE ALA LEU ILE MET LEU ASN THR ILE CYS LEU GLY
                1125                1130                1135

ATG CAG CAC TAC CAC CAG TCG GAG GAG ATG AAC CAC ATC TCA GAC ATC  3456
MET GLN HIS TYR HIS GLN SER GLU GLU MET ASN HIS ILE SER ASP ILE
        1140                1145                1150

CTC AAT GTG GCC TTC ACC ATC ATC TTC ACG CTG GAG ATG ATT CTC AAG  3504
LEU ASN VAL ALA PHE THR ILE ILE PHE THR LEU GLU MET ILE LEU LYS
    1155                1160                1165

CTC TTG GCG TTC AAG GCC AGG GGC TAT TTC GGA GAC CCC TGG AAT GTG  3552
LEU LEU ALA PHE LYS ALA ARG GLY TYR PHE GLY ASP PRO TRP ASN VAL
        1170            1175                1180

TTC GAC TTC CTG ATC GTC ATC GGC AGC ATC ATT GAC GTC ATC CTC AGC  3600
PHE ASP PHE LEU ILE VAL ILE GLY SER ILE ILE ASP VAL ILE LEU SER
1185                1190                1195                1200

GAG ATC GAC ACT TTC CTG GCC TCC AGC GGG GGA CTG TAT TGC CTG GGT  3648
GLU ILE ASP THR PHE LEU ALA SER SER GLY GLY LEU TYR CYS LEU GLY
                1205                1210                1215

GGC GGC TGC GGG AAC GTT GAC CCA GAC GAG AGC GCC CGC ATC TCC AGT  3696
GLY GLY CYS GLY ASN VAL ASP PRO ASP GLU SER ALA ARG ILE SER SER
                1220                1225                1230

GCC TTC TTC CGC CTG TTC CGG GTT ATG AGG CTG ATC AAG CTG CTG AGT  3744
ALA PHE PHE ARG LEU PHE ARG VAL MET ARG LEU ILE LYS LEU LEU SER
        1235                1240                1245

CGG GCC GAG GGC GTG CGC ACG CTG CTG TGG ACG TTC ATC AAG TCC TTC  3792
ARG ALA GLU GLY VAL ARG THR LEU LEU TRP THR PHE ILE LYS SER PHE
        1250            1255                1260

CAG GCC CTG CCC TAC GTG GCC CTG CTC ATC GTC ATG CTG TTC TTC ATC  3840
GLN ALA LEU PRO TYR VAL ALA LEU LEU ILE VAL MET LEU PHE PHE ILE
1265                1270                1275                1280
```

FIGURE 1h

```
TAC GCC GTC ATC GGC ATG CAG ATG TTT GGA AAG ATC GCC CTG GTG GAC  3888
TYR ALA VAL ILE GLY MET GLN MET PHE GLY LYS ILE ALA LEU VAL ASP
            1285                1290                1295

GGG ACC CAG ATC AAC CGC AAC AAC AAC TTC CAG ACC TTC CCG CAG GCC  3936
GLY THR GLN ILE ASN ARG ASN ASN ASN PHE GLN THR PHE PRO GLN ALA
            1300                1305                1310

GTG CTG CTG CTC TTC AGG TGT GCG ACA GGG GAG GCG TGG CAA GAG ATC  3984
VAL LEU LEU LEU PHE ARG CYS ALA THR GLY GLU ALA TRP GLN GLU ILE
            1315                1320                1325

CTG CTG GCC TGC AGC TAC GGG AAG TTG TGC GAC CCA GAG TCA GAC TAC  4032
LEU LEU ALA CYS SER TYR GLY LYS LEU CYS ASP PRO GLU SER ASP TYR
            1330                1335                1340

GCC CCG GGC GAG GAG TAC ACG TGT GGC ACC AAC TTC GCC TAC TAC TAC  4080
ALA PRO GLY GLU GLU TYR THR CYS GLY THR ASN PHE ALA TYR TYR TYR
1345                1350                1355                1360

TTC ATC AGC TTC TAC ATG CTC TGC GCC TTC CTG ATC ATC AAC CTC TTC  4128
PHE ILE SER PHE TYR MET LEU CYS ALA PHE LEU ILE ILE ASN LEU PHE
            1365                1370                1375

GTG GCT GTC ATC ATG GAC AAC TTT GAC TAC CTG ACA CGC GAC TGG TCC  4176
VAL ALA VAL ILE MET ASP ASN PHE ASP TYR LEU THR ARG ASP TRP SER
            1380                1385                1390

ATC CTG GGC CCT CAC CAC CTG GAC GAG TTC AAG GCC ATC TGG GCA GAG  4224
ILE LEU GLY PRO HIS HIS LEU ASP GLU PHE LYS ALA ILE TRP ALA GLU
            1395                1400                1405

TAT GAC CCA GAG GCC AAG GGG CGA ATC AAG CAC CTG GAC GTG GTG ACC  4272
TYR ASP PRO GLU ALA LYS GLY ARG ILE LYS HIS LEU ASP VAL VAL THR
    1410                1415                1420

CTG CTG AGA AGG ATC CAG CCC CCT CTG GGC TTC GGG AAG TTC TGT CCA  4320
LEU LEU ARG ARG ILE GLN PRO PRO LEU GLY PHE GLY LYS PHE CYS PRO
1425                1430                1435                1440

CAC CGG GTG GCC TGT AAG CGC CTG GTG GGC ATG AAC ATG CCC CTG AAC  4368
HIS ARG VAL ALA CYS LYS ARG LEU VAL GLY MET ASN MET PRO LEU ASN
            1445                1450                1455

AGT GAC GGC ACG GTC ACC TTC AAT GCC ACG CTC TTT GCC CTG GTG CGC  4416
SER ASP GLY THR VAL THR PHE ASN ALA THR LEU PHE ALA LEU VAL ARG
            1460             *  1465                1470

ACG GCC CTC AAG ATC AAG ACA GAA GGT AAC TTC GAG CAG GCC AAC GAG  4464
THR ALA LEU LYS ILE LYS THR GLU GLY ASN PHE GLU GLN ALA ASN GLU
            1475                1480                1485
```

FIGURE 1i

```
GAG CTG AGG GCC ATC ATC AAG AAG ATC TGG AAG AGA ACC AGC ATG AAG  4512
GLU LEU ARG ALA ILE ILE LYS LYS ILE TRP LYS ARG THR SER MET LYS
    1490                1495                1500     P

CTA CTG GAC CAG GTC ATC CCT CCC ATA GGA GAT GAC GAG GTG ACC GTG  4560
LEU LEU ASP GLN VAL ILE PRO PRO ILE GLY ASP ASP GLU VAL THR VAL
1505                1510                1515                1520

GGG AAG TTC TAC GCC ACA TTC CTC ATC CAG GAG CAC TTC CGG AAG TTC  4608
GLY LYS PHE TYR ALA THR PHE LEU ILE GLN GLU HIS PHE ARG LYS PHE
                1525                1530                1535

ATG AAG CGC CAG GAG GAA TAT TAT GGG TAT CGG CCC AAG AAG GAC ACC  4656
MET LYS ARG GLN GLU GLU TYR TYR GLY TYR ARG PRO LYS LYS ASP THR
            1540                1545                1550

GTG CAG ATC CAG GCT GGG CTG CGG ACC ATA GAG GAG GAG GCG GCC CCT  4704
VAL GLN ILE GLN ALA GLY LEU ARG THR ILE GLU GLU GLU ALA ALA PRO
        1555                1560                1565

GAG ATC CGC CGC ACC ATC TCA GGA GAC CTG ACC GCC GAG GAG GAG CTG  4752
GLU ILE ARG ARG THR ILE SER GLY ASP LEU THR ALA GLU GLU GLU LEU
    1570                1575                1580
                        P

GAG AGA GCC ATG GTG GAG GCT GCG ATG GAG GAG AGG ATC TTC CGG AGG  4800
GLU ARG ALA MET VAL GLU ALA ALA MET GLU GLU ARG ILE PHE ARG ARG
1585                1590                1595                1600

ACC GGA GGC CTG TTT GGC CAG GTG GAC ACC TTC CTG GAA AGG ACC AAC  4848
THR GLY GLY LEU PHE GLY GLN VAL ASP THR PHE LEU GLU ARG THR ASN
                1605                1610                1615

TCC CTA CCC CCG GTG ATG GCC AAC CAA AGA CCG CTC CAG TTT GCT GAG  4896
SER LEU PRO PRO VAL MET ALA ASN GLN ARG PRO LEU GLN PHE ALA GLU
            1620                1625                1630

ATA GAA ATG GAA GAG CTT GAG TCG CCT GTC TTC TTG GAG GAC TTC CCT  4944
ILE GLU MET GLU GLU LEU GLU SER PRO VAL PHE LEU GLU ASP PHE PRO
        1635                1640                1645

CAA GAC GCA AGA ACC AAC CCT CTC GCT CGT GCC AAT ACC AAC AAC GCC  4992
GLN ASP ALA ARG THR ASN PRO LEU ALA ARG ALA ASN THR ASN ASN ALA
    1650                1655                1660

AAT GCC AAT GTT GCC TAT GGC AAC AGC AAC CAT AGC AAC AAC CAG ATG  5040
ASN ALA ASN VAL ALA TYR GLY ASN SER ASN HIS SER ASN ASN GLN MET
1665                1670            *   1675                1680

TTT TCC AGC GTC CAC TGT GAA AGG GAG TTC CCG GGA GAG GCG GAG ACA  5088
PHE SER SER VAL HIS CYS GLU ARG GLU PHE PRO GLY GLU ALA GLU THR
                1685                1690                1695
```

FIGURE 1j

```
CCG GCT GCC GGA CGA GGA GCC CTC AGC CAC TCC CAC AGG GCC CTG GGA   5136
PRO ALA ALA GLY ARG GLY ALA LEU SER HIS SER HIS ARG ALA LEU GLY
            1700                1705                1710

CCT CAC AGC AAG CCC TGT GCT GGA AAA CTG AAT GGG CAG CTG GTC CAG   5184
PRO HIS SER LYS PRO CYS ALA GLY LYS LEU ASN GLY GLN LEU VAL GLN
            1715                1720                1725

CCG GGA ATG CCC ATC AAC CAG GCA CCT CCT GCC CCC TGC CAG CAG CCT   5232
PRO GLY MET PRO ILE ASN GLN ALA PRO PRO ALA PRO CYS GLN GLN PRO
        1730                1735                1740

AGC ACA GAT CCC CCA GAG CGC GGG CAG AGG AGG ACC TCC CTG ACA GGG   5280
SER THR ASP PRO PRO GLU ARG GLY GLN ARG ARG THR SER LEU THR GLY
1745                1750                1755    P           1760

TCT CTG CAA GAC GAA GCA CCC CAG AGG AGG AGC TCC GAG GGG AGC ACC   5328
SER LEU GLN ASP GLU ALA PRO GLN ARG ARG SER SER GLU GLY SER THR
                1765                1770    P           1775

CCC AGG CGC CCG GCT CCT GCT ACA GCT CTG CTG ATC CAA GAG GCT CTG   5376
PRO ARG ARG PRO ALA PRO ALA THR ALA LEU LEU ILE GLN GLU ALA LEU
            1780                1785                1790

GTT CGA GGG GGC CTG GAC ACC TTG GCA GCT GAT GCT GGC TTC GTC ATG   5424
VAL ARG GLY GLY LEU ASP THR LEU ALA ALA ASP ALA GLY PHE VAL MET
            1795                1800                1805

GCA ACA AGC CAG GCC CTG GTA GAC GCC TGT CAG ATG GAA CCG GAG GAA   5472
ALA THR SER GLN ALA LEU VAL ASP ALA CYS GLN MET GLU PRO GLU GLU
        1810                1815                1820

GTA GAG GTC GCA GCC ACA GAG CTA CTG AAA GAG CGA GAG TCC GTC CAG   5520
VAL GLU VAL ALA ALA THR GLU LEU LEU LYS GLU ARG GLU SER VAL GLN
1825                1830                1835                1840

GGC ATG GCC AGT GTC CCG GGA AGC CTG AGC CGC AGG TCC TCC CTG GGC   5568
GLY MET ALA SER VAL PRO GLY SER LEU SER ARG ARG SER SER LEU GLY
                1845                1850        P   1855

AGC CTT GAC CAG GTC CAG GGC TCC CAG GAA ACC CTT ATT CCT CCC AGG   5616
SER LEU ASP GLN VAL GLN GLY SER GLN GLU THR LEU ILE PRO PRO ARG
            1860                1865                1870

CCG TGA TGGCTGTGCA GTGTCCACAT GACCAAGGCG AGGGGGACAG TGCGTGCAGA    5672
PRO

AGCTCAGCCC TGCATGGCAG CCTCCCTCTG TCTCAGCCCT CCTGCTGAGC            5722
TGGGGCGGTC TGGAACCGAC CAGGAAGCCA GGAGCCTCCC CTGGCCAGCA            5772
AGAGGCATGA TTCTAAAGCA TCCAGAAAGG CCTGGTCAGT GCCACTCCCC            5822
AGCAGGACAT TAAAGTCTCT AGGTCTGTGG CAAAAAAAAA AAAAAAAAA             5872
AAAAAAAAAA AAAAAAAAAA AAAAA                                       5897
```

FIGURE 2a

```
5'                                                         AGAAGGGA   -301
GGGCGAGCGT GGTGTGTGCG CGCTCGGGCG CCGGCGGCAC CGCCGAGGTC TGTTGGCAAA   -241
AGTCGCCCTT GATGGCGGCG GAGGCGAGGC AGCCGCGGCG CCGAACAGCC GACGCGCGCT   -181
AGCGGGGTCC GCCCGCCCCT TTCCCAGAGC CCAGCGCCGC CGTTCGCCGC CGCCGCCGCC   -121
CGCCCGCGCG CCGTTCGCCG CCGCCGCCGC CCGCGGGTGG CAGCGCCGCT CGGTCCCCGG    -61
CCCCGGGGCC GGCTGGGGGG CGGTCGGGGC GTGTGAGGGG CTTGCTCCCA GCTCGCGAAG     -1
```

| | | | | | | | | | | | | | | | | |
|---|---|---|---|---|---|---|---|---|---|---|---|---|---|---|---|---|
| ATG | GCT | GCG | GGC | CGC | CCG | CTG | GCC | TGG | ACG | CTG | ACA | CTT | TGG | CAG | GCG | 48 |
| MET | ALA | ALA | GLY | ARG | PRO | LEU | ALA | TRP | THR | LEU | THR | LEU | TRP | GLN | ALA | |
| | -25 | | | | -20 | | | | | -15 | | | | | | |

```
TGG CTG ATC CTG ATC GGG CCC TCG TCG GAG GAG CCG TTC CCT TCA GCC     96
TRP LEU ILE LEU ILE GLY PRO SER SER GLU GLU PRO PHE PRO SER ALA
-10              -5            -1 |+1                 5

GTC ACT ATC AAG TCA TGG GTG GAT AAG ATG CAA GAA GAC CTG GTC ACA    144
VAL THR ILE LYS SER TRP VAL ASP LYS MET GLN GLU ASP LEU VAL THR
            10                  15                      20

CTG GCA AAA ACA GCA AGT GGA GTC AAT CAG CTT GTT GAT ATT TAT GAG    192
LEU ALA LYS THR ALA SER GLY VAL ASN GLN LEU VAL ASP ILE TYR GLU
        25                  30                  35

AAA TAT CAA GAT TTG TAT ACT GTG GAA CCA AAT AAT GCA CGT CAG CTG    240
LYS TYR GLN ASP LEU TYR THR VAL GLU PRO ASN ASN ALA ARG GLN LEU
    40                  45                  50

GTG GAA ATT GCA GCC AGA GAC ATT GAG AAG CTT CTC AGC AAC AGA TCT    288
VAL GLU ILE ALA ALA ARG ASP ILE GLU LYS LEU LEU SER ASN ARG SER
55                  60                  65          *       70

AAA GCC CTG GTG CGC CTG GCT TTG GAA GCA GAG AAA GTT CAA GCA GCC    336
LYS ALA LEU VAL ARG LEU ALA LEU GLU ALA GLU LYS VAL GLN ALA ALA
                75                  80                  85

CAC CAA TGG AGG GAA GAT TTT GCA AGC AAT GAA GTT GTC TAC TAT AAC    384
HIS GLN TRP ARG GLU ASP PHE ALA SER ASN GLU VAL VAL TYR TYR ASN
            90                  95                  100

GCG AAG GAT GAT CTT GAT CCT GAA AAA AAT GAC AGT GAA CCA GGC AGC    432
ALA LYS ASP ASP LEU ASP PRO GLU LYS ASN ASP SER GLU PRO GLY SER
        105                 110    *           115

CAG AGG ATC AAA CCT GTT TTC ATT GAC GAT GCT AAC TTT AGA AGA CAA    480
GLN ARG ILE LYS PRO VAL PHE ILE ASP ASP ALA ASN PHE ARG ARG GLN
    120                 125                 130

GTA TCC TAT CAG CAC GCA GCT GTC CAT ATC CCC ACT GAC ATC TAT GAA    528
VAL SER TYR GLN HIS ALA ALA VAL HIS ILE PRO THR ASP ILE TYR GLU
135                 140                 145                 150
```

FIGURE 2b

```
GGA TCG ACA ATC GTG TTA AAC GAA CTC AAC TGG ACA AGT GCC TTA GAT    576
GLY SER THR ILE VAL LEU ASN GLU LEU ASN TRP THR SER ALA LEU ASP
            155                 160                 165
                                 *

GAC GTT TTC AAA AAA AAT CGA GAG GAA GAC CCT TCA CTG TTG TGG CAG    624
ASP VAL PHE LYS LYS ASN ARG GLU GLU ASP PRO SER LEU LEU TRP GLN
            170                 175                 180

GTG TTT GGC AGT GCC ACT GGC CTG GCC CGG TAT TAC CCA GCT TCT CCA    672
VAL PHE GLY SER ALA THR GLY LEU ALA ARG TYR TYR PRO ALA SER PRO
            185                 190                 195

TGG GTT GAT AAT AGC CGA ACC CCA AAC AAG ATT GAT CTT TAT GAT GTA    720
TRP VAL ASP ASN SER ARG THR PRO ASN LYS ILE ASP LEU TYR ASP VAL
            200                 205                 210

CGC AGA AGA CCA TGG TAC ATC CAA GGT GCT GCA TCC CCT AAA GAT ATG    768
ARG ARG ARG PRO TRP TYR ILE GLN GLY ALA ALA SER PRO LYS ASP MET
215                 220                 225                 230

CTT ATT CTG GTG GAT GTG AGT GGA AGC GTT AGT GGA CTG ACA CTC AAA    816
LEU ILE LEU VAL ASP VAL SER GLY SER VAL SER GLY LEU THR LEU LYS
            235                 240                 245

CTC ATC CGG ACA TCC GTC TCC GAA ATG TTG GAA ACC CTC TCA GAT GAT    864
LEU ILE ARG THR SER VAL SER GLU MET LEU GLU THR LEU SER ASP ASP
            250                 255                 260

GAT TTT GTG AAC GTG GCT TCA TTT AAC AGC AAT GCT CAG GAT GTA AGC    912
ASP PHE VAL ASN VAL ALA SER PHE ASN SER ASN ALA GLN ASP VAL SER
            265                 270                 275

TGC TTT CAG CAC CTT GTC CAA GCA AAT GTA AGA AAT AAG AAA GTG TTG    960
CYS PHE GLN HIS LEU VAL GLN ALA ASN VAL ARG ASN LYS LYS VAL LEU
            280                 285                 290

AAA GAT GCA GTG AAT AAT ATC ACA GCA AAA GGA ATC ACA GAT TAT AAG   1008
LYS ASP ALA VAL ASN ASN ILE THR ALA LYS GLY ILE THR ASP TYR LYS
295                 300                 305                 310
                     *

AAG GGC TTT AGT TTT GCT TTT GAG CAG CTG CTT AAT TAT AAT GTA TCC   1056
LYS GLY PHE SER PHE ALA PHE GLU GLN LEU LEU ASN TYR ASN VAL SER
            315                 320                  *  325

AGA GCC AAC TGC AAT AAG ATT ATC ATG TTG TTC ACG GAC GGA GGA GAA   1104
ARG ALA ASN CYS ASN LYS ILE ILE MET LEU PHE THR ASP GLY GLY GLU
            330                 335                 340
```

FIGURE 2c

```
GAG AGA GCC CAG GAG ATA TTT GCC AAA TAC AAT AAA GAC AAG AAA GTA    1152
GLU ARG ALA GLN GLU ILE PHE ALA LYS TYR ASN LYS ASP LYS LYS VAL
        345                 350                 355

CGT GTA TTC ACA TTC TCA GTT GGC CAA CAT AAT TAC GAC AGA GGA CCT    1200
ARG VAL PHE THR PHE SER VAL GLY GLN HIS ASN TYR ASP ARG GLY PRO
        360                 365                 370

ATT CAG TGG ATG GCT TGC GAA AAT AAA GGT TAT TAT TAT GAA ATT CCA    1248
ILE GLN TRP MET ALA CYS GLU ASN LYS GLY TYR TYR TYR GLU ILE PRO
375                 380                 385                 390

TCC ATT GGA GCC ATA AGA ATT AAT ACT CAG GAA TAC CTA GAT GTT CTG    1296
SER ILE GLY ALA ILE ARG ILE ASN THR GLN GLU TYR LEU ASP VAL LEU
        395                 400                 405

GGA AGA CCG ATG GTT TTA GCA GGA GAC AAA GCT AAG CAA GTC CAA TGG    1344
GLY ARG PRO MET VAL LEU ALA GLY ASP LYS ALA LYS GLN VAL GLN TRP
        410                 415                 420

ACA AAT GTG TAC CTG GAT GCA CTG GAA CTG GGA CTT GTC ATT ACT GGA    1392
THR ASN VAL TYR LEU ASP ALA LEU GLU LEU GLY LEU VAL ILE THR GLY
        425                 430                 435

ACT CTT CCG GTC TTC AAC ATA ACT GGC CAA TTT GAA AAT AAG ACA AAC    1440
THR LEU PRO VAL PHE ASN ILE THR GLY GLN PHE GLU ASN LYS THR ASN
        440          *  445                 450  *

TTA AAG AAC CAG CTG ATT CTT GGA GTG ATG GGA GTT GAT GTG TCT TTG    1488
LEU LYS ASN GLN LEU ILE LEU GLY VAL MET GLY VAL ASP VAL SER LEU
455                 460                 465                 470

GAA GAT ATT AAA AGA CTG ACA CCA CGT TTT ACA CTC TGC CCC AAT GGC    1536
GLU ASP ILE LYS ARG LEU THR PRO ARG PHE THR LEU CYS PRO ASN GLY
                475                 480                 485

TAC TAT TTT GCA ATT GAT CCT AAT GGT TAT GTG TTA TTA CAT CCA AAT    1584
TYR TYR PHE ALA ILE ASP PRO ASN GLY TYR VAL LEU LEU HIS PRO ASN
            490                 495                 500

CTT CAG CCA AAG CCT ATT GGT GTA GGT ATA CCA ACA ATT AAT TTG AGA    1632
LEU GLN PRO LYS PRO ILE GLY VAL GLY ILE PRO THR ILE ASN LEU ARG
        505                 510                 515

AAA AGG AGA CCC AAT GTT CAG AAC CCC AAA TCT CAG GAG CCA GTG ACA    1680
LYS ARG ARG PRO ASN VAL GLN ASN PRO LYS SER GLN GLU PRO VAL THR
        520                 525                 530

TTG GAT TTC CTC GAT GCA GAG TTG GAG AAT GAC ATT AAA GTG GAG ATT    1728
LEU ASP PHE LEU ASP ALA GLU LEU GLU ASN ASP ILE LYS VAL GLU ILE
535                 540                 545                 550
```

FIGURE 2d

```
CGA AAT AAA ATG ATC GAT GGA GAA AGT GGA GAA AAA ACA TTC AGA ACT   1766
ARG ASN LYS MET ILE ASP GLY GLU SER GLY GLU LYS THR PHE ARG THR
            555             560             565

CTG GTT AAA TCT CAA GAT GAG AGA TAT ATT GAC AAA GGA AAC AGG ACA   1824
LEU VAL LYS SER GLN ASP GLU ARG TYR ILE ASP LYS GLY ASN ARG THR
            570             575              *
                                            580

TAC ACG TGG ACT CCT GTC AAC GGC ACA GAT TAT AGC AGT TTG GCC TTG   1872
TYR THR TRP THR PRO VAL ASN GLY THR ASP TYR SER SER LEU ALA LEU
        585          *  590             595

GTA TTA CCA ACC TAC AGT TTT TAC TAT ATA AAA GCC AAA ATA GAA GAG   1920
VAL LEU PRO THR TYR SER PHE TYR TYR ILE LYS ALA LYS ILE GLU GLU
    600             605             610

ACA ATA ACT CAG GCC AGA TAT TCA GAA ACA CTG AAA CCG GAT AAT TTT   1968
THR ILE THR GLN ALA ARG TYR SER GLU THR LEU LYS PRO ASP ASN PHE
615             620             625             630

GAA GAA TCT GGC TAC ACA TTC CTA GCA CCA AGA GAT TAC TGC AGT GAC   2016
GLU GLU SER GLY TYR THR PHE LEU ALA PRO ARG ASP TYR CYS SER ASP
                635             640             645

CTT AAA CCT TCA GAT AAT AAC ACT GAA TTT CTT TTA AAT TTC AAT GAG   2064
LEU LYS PRO SER ASP ASN ASN THR GLU PHE LEU LEU ASN PHE ASN GLU
            650  *          655             660

TTT ATT GAT AGA AAA ACT CCA AAC AAC CCA TCC TGT AAT ACA GAC TTG   2112
PHE ILE ASP ARG LYS THR PRO ASN ASN PRO SER CYS ASN THR ASP LEU
        665             670  *          675

ATT AAT AGA GTC TTG CTG GAT GCA GGC TTT ACA AAT GAA CTT GTT CAA   2160
ILE ASN ARG VAL LEU LEU ASP ALA GLY PHE THR ASN GLU LEU VAL GLN
        680             685             690

AAT TAC TGG AGT AAG CAG AAG AAT ATC AAG GGA GTG AAA GCA CGG TTT   2208
ASN TYR TRP SER LYS GLN LYS ASN ILE LYS GLY VAL LYS ALA ARG PHE
695             700             705             710

GTT GTG ACT GAT GGT GGG ATT ACC AGA GTT TAT CCC AAA GAG GCT GGA   2256
VAL VAL THR ASP GLY GLY ILE THR ARG VAL TYR PRO LYS GLU ALA GLY
            715             720             725

GAA AAT TGG CAG GAA AAC CCA GAG ACA TAT GAA GAC AGC TTC TAT AAA   2304
GLU ASN TRP GLN GLU ASN PRO GLU THR TYR GLU ASP SER PHE TYR LYS
        730             735             740

AGG AGC CTC GAT AAT GAT AAC TAC GTT TTC ACT GCT CCC TAC TTT AAC   2352
ARG SER LEU ASP ASN ASP ASN TYR VAL PHE THR ALA PRO TYR PHE ASN
            745             750             755          *
```

FIGURE 2f

```
TGC ATC ACT GAG CAA ACC CAG TAT TTC TTC GAT AAT GAC AGC AAA TCG    2976
CYS ILE THR GLU GLN THR GLN TYR PHE PHE ASP ASN ASP SER LYS SER
            955                     960   *             965

TTC AGT GGG GTA TTA GAC TGT GGG AAT TGT TCC AGA ATC TTT CAT GTA    3024
PHE SER GLY VAL LEU ASP CYS GLY ASN CYS SER ARG ILE PHE HIS VAL
            970                 975                 980
                                 *
GAA AAG CTC ATG AAC ACC AAT TTA ATA TTC ATA ATG GTA GAG AGC AAG    3072
GLU LYS LEU MET ASN THR ASN LEU ILE PHE ILE MET VAL GLU SER LYS
            985                 990                 995

GGG ACA TGT CCC TGT GAC ACA CGG CTG CTC ATA CAA GCA GAG CAA ACT    3120
GLY THR CYS PRO CYS ASP THR ARG LEU LEU ILE GLN ALA GLU GLN THR
        1000                1005                1010

TCT GAT GGA CCA GAT CCT TGT GAT ATG GTT AAG CAA CCC AGA TAT CGA    3168
SER ASP GLY PRO ASP PRO CYS ASP MET VAL LYS GLN PRO ARG TYR ARG
1015                1020                1025                1030

AAA GGG CCA GAT GTC TGC TTT GAC AAC AAT GTC CTG GAG GAT TAT ACT    3218
LYS GLY PRO ASP VAL CYS PHE ASP ASN ASN VAL LEU GLU ASP TYR THR
                1035                1040                1045

GAC TGC GGT GGG GTC TCT GGA TTA AAT|CCT TCC CTG TGG TCC ATC ATC    3264
ASP CYS GLY GLY VAL SER GLY LEU ASN|PRO SER LEU TRP SER ILE ILE
            1050                1055                1060
                                 *
GGG ATA CAG TTT GTA CTG CTT TGG CTG GTT TCT GGC AGC|AGA CAC TGC    3312
GLY ILE GLN PHE VAL LEU LEU TRP LEU VAL SER GLY SER|ARG HIS CYS
            1065                1070            1075

CTG TTA TGA CCTTCTAAAA CCAAATCTCC ATAATTAAAC TCCAGACCCT            3361
LEU LEU
    1080

GCCACAACAT GATCCCTCCG TTATGTTAAA GTAGGGTCAA CTGTTAAATC              3411
AGAACATTAG CTGGGCCTCT GCCATGGCAG AGCCCTAAGG CGCAGACTCA              3461
TCAGGCACCC ACTGGCTGCA TGTCAGGGTG TCC ...... 3'                     3494
```

FIGURE 3a

```
        Human Neuronalα2
........................GGGCGGGGGAGGGGGATTGATCTTC    25
Rabbit Skeletal Muscleα2 ||||| | |||||| |       |
CCCGGGGCCGGCTGGGGGGCGGTCGGGGCGTGTGAGGGGCTTGCTCCCAG   299
            Start
GATCGCAAGATGGCTGCTGGCTGCCTGCTGGCCTTGACTCTGACACTTTT    75
       ||||||||||||  |||  |||  |||||||||  |||  ||||||||||
CTCGCGAAGATGGCTGCGGGCCGCCCGCTGGCCTGGACGCTGACACTTTG   349

CCAATCTT......TGCTCATCGGCCCCTCGTCGGAGGAGCCGTTCCCTT   119
||  ||         |  ||  ||||||  ||||||||||||||||||||||||||
Gcaggcgtggctgatcctgatcgggccctcgtcggaggagccgttccctt   399

CGGCCGTCACTATCAAATCATGGGTGGATAAGATGCAAGAAGACCTTGTC   169
|  ||||||||||||||||  ||||||||||||||||||||||||||||||||  |||
cagccgtcactatcaagtcatgggtggataagatgcaagaagacctggtc   449

ACACTGGCAAAAACAGCAAGTGGAGTCAATCAGCTTGTTGATATTTATGA   219
||||||||||||||||||||||||||||||||||||||||||||||||||
acactggcaaaaacagcaagtggagtcaatcagcttgttgatatttatga   499

GAAATATCAAGATTTGTATACTGTGGAACCAAATAATGCACGCCAGCTGG   269
||||||||||||||||||||||||||||||||||||||||||| |||||||
gaaatatcaagatttgtatactgtggaaccaaataatgcacgtcagctgg   549

TAGAAATTGCAGCCAGGGATATTGAGAAACTTCTGAGCAACAGATCTAAA   319
|  ||||||||||||||||| || |||||||||| ||||| ||||||||||||||
tggaaattgcagccagagacattgagaagcttctcagcaACAGATCTAAA   599

GCCCTGGTGAGCCTGGCATTGGAAGCGGAGAAAGTTCAAGCAGCTCACCA   369
|||||||||  ||||||| |||||||  |||||||||||||||||||  |||||
GCCCTGGTGCGCCTGGCTTTGGAAGCAGAGAAAGTTCAAGCAGCCCACCA   649
```

FIGURE 3b

```
GTGGAGAGAAGATTTTGCAAGCAATGAAGTTGTCTACTACAATGCAAAGG  419
|||||  |||||||||||||||||||||||||||||||| ||  ||  ||||
ATGGAGGGAAGATTTTGCAAGCAATGAAGTTGTCTACTATAACGCGAAGG  699

ATGATCTCGATCCTGAGAAAAATGACAGTGAGCCAGGCAGCCAGAGGATA  469
|||||||  ||||||||  ||||||||||||||  |||||||||||||||
ATGATCTTGATCCTGAAAAAAATGACAGTGAACCAGGCAGCCAGAGGATC  749

AAACCTGTTTTCATTGAAGATGCTAATTTTGGACGACAAATATCTTATCA  519
||||||||||||||||| ||||||||||  || ||||| ||||  |||||
AAACCTGTTTTCATTGACGATGCTAACTTTAGAAGACAAGTATCCTATCA  799

GCACGCAGCAGTCCATATTCCTACTGACATCTATGAGGGCTCAACAATTG  569
|||||||||  ||||||  ||||||||||||||||| || || |||||| |
GCACGCAGCTGTCCATATCCCCACTGACATCTATGAAGGATCGACAATCG  849

TGTTAAATGAACTCAACTGGACAAGTGCCTTAGATGAAGTTTTCAAAAAG  619
|||||| |||||||||||||||||||||||||||||| |||||||||||
TGTTAAACGAACTCAACTGGACAAGTGCCTTAGATGACGTTTTCAAAAAA  899

AATCGCGAGGAAGACCCTTCATTATTGTGGCAGGTTTTTGGCAGTGCCAC  669
|||||  ||||||||||||| | ||| ||||||| ||||||||||||||
AATCGAGAGGAAGACCCTTCACTGTTGTGGCAGGTGTTTGGCAGTGCCAC  949

TGGCCTAGCTCGATATTATCCAGCTTCACCATGGGTTGATAATGGTAGAA  719
|||||| ||  || |||||| |||||| ||||||||||||||||| |||
TGGCCTGGCCCGGTATTACCCAGCTTCTCCATGGGTTGATAATAGCCGAA  999

CTCCAAATATGATTGACCTTTATGATGTACGCAGAAGACCATGGTACATC  769
| |||| | ||||||  |||||||||||||||||||||||||||||||||
CCCCAAACAAGATTGATCTTTATGATGTACGCAGAAGACCATGGTACATC  1049

CAAGGAGCTGCATCTCCTAAAGACATGCTTATTCTGGTGGATGTGAGTGG  819
||||| ||||||||  ||||||| ||||||||||||||||||||||||||
CAAGGTGCTGCATCCCCTAAAGATATGCTTATTCTGGTGGATGTGAGTGG  1099
```

FIGURE 3c

```
AAGTGTTAGTGGATTGACACTTAAACTGATCCGAACATCTGTCTCCGAAA    869
|||  |||||||||| |||||||  |||||  |||||  |||||  ||||||||||
AAGCGTTAGTGGACTGACACTCAAACTCATCCGGACATCCGTCTCCGAAA   1149

TGTTAGAAACCCTCTCAGATGATGATTTCGTGAATGTAGCTTCATTTAAC    919
||||  ||||||||||||||||||||||||| |||||  || ||||||||||||
TGTTGGAAACCCTCTCAGATGATGATTTTGTGAACGTGGCTTCATTTAAC   1199

AGCAATGCTCAGGATGTAAGCTGTTTTCAGCACCTTGTCCAAGCAAATGT    969
||||||||||||||||||||||||| ||||||||||||||||||||||||||
AGCAATGCTCAGGATGTAAGCTGCTTTCAGCACCTTGTCCAAGCAAATGT   1249

AAGAAATAAAAAAGTGTTGAAAGACGCGGTGAATAATATCACAGCCAAAG   1019
||||||||  ||||||||||||||  ||| |||||||||||||||||  ||||
AAGAAATAAGAAAGTGTTGAAAGATGCAGTGAATAATATCACAGCAAAAG   1299

GAATTACAGATTATAAGAAGGGCTTTAGTTTTGCTTTTAACAGCTGCTT   1069
|||| ||||||||||||||||||||||||||||||||||||  ||||||||
GAATCACAGATTATAAGAAGGGCTTTAGTTTTGCTTTTGAGCAGCTGCTT   1349

AATTATAATGTTTCCAGAGCAAACTGCAATAAGATTATTATGCTATTCAC   1119
|||||||||||  |||||||| |||||||||||||||||  ||| |  |||||
AATTATAATGTATCCAGAGCCAACTGCAATAAGATTATCATGTTGTTCAC   1399

GGA...TGGAGAAGAGAGAGCCCAGGAGATATTTAACAAATACAATAAAG   1166
|||       |||||||||||||||||||||||||  |||||||||||||||
GGACGGAGGAGAAGAGAGAGCCCAGGAGATATTTGCCAAATACAATAAAG   1449

ATAAAAAACTACCTGTATTCACCTTCTCAGTTGGTCAACACAATTATGAC   1216
| || ||| ||| |||||||||| |||||||||| |||||  ||||| |||
ACAAGAAAGTACGTGTATTCACATTCTCAGTTGGCCAACATAATTACGAC   1499
```

FIGURE 3d

```
AGAGGACCTATTCAGTGGATGGCCTGTGAAAACAAAGGTTATTATTATGA   1266
||||||||||||||||||||||||| || ||||| ||||||||||||||||
AGAGGACCTATTCAGTGGATGGCTTGCGAAAATAAAGGTTATTATTATGA   1549

AATTCCTTCCATTGGTGCAATAAGAATCAATACTCAGGAATATTTGGATG   1316
|||||| |||||||||| || ||||||||| |||||||||||||| ||||
AATTCCATCCATTGGAGCCATAAGAATTAATACTCAGGAATACCTAGATG   1599

TTTTGGGAAGACCAATGGTTTTAGCAGGAGACAAAGCTAAGCAAGTCCAA   1366
|| |||||||||| ||||||||||||||||||||||||||||||||||||
TTCTGGGAAGACCGATGGTTTTAGCAGGAGACAAAGCTAAGCAAGTCCAA   1649

TGGACAAATGTGTACCTGGATGCATTGGAACTGGGACTTGTCATTACTGG   1416
|||||||||||||||||||||||| |||||||||||||||||||||||||
TGGACAAATGTGTACCTGGATGCACTGGAACTGGGACTTGTCATTACTGG   1699

AACTCTTCCGGTCTTCAACATAACCGGCCAATTTGAAAATAAGACAAACT   1466
|||||||||||||||||||||||| |||||||||||||||||||||||||
AACTCTTCCGGTCTTCAACATAACTGGCCAATTTGAAAATAAGACAAACT   1749

TAAAGAACCAGCTGATTCTTGGTGTGATGGGAGTAGATGTGTCTTTGGAA   1516
|||||||||||||||||||||| ||||||||||| |||||||||||||||
TAAAGAACCAGCTGATTCTTGGAGTGATGGGAGTTGATGTGTCTTTGGAA   1799

GATATTAAAAGACTGACACCACGTTTTACACTGTGCCCAATGG......   1560
|||||||||||||||||||||||||||||| ||||||||||||
GATATTAAAAGACTGACACCACGTTTTACACTCTGCCCCAATGGCTACTA   1849
```

FIGURE 1h

```
TAC GCC GTC ATC GGC ATG CAG ATG TTT GGA AAG ATC GCC CTG GTG GAC 3888
TYR ALA VAL ILE GLY MET GLN MET PHE GLY LYS ILE ALA LEU VAL ASP
                1285                1290            1295

GGG ACC CAG ATC AAC CGC AAC AAC AAC TTC CAG ACC TTC CCG CAG GCC 3936
GLY THR GLN ILE ASN ARG ASN ASN ASN PHE GLN THR PHE PRO GLN ALA
            1300            1305                1310

GTG CTG CTG CTC TTC AGG TGT GCG ACA GGG GAG GCG TGG CAA GAG ATC 3984
VAL LEU LEU LEU PHE ARG CYS ALA THR GLY GLU ALA TRP GLN GLU ILE
        1315                1320                1325

CTG CTG GCC TGC AGC TAC GGG AAG TTG TGC GAC CCA GAG TCA GAC TAC 4032
LEU LEU ALA CYS SER TYR GLY LYS LEU CYS ASP PRO GLU SER ASP TYR
    1330                1335                1340

GCC CCG GGC GAG GAG TAC ACG TGT GGC ACC AAC TTC GCC TAC TAC TAC 4080
ALA PRO GLY GLU GLU TYR THR CYS GLY THR ASN PHE ALA TYR TYR TYR
1345                1350                1355                1360

TTC ATC AGC TTC TAC ATG CTC TGC GCC TTC CTG ATC ATC AAC CTC TTC 4128
PHE ILE SER PHE TYR MET LEU CYS ALA PHE LEU ILE ILE ASN LEU PHE
                1365                1370                1375

GTG GCT GTC ATC ATG GAC AAC TTT GAC TAC CTG ACA CGC GAC TGG TCC 4176
VAL ALA VAL ILE MET ASP ASN PHE ASP TYR LEU THR ARG ASP TRP SER
            1380                1385                1390

ATC CTG GGC CCT CAC CAC CTG GAC GAG TTC AAG GCC ATC TGG GCA GAG 4224
ILE LEU GLY PRO HIS HIS LEU ASP GLU PHE LYS ALA ILE TRP ALA GLU
        1395                1400            1405

TAT GAC CCA GAG GCC AAG GGG CGA ATC AAG CAC CTG GAC GTG GTG ACC 4272
TYR ASP PRO GLU ALA LYS GLY ARG ILE LYS HIS LEU ASP VAL VAL THR
    1410                1415                1420

CTG CTG AGA AGG ATC CAG CCC CCT CTG GGC TTC GGG AAG TTC TGT CCA 4320
LEU LEU ARG ARG ILE GLN PRO PRO LEU GLY PHE GLY LYS PHE CYS PRO
1425                1430                1435                1440

CAC CGG GTG GCC TGT AAG CGC CTG GTG GGC ATG AAC ATG CCC CTG AAC 4368
HIS ARG VAL ALA CYS LYS ARG LEU VAL GLY MET ASN MET PRO LEU ASN
                1445                1450                1455

AGT GAC GGC ACG GTC ACC TTC AAT GCC ACG CTC TTT GCC CTG GTG CGC 4416
SER ASP GLY THR VAL THR PHE ASN ALA THR LEU PHE ALA LEU VAL ARG
            1460            *   1465                1470

ACG GCC CTC AAG ATC AAG ACA GAA GGT AAC TTC GAG CAG GCC AAC GAG 4464
THR ALA LEU LYS ILE LYS THR GLU GLY ASN PHE GLU GLN ALA ASN GLU
        1475                1480                1485
```

FIGURE 2a

```
5'                                                              AGAAGGGA  -301
GGGCGAGCGT GGTGTGTGCG CGCTCGGGCG CCGGCGGCAC CGCCGAGGTC TGTTGGCAAA  -241
AGTCGCCCTT GATGGCGGCG GAGGCGAGGC AGCCGCGGCG CCGAACAGCC GACGCGCGCT  -181
AGCGGGGTCC GCCCGCCCCT TTCCCAGAGC CCAGCGCCGC CGTTCGCCGC CGCCGCCGCC  -121
CGCCCGCGCG CCGTTCGCCG CCGCCGCCGC CCGCGGGTGG CAGCGCCGCT CGGTCCCCGG   -61
CCCCGGGGCC GGCTGGGGGG CGGTCGGGGC GTGTGAGGGG CTTGCTCCCA GCTCGCGAAG   -1
```

```
ATG GCT GCG GGC CGC CCG CTG GCC TGG ACG CTG ACA CTT TGG CAG GCG      48
MET ALA ALA GLY ARG PRO LEU ALA TRP THR LEU THR LEU TRP GLN ALA
    -25             -20             -15

TGG CTG ATC CTG ATC GGG CCC TCG TCG GAG GAG CCG TTC CCT TCA GCC      96
TRP LEU ILE LEU ILE GLY PRO SER SER GLU GLU PRO PHE PRO SER ALA
-10             -5              -1  +1               5

GTC ACT ATC AAG TCA TGG GTG GAT AAG ATG CAA GAA GAC CTG GTC ACA     144
VAL THR ILE LYS SER TRP VAL ASP LYS MET GLN GLU ASP LEU VAL THR
             10              15              20

CTG GCA AAA ACA GCA AGT GGA GTC CAT CAG CTT GTT GAT ATT TAT GAG     192
LEU ALA LYS THR ALA SER GLY VAL HIS GLN LEU VAL ASP ILE TYR GLU
         25              30              35

AAA TAT CAA GAT TTG TAT ACT GTG GAA CCA AAT AAT GCA CGT CAG CTG     240
LYS TYR GLN ASP LEU TYR THR VAL GLU PRO ASN ASN ALA ARG GLN LEU
         40              45              50

GTG GAA ATT GCA GCC AGA GAC ATT GAG AAG CTT CTC AGC AAC AGA TCT     288
VAL GLU ILE ALA ALA ARG ASP ILE GLU LYS LEU LEU SER ASN ARG SER
55              60              65          *           70

AAA GCC CTG GTG CGC CTG GCT TTG GAA GCA GAG AAA GTT CAA GCA GCC     336
LYS ALA LEU VAL ARG LEU ALA LEU GLU ALA GLU LYS VAL GLN ALA ALA
             75              80              85

CAC CAA TGG AGG GAA GAT TTT GCA AGC AAT GAA GTT GTC TAC TAT AAC     384
HIS GLN TRP ARG GLU ASP PHE ALA SER ASN GLU VAL VAL TYR TYR ASN
             90              95              100

GCG AAG GAT GAT CTT GAT CCT GAA AAA AAT GAC AGT GAA CCA GGC AGC     432
ALA LYS ASP ASP LEU ASP PRO GLU LYS ASN ASP SER GLU PRO GLY SER
             105             110 *           115

CAG AGG ATC AAA CCT GTT TTC ATT GAC GAT GCT AAC TTT AGA AGA CAA     480
GLN ARG ILE LYS PRO VAL PHE ILE ASP ASP ALA ASN PHE ARG ARG GLN
    120             125             130

GTA TCC TAT CAG CAC GCA GCT GTC CAT ATC CCC ACT GAC ATA TAT GAA     528
VAL SER TYR GLN HIS ALA ALA VAL HIS ILE PRO THR ASP ILE TYR GLU
135             140             145             150
```

FIGURE 2d

```
CGA AAT AAA ATG ATC GAT GGA GAA AGT GGA GAA AAA ACA TTC AGA ACT    1766
ARG ASN LYS MET ILE ASP GLY GLU SER GLY GLU LYS THR PHE ARG THR
            555             560             565

CTG GTT AAA TCT CAA GAT GAG AGA TAT ATT GAC AAA GGA AAC AGG ACA    1824
LEU VAL LYS SER GLN ASP GLU ARG TYR ILE ASP LYS GLY ASN ARG THR
            570             575              *
                                             580

TAC ACG TGG ACT CCT GTC AAC GGC ACA GAT TAT AGC AGT TTG GCC TTG    1872
TYR THR TRP THR PRO VAL ASN GLY THR ASP TYR SER SER LEU ALA LEU
            585          *  590             595

GTA TTA CCA ACC TAC AGT TTT TAC TAT ATA AAA GCC AAA ATA GAA GAG    1920
VAL LEU PRO THR TYR SER PHE TYR TYR ILE LYS ALA LYS ILE GLU GLU
    600             605             610

ACA ATA ACT CAG GCC AGA TAT TCA GAA ACA CTG AAA CCG GAT AAT TTT    1968
THR ILE THR GLN ALA ARG TYR SER GLU THR LEU LYS PRO ASP ASN PHE
615             620             625             630

GAA GAA TCT GGC TAC ACA TTC CTA GCA CCA AGA GAT TAC TGC AGT GAC    2016
GLU GLU SER GLY TYR THR PHE LEU ALA PRO ARG ASP TYR CYS SER ASP
            635             640             645

CTT AAA CCT TCA GAT AAT AAC ACT GAA TTT CTT TTA AAT TTC AAT GAG    2064
LEU LYS PRO SER ASP ASN ASN THR GLU PHE LEU LEU ASN PHE ASN GLU
            650             655             660

TTT ATT GAT AGA AAA ACT CCA AAC AAC CCA TCC TGT AAT ACA GAC TTG    2112
PHE ILE ASP ARG LYS THR PRO ASN ASN PRO SER CYS ASN THR ASP LEU
            665             670             675

ATT AAT AGA GTC TTG CTG GAT GCA GGC TTT ACA AAT GAA CTT GTT CAA    2160
ILE ASN ARG VAL LEU LEU ASP ALA GLY PHE THR ASN GLU LEU VAL GLN
            680             685             690

AAT TAC TGG AGT AAG CAG AAG AAT ATC AAG GGA GTG AAA GCA CGG TTT    2208
ASN TYR TRP SER LYS GLN LYS ASN ILE LYS GLY VAL LYS ALA ARG PHE
695             700             705             710

GTT GTG ACT GAT GGT GGG ATT ACC AGA GTT TAT CCC AAA GAG GCT GGA    2256
VAL VAL THR ASP GLY GLY ILE THR ARG VAL TYR PRO LYS GLU ALA GLY
            715             720             725

GAA AAT TGG CAG GAA AAC CCA GAG ACA TAT GAA GAC AGC TTC TAT AAA    2304
GLU ASN TRP GLN GLU ASN PRO GLU THR TYR GLU ASP SER PHE TYR LYS
            730             735             740

AGG AGC CTC GAT AAT GAT AAC TAC GTT TTC ACT GCT CCC TAC TTT AAC    2352
ARG SER LEU ASP ASN ASP ASN TYR VAL PHE THR ALA PRO TYR PHE ASN
            745             750             755          *
```

FIGURE 2e

```
AAA AGT GGA CCT GGG GCC TAT GAG TCA GGC ATT ATG GTA AGC AAA GCT   2400
LYS SER GLY PRO GLY ALA TYR GLU SER GLY ILE MET VAL SER LYS ALA
    760                 765                 770

GTA GAA ATA TAT ATC CAA GGA AAA CTT CTT AAA CCT GCA GTT GTT GGA   2448
VAL GLU ILE TYR ILE GLN GLY LYS LEU LEU LYS PRO ALA VAL VAL GLY
775                 780                 785                 790

ATT AAA ATT GAT GTA AAT TCT TGG ATA GAG AAT TTC ACC AAA ACT TCA   2496
ILE LYS ILE ASP VAL ASN SER TRP ILE GLU ASN PHE THR LYS THR SER
                795                 800  *                 805

ATC AGG GAT CCG TGT GCT GGT CCA GTT TGT GAC TGC AAA CGA AAC AGT   2544
ILE ARG ASP PRO CYS ALA GLY PRO VAL CYS ASP CYS LYS ARG ASN SER
            810                 815                 820       P

GAT GTA ATG GAT TGT GTG ATT CTA GAT GAC GGT GGG TTT CTT TTG ATG   2592
ASP VAL MET ASP CYS VAL ILE LEU ASP ASP GLY GLY PHE LEU LEU MET
        825                 830                 835

GCC AAC CAT GAT GAT TAT ACC AAT CAG ATT GGA AGA TTC TTT GGA GAG   2640
ALA ASN HIS ASP ASP TYR THR ASN GLN ILE GLY ARG PHE PHE GLY GLU
    840                 845                 850

ATT GAT CCA AGC TTG ATG AGA CAC CTG GTC AAT ATA TCA GTT TAT GCC   2688
ILE ASP PRO SER LEU MET ARG HIS LEU VAL ASN ILE SER VAL TYR ALA
855                 860                 865                 870
                                         *

TTT AAC AAA TCT TAT GAT TAT CAG TCG GTG TGT GAA CCT GGT GCT GCG   2736
PHE ASN LYS SER TYR ASP TYR GLN SER VAL CYS GLU PRO GLY ALA ALA
    *               875                 880                 885

CCA AAG CAG GGA GCA GGG CAC CGC|TCG GCT TAT GTG CCA TCA ATA GCA   2784
PRO LYS GLN GLY ALA GLY HIS ARG|SER ALA TYR VAL PRO SER ILE ALA
                890             895                 900

GAC ATA CTG CAG ATT GGA TGG TGG GCC ACT GCT GCT GCC TGG TCT ATT   2832
ASP ILE LEU GLN ILE GLY TRP TRP ALA THR ALA ALA ALA TRP SER ILE
        905                 910                 915

CTT|CAG CAG TTT CTG TTG AGT TTG ACT TTT CCA CGG CTC CTT GAG GCA   2880
LEU|GLN GLN PHE LEU LEU SER LEU THR PHE PRO ARG LEU LEU GLU ALA
    920                 925                 930

GCT GAT ATG GAG GAT GAC GAC TTC ACT GCC TCC ATG TCA AAG CAG AGC   2928
ALA ASP MET GLU ASP ASP ASP PHE THR ALA SER MET SER LYS GLN SER
935                 940                 945                 950
```

FIGURE 2f

```
TGC ATC ACT GAG CAA ACC CAG TAT TTC TTC GAT AAT GAC AGC AAA TCG   2976
CYS ILE THR GLU GLN THR GLN TYR PHE PHE ASP ASN ASP SER LYS SER
            955                     960   *         965

TTC AGT GGG GTA TTA GAC TGT GGG AAT TGT TCC AGA ATC TTT CAT GTA   3024
PHE SER GLY VAL LEU ASP CYS GLY ASN CYS SER ARG ILE PHE HIS VAL
            970                     975             980

GAA AAG CTC ATG AAC ACC AAT TTA ATA TTC ATA ATG GTA GAG AGC AAG   3072
GLU LYS LEU MET ASN THR ASN LEU ILE PHE ILE MET VAL GLU SER LYS
        985                     990             995

GGG ACA TGT CCC TGT GAC ACA CGG CTG CTC ATA CAA GCA GAG CAA ACT   3120
GLY THR CYS PRO CYS ASP THR ARG LEU LEU ILE GLN ALA GLU GLN THR
        1000                1005                1010

TCT GAT GGA CCA GAT CCT TGT GAT ATG GTT AAG CAA CCC AGA TAT CGA   3168
SER ASP GLY PRO ASP PRO CYS ASP MET VAL LYS GLN PRO ARG TYR ARG
1015                1020                1025                1030

AAA GGG CCA GAT GTC TGC TTT GAC AAC AAT GTC CTG GAG GAT TAT ACT   3218
LYS GLY PRO ASP VAL CYS PHE ASP ASN ASN VAL LEU GLU ASP TYR THR
                    1035                1040            1045

GAC TGC GGT GGG GTC TCT GGA TTA AAT|CCT TCC CTG TGG TCC ATC ATC   3264
ASP CYS GLY GLY VAL SER GLY LEU ASN|PRO SER LEU TRP SER ILE ILE
            1050                1055                1060
                                  *

GGG ATA CAG TTT GTA CTG CTT TGG CTG GTT TCT GGC AGC|AGA CAC TGC   3312
GLY ILE GLN PHE VAL LEU LEU TRP LEU VAL SER GLY SER|ARG HIS CYS
            1065                1070                1075

CTG TTA TGA CCTTCTAAAA CCAAATCTCC ATAATTAAAC TCCAGACCCT          3361
LEU LEU
        1080

GCCACAACAT GATCCCTCCG TTATGTTAAA GTAGGGTCAA CTGTTAAATC           3411
AGAACATTAG CTGGGCCTCT GCCATGGCAG AGCCCTAAGG CGCAGACTCA           3461
TCAGGCACCC ACTGGCTGCA TGTCAGGGTG TCC ...... 3'                   3494
```

FIGURE 3c

```
AAGTGTTAGTGGATTGACACTTAAACTGATCCGAACATCTGTCTCCGAAA  869
|||  |||||||||  |||||||  |||||  |||||  |||||  ||||||||||||
AAGCGTTAGTGGACTGACACTCAAACTCATCCGGACATCCGTCTCCGAAA  1149

TGTTAGAAACCCTCTCAGATGATGATTTCGTGAATGTAGCTTCATTTAAC  919
||||  |||||||||||||||||||||||||  |||||  ||  ||||||||||||
TGTTGGAAACCCTCTCAGATGATGATTTTGTGAACGTGGCTTCATTTAAC  1199

AGCAATGCTCAGGATGTAAGCTGTTTTCAGCACCTTGTCCAAGCAAATGT  969
||||||||||||||||||||||||  |||||||||||||||||||||||||
AGCAATGCTCAGGATGTAAGCTGCTTTCAGCACCTTGTCCAAGCAAATGT  1249

AAGAAATAAAAAAGTGTTGAAAGACGCGGTGAATAATATCACAGCCAAAG  1019
||||||||  ||||||||||||||  ||  |||||||||||||||||  ||||
AAGAAATAAGAAAGTGTTGAAAGATGCAGTGAATAATATCACAGCAAAAG  1299

GAATTACAGATTATAAGAAGGGCTTTAGTTTTGCTTTTGAACAGCTGCTT  1069
||||  ||||||||||||||||||||||||||||||||||||||  ||||||
GAATCACAGATTATAAGAAGGGCTTTAGTTTTGCTTTTGAGCAGCTGCTT  1349

AATTATAATGTTTCCAGAGCAAACTGCAATAAGATTATTATGCTATTCAC  1119
||||||||||  ||||||||  ||||||||||||||||  |||  |  |||||
AATTATAATGTATCCAGAGCCAACTGCAATAAGATTATCATGTTGTTCAC  1399

GGA...TGGAGAAGAGAGAGCCCAGGAGATATTTAACAAATACAATAAAG  1166
|||      ||||||||||||||||||||||||||||  ||||||||||||||
GGACGGAGGAGAAGAGAGAGCCCAGGAGATATTTGCCAAATACAATAAAG  1449

ATAAAAAACTACCTGTATTCACCTTCTCAGTTGGTCAACACAATTATGAC  1216
|  ||  |||  |||  ||||||||||  |||||||||||  |||||  ||||||  |||
ACAAGAAAGTACGTGTATTCACATTCTCAGTTGGCCAACATAATTACGAC  1499
```

CELLS EXPRESSING CALCIUM CHANNEL α2 SUBUNIT-ENCODING DNA, OPTIONALLY WITH A REPORTER GENE FOR SCREENING ASSAYS

This application is a continuation of U.S. application Ser. No. 08/314,083, filed 28 Sep. 1994, which is a divisional of U.S. application Ser. No. 07/914,231, filed 13 Jul. 1992, now U.S. Pat. No. 5,407,820, which is a continuation of U.S. application Ser. No. 07/603,751, which was filed on 4 Apr. 1989 as International application Serial No. PCT/US89/01408 and which entered the U.S. national phase under 35 U.S.C. §371 on 8 Nov. 1990 and is now abandoned, which International application is in turn a continuation-in-part of U.S. application Ser. No. 07/176,899, filed on 4 Apr. 1988 and now abandoned. Application Ser. No. 08/314,083 is additionally a divisional of application Ser. No. 07/914,231, to which the present application directly claims priority as indicated above.

A number of compounds useful in treating various diseases in animals, including humans, are thought to exert their beneficial effects by modulating functions of voltage-dependent calcium channels. Many of these compounds bind to calcium channels and block, or reduce the rate of, influx of $Ca^{+2}$ into cells in response to depolarization of the inside and outside of the cells.

An understanding of the pharmacology of compounds that interact with calcium channels, and the ability to rationally design compounds that will interact with calcium channels to have desired therapeutic effects, have been hampered by a lack of understanding of the structure of channel subunits and the genes that code for them. Thus, it has not been possible to obtain the large amounts of highly purified channel subunits that are required to understand, at the molecular level, the nature of the subunits and their interactions with one another, with the cell membranes across which the channels allow $Ca^{+2}$ ions to pass, with $Ca^{+2}$ and other ions, and with low molecular weight compounds that affect channel function. For example, with the availability of large amounts of purified calcium channel subunits, functional channels could be prepared and used to screen the effects of compounds on channel function, thereby providing a basis for the design of therapeutic agents which affect the calcium channel, or various combinations of channel subunits could be crystallized and have their structures determined to high resolution employing X-ray or neutron diffraction techniques, providing yet another basis for rational design of therapeutic agents that affect channel function.

Certain diseases, such as Lambert-Eaton Syndrome, involve autoimmune interactions with calcium channels. The ready availability of calcium channel subunits would make possible immunoassays for the diagnosis of such diseases and an understanding of them at the molecular level that could lead to effective methods for treating them.

The lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunits genes is regulated, may provide the basis for designing therapeutic agents which have beneficial effects through affecting calcium channel function or concentration. Furthermore, the availability of sequences of genes coding for calcium channel subunits would make possible the diagnosis of defects, which might underlie a number of diseases, in genes coding for such subunits.

The availability of a DNA with the sequence of a segment, of at least about 12, and more preferably at least about 30, nucleotides of a cDNA encoding a subunits of a calcium channel from the cells of a tissue of an animal would make possible the isolation and cloning of cDNA's, and possibly genomic DNA's, coding for the corresponding subunits of different calcium channels from the same or different tissues and animals of the same or different species. The availability of the sequences of numerous full-length cDNA's coding for corresponding subunits of calcium channels from a variety of tissues and animal species would contribute to elucidating structure-function relationships in the subunits and this knowledge, in turn, would be useful in the design of therapeutic agents whose activities are exerted through binding to calcium channels.

Voltage-dependent calcium channels are thought to consist of two large subunits, of between about 130 and about 200 kilodaltons ("kD") in molecular weight, and a number (generally thought to be one or three) of different smaller subunits, of less than about 60 kD in molecular weight. At least one of the larger subunits and possibly some of the smaller are glycosylated. Some of the subunits are capable of being phosphorylated. There is confusion in the art concerning the naming of the various subunits of voltage-dependent calcium channels.

The two large subunits of voltage-dependent calcium channels are designated herein the "(alpha)$_1$-subunit" and the "(alpha)$_2$-subunit".

The (alpha)$_1$-subunit is not detectably changed in molecular weight when treated with dithiothreitol ("DTT") or with enzymes which catalyze removal of N-linked sugar groups from glycosylated proteins. The (alpha)$_1$-subunit has a molecular weight of about 150 to about 170 kD when analyzed by sodium dodecylsulfate ("SDS")-polyacrylamide gel electrophresis ("PAGE") after isolation from mammalian muscle tissue and has specific binding sites for various 1,4-dihydropyridines ("DHPs") and phenylalkylamines.

The (alpha)$_2$-subunit is somewhat less well characterized than the (alpha)$_1$-subunit. The molecular weight of the (alpha)$_2$-subunit is at least about 130–150 kD, as determined by SDS-PAGE analysis in the presence of DTT after isolation from mammalian muscle tissue. However, in SDS-PAGE under non-reducing conditions (in the presence of N-ethylmaleimide), the (alpha)$_2$-subunit migrates with a band of about 160–190 kD. It is not known in the art whether the smaller fragment (of about 30 kD), which appears to be released upon reduction, is the product of a gene different from the gene which encodes the 130–150 kD fragment (and, consequently, the two fragments are different subunits of the calcium channel) or whether both fragments are products of the same gene (and, consequently, the (alpha)$_2$-subunit is about 160–190 kD and is split into (at least) two fragments upon reduction). There is evidence that the (alpha)$_2$-subunit, whatever its size, and the corresponding fragment produced under reducing conditions, whether part of the (alpha)$_2$-subunit or not, are glycosylated with at least N-linked sugars and do not have specified binding sites for 1,4-dihydropyridines and phenylalkylamines that are known to bind to the (alpha)$_1$-subunit.

Reference herein to the precursor of an (alpha)$_1$-subunit means the protein with the amino acid sequence corresponding to the sequence of the full-length mRNA which, upon translation, results, ultimately, in (alpha)$_1$-subunit resident as part of a calcium channel in a cell membrane. The precursor protein is converted by various processing steps into the (alpha)$_1$-subunit. The details of the processing between the precursor and the mature (alpha)$_1$-subunit are not clear, but the processing possibly involves phosphorylation and also cleavage of the primary translation product to yield the mature (alpha)$_1$-subunit of the calcium channel.

Similarly, reference herein to the precursor of an (alpha)$_2$-subunit means the protein with the amino acid sequence corresponding to the sequence of the full-length mRNA which, upon translation, results, ultimately, in (alpha)$_2$-subunit resident as part of a calcium channel in a cell membrane. The precursor protein is converted by various processing steps into the (alpha)$_2$-subunit. As with the (alpha)$_1$-subunit, the details of the processing between the precursor and the mature (alpha)$_2$-subunit are not clear, but the processing presumably involves at least removal of a leader sequence (i.e., a signal peptide), glycosylation, and, possibly, cleavage to yield what are now thought to be other subunits of the calcium channel.

The cDNA and corresponding amino acid sequence of the (alpha)$_1$-subunit precursor of a rabbit back skeletal muscle calcium channel has been reported. Tanabe et al., Nature 328, 313–318 (1987).

Calcium channel activity, measured electrophysiologically by voltage-clamp techniques, has been induced in Xenopus laevis oocytes when total mRNA isolated from mammalian brain and cardiac muscle is injected into the oocytes. Also, it has been reported that calcium channel-containing preparations, when reconstituted into lipid bilayers, confer voltage-dependent calcium channel activity on the bilayers.

However, there is no evidence that the (alpha)$_1$-subunit alone or the (alpha)$_2$-subunit alone provides a functional calcium channel in oocytes, lipid bilayers or any other situation. It has been recently reported by Hofmann, et al., Trends in Pharmacolog. Sci. 8, 393–398 (1987) that mRNA prepared using the cDNA of (alpha)$_1$-subunit obtained by Tanabe, et al. was unable to induce calcium channel activity in Xenopus laevis oocytes.

BRIEF DESCRIPTION OF THE FIGURES

FIGS. 1a–1j set forth the nucleotide sequence of the cDNA encoding the (alpha)$_1$-subunit of the rabbit skeletal calcium channel and the amino acid sequence encoded by the 5,619 nucleotide open reading frame, which encodes a sequence of 1,873 amino acids. The 3' non-coding sequence of the cDNA is 234 nucleotides in length, excluding the poly (dA) tract; and contains a consensus polyadenylation signal ATTAAA (nucleotides 5832–5837) 17 nucleotides upstream from the poly (dA) tract.

FIGS. 2a–2f set forth the 3,802 nucleotide and amino acid sequences of the rabbit skeletal calcium channel (alpha)$_2$-subunit. The figures include the nucleotides of the cDNA that encodes the (alpha)$_2$-subunit precursor, including the 308 nucleotides of the 5' untranslated sequence, the 3,318 nucleotide open reading frame and 176 nucleotides of 3' untranslated sequence. The signal peptide of the (alpha)$_2$-subunit is shown as the first 26 negatively numbered amino acids.

FIG. 3 compares the sequences of the DNA encoding the human neuronal (alpha)$_2$-subunit with that encoding the rabbit skeletal (alpha)$_2$-subunit.

DETAILED DESCRIPTION OF THE INVENTION

In short, we have discovered a cDNA which codes for the (alpha)$_1$-subunit of an animal calcium channel (see FIGS. 1a–1j and a cDNA which codes for the (alpha)$_2$-subunit of an animal calcium channel (see FIGS. 2a–2f and Example 4).

Thus in one of its aspects, the invention is a DNA which comprises a cDNA which codes for the (alpha)$_2$-subunit of an animal calcium channel, and the RNA, coding for such a subunit, made upon transcription of such a DNA according to the invention.

In another of its aspects, the invention is a substantially pure (alpha)$_2$-subunit of an animal calcium channel.

By a "substantially pure" subunit or protein is meant a subunit or protein that is sufficiently free of other polypeptide contaminants to be considered homogeneous by SDS-PAGE or to be unambiguously sequenced.

In another of its aspects, the invention entails an eukaryotic cell with an heterologous calcium channel, said cell made by a process comprising administering to said cell a first composition, which consists essentially of a first RNA which is translatable in said cell into the precursor of the (alpha)$_1$-subunit of a calcium channel of an animal of a first species, and a second composition which consists essentially of a second RNA which is translatable in said cell into the precursor of the (alpha)$_2$-subunit of a calcium channel of an animal of a second species, said first and second species being the same or different, provided that at least one of said precursor of said (alpha)$_1$-subunit and said precursor of said (alpha)$_2$-subunit is foreign to said cell. Preferred cells for this purpose are Xenopus laevis oocytes.

In another of its aspects, the invention entails a method for assaying a compound for calcium channel agonist or antagonist activity which comprises electrophysiologically measuring the calcium channel activity of a cell described in the immediately preceeding paragraph when such cell is exposed to a solution of the compound being tested for such activity. For similar methods applied with Xenopus laevis oocytes and acetylcholine receptors, see e.g., Mishina et al. Nature 313, 364 (1985) and, with such oocytes and sodium channels, see Noda et al., Nature 322, 826–828 (1986).

In a further of its aspects, the invention is an eukaryotic cell containing a DNA which comprises a cDNA which can be expressed to make the (alpha)$_2$-subunit of a calcium channel. Such a cell according to the invention can also contain a DNA which comprises a cDNA which can be expressed to make the (alpha)$_1$-subunit of a calcium channel. Preferably, the (alpha)$_2$-subunit or the (alpha)$_1$-subunit made from such a cDNA in such a cell will be foreign to the cell, i.e., will have an amino acid sequence which differs from that of any calcium channel (alpha)$_1$-subunit or (alpha)$_2$-subunit which occurs in a cell of the same type which does not contain a DNA from which the (alpha)$_1$-subunit or the (alpha)$_2$-subunit encoded by such a cDNA is expressed. Preferred among such cells are those of mammalian origin, such as COS cells, NIH3T3 cells, mouse L cells or the like, or those of yeast such as S. cerevisiae or P. pastoris. Methods of making such cells of the invention, by transforming cells with suitable heterologous DNAs, to be maintained in the cell as episomes or (preferably) integrated into chromosomal DNA of the cell, and then culturing transformants or subculturing (or passaging, in the case of mammalian cells) from such a culture or a subculture thereof, are well known to those of ordinary skill.

Among such cells of the invention, the invention entails also an eukaryotic cell with an heterologous calcium channel, said calcium channel made by a process comprising expression of a first cDNA, which codes for the precursor of the (alpha)$_1$-subunit of a calcium channel of an animal of a first species, and a second cDNA, which codes for the precursor of the (alpha)$_2$-subunit of a calcium channel of a second species, said first and second species being the same or different. Usually at least one of said precursor of said (alpha)$_1$-subunit and said precursor of said (alpha)$_2$-subunit is foreign to said cell. Again, preferred among such cells are those of mammalian origin or those of yeast such as S. cerevisiae cells or P. pastoris. In a preferred embodiment, such a cell will also contain another heterologous gene, which comprises a transcriptional control element (e.g., a promoter or promoter/enhancer combination), which is active in said cell and the transcriptional activity of which responds to an ion or molecule capable of entering said cell through a functional calcium channel (e.g., $Ca^{++}$, $Ba^{++}$, $Ca^{++}$ionophores), linked operatively for expression to a structural gene for an indicator protein, such as chloramphenicol acetyltransferase, luciferase or β-galactosidase.

These cells of the invention, which have functional, foreign calcium channels (i.e., functional calcium channels wherein at least one of the (alpha)$_1$-subunit and the (alpha)$_2$-subunit is foreign to the cell) will be useful for, among other purposes, assaying a compound for calcium channel agonist or antagonist activity. First, such a cell can be employed to measure the affinity of such a compound for the functional calcium channel. Secondly, such a cell can be employed to measure electrophysiologically the calcium channel activity in the presence of the compound being tested as well as a ion or molecule, such as $Ca^{++}$or $Ba^{++}$, which is known to be capable of entering the cell through the functional channel. For similar studies which have been carried out with the acetylcholine receptor, see Claudio et al. Science 238 1688–1694 (1987). These methods for assaying a compound for calcium channel agonist or antagonist activity are also part of the present invention.

Such cells according to the invention, in the preferred embodiment, wherein the cell also contains an heterologous gene with a transcriptional control element, which is active in the cell and responsive to an ion or molecule capable of entering the cell through a functional calcium channel and is linked operatively for expression to a structural gene for an indicator protein, can also be employed, in another method according to the invention for assaying a compound for calcium channel agonist or antagonist activity. This method comprises exposing a culture of such cells to a solution of a compound being tested for such activity, together with an ion or molecule, which is capable of entering the cells through a functional calcium channel and affecting the activity of the transcriptional control element controlling transcription of the gene for the indicator protein, and comparing the level of expression, in the cells of the culture, of the gene for the indicator protein with the level of such expression in the cells of another, control culture of such cells.

A "control culture," as clearly understood by the skilled, will be a culture that is, and is treated, substantially the same as the culture exposed to the compound being assayed except that the control culture is not exposed to the compound being assayed. Levels of expression of the genes for the indicator proteins are ascertained readily by the skilled by known methods, which involve measurements of the concentration of indicator protein via assays for detectable compounds produced in reactions catalyzed by the indicator protein.

As indicated above, indicator proteins are enzymes which are active in the cells of the invention and catalyze production of readily detectable compounds (e.g., chromogens, fluorescent compounds).

In a still further aspect, the invention is a method for diagnosing Lambert-Eaton Syndrome in a person by immunoassay which method comprises combining serum from the person with (alpha)$_1$-subunit of a first animal species and (alpha)$_2$-subunit of a second animal species (the same as or different from the first species) and ascertaining whether antibodies in the serum react with one or both of the subunits to a greater extent than antibodies in control serum (e.g., from a person or group of persons known to be free of the Syndrome). Any immunoassay procedure known in the art for detecting antibodies in serum against a given antigen can be employed in the method. Preferably, in the method, both of the (alpha) subunits are from a mammalian calcium channel, most preferably human.

The invention entails also a labeled (e.g., $^{32}$P or a biotinylated) RNA or single-stranded DNA of at least 12 (preferably at least 30) bases in length in a sequence which comprises a sequence of at least 12 (preferably at least 30) contiguous bases between bases −238 and 3495, inclusive, in FIGS. 2a–2f below, or such a labeled RNA or single-stranded DNA with a sequence taken from the cDNA, described in Example 4, which encodes an human neuronal (alpha)$_2$-subunit. The use of such DNAs and RNAs as probes, to identify and isolate cDNAs coding calcium channel (alpha)$_2$-subunits or to identify tissue in which (alpha)$_2$-subunit mRNA is made, is clear to the skilled. In this regard, see, e.g., Example 4.

The primary strategy for cloning cDNAs encoding the (alpha)$_1$ and the (alpha)$_2$ polypeptide subunits of the DHP-sensitive calcium channels from rabbit skeletal muscle was to screen rabbit back skeletal muscle lambda gt11 cDNA expression libraries with antibody probes specific to each of the proteins. See generally Ausubel et al. Current Protocols in Molecular Biology, Wiley-interscience, New York (1987); Davis et al. Basic Methods in Molecular Biology, Elsevier Science Publishing Co., New York (1986). Monoclonal antibodies capable of immunoprecipitating the $M_r$ 155K–170K DHP receptor (alpha)$_1$ protein from rabbit skeletal muscle triads have been described previously by Leung, et al. J. Biol. Chem. 262, 7943–7946 (1987). Polyclonal antisera specific for the (alpha)$_2$ polypeptide subunit was prepared in guinea pigs using SDS polyacrylamide gel purified (alpha)$_2$ protein as described by Nakayama, et al. J. Biol. Chem. 262, 6572–6576 (1987). One of the (alpha)$_1$-specific monoclonal antibodies, designated as IIF7 by Leung, et al. supra, and the (alpha)$_2$-specific polyclonal antisera were used for screening of 1.0×10$^6$ recombinant phages of an oligo-dT primed lambda gt11 cDNA library. Probes based on the Tanabe et al. (alpha)$_1$-subunit cDNA sequence (Nature 328, 313–318 (1987)) could also be used to identify clones with fragments of the (alpha)$_1$-subunit cDNA.

Once a positive clone was found using an antibody-screening method, the clone was used to screen further for overlapping clones. A sequential series of overlapping clones was thus generated. These clones were sequenced and fragments were subcloned into either pIBI 24/25 (IBI, New Haven, Conn.) or M13 mp18/19. In cloning the (alpha)$_1$-subunit, the DNA sequence was compared to the primary sequence of the DHP receptor (alpha)$_1$-subunit reported by Tanabe et al. Nucleotide differences resulting in amino acid differences were confirmed by sequencing in both directions.

As pertains to the (alpha)$_1$-subunit, initially, two cDNA clones which reacted positively with the IIF7 monoclonal antibody were isolated and found to be related by cross-hybridization.

DNA sequencing of one of these clones revealed the presence of a cDNA insert of 453 base pairs (bp). Significantly, this insert coded for a 151 amino acid open reading frame with 28% homology to a region for the Electrophorus electroplax sodium channel sequence. The cDNA insert derived from this clone was used to rescreen the lambda gt11 cDNA library and a rabbit back skeletal muscle Okayama-Berg cDNA library (MacLennan, et al., Nature 316, 696–700 (1985)) to isolate overlapping cDNA clones. The cDNA clones were analyzed using the dideoxy chain-termination method of Sanger to determine the entire coding sequence of the (alpha)$_1$ subunit of the calcium channel and a restriction map was made for comparison and orientation of DNA sequences.

An oligo-dT-primed expression cDNA library was constructed in lambda gt11, using young adult rabbit back skeletal muscle poly (A+) RNA (kindly provided by J. Robbins, University of Cincinnati) isolated in guanidine isothiocyanate (see Gubler, et al. Gene 25, 263–269 (1983); Lapeyre, et al., Gene 37, 215–220 (1985); Huynh et. al, DNA Cloning: A Practical Approach, Vol. I 49–78 (IRL, Oxford, 1985)). Double-strand cDNA was synthesized and EcoRI adapters were added. After the addition of the adapters, the double-strand cDNA was size-selected on a Sepharose CL-4B or Bio-Gel A-50m column. Fragments>1500 bp were ligated into EcoRI digested, dephosphorylated lambda gt11. The library was packaged in vitro with Gigapack-plus, (Stratagene, San Diego, Calif.) and an efficiency of>95% recombinants was determined by plating in the presence of X-gal and IPTG. Two clones of a total 1×10$^6$ recombinants were identified by screening the expression library with monoclonal Ab IIF7 reactive with the M$_r$ 170,000 (alpha)$_1$ subunit of the rabbit skeletal muscle calcium channel. Positive plaques were visualized by binding HRP-goat anti-mouse IgG followed by color development with 4-chloro-1-naphthol. Each clone contained a ~500 bp insert and was related by cross-hybridization. One clone was DNA sequenced to identify an open reading frame (nts 2847–3300) and was used to identify a 6.5 Kb transcript by Northern analysis. The 453 bp insert noted above was used to rescreen the lambda gt11 library and 8 of 1×10$^6$ clones were positive. One clone (1700 bp) extended the farthest 5' to nt 2237: its 522 bp PstI fragment, nts 2294–2816, was used to screen 1×10$^6$ transformants of a rabbit back skeletal muscle cDNA library constructed according to the method of Okayama and Berg (see MacLennan, et. al., Nature 316, 696–700 (1985)). Three positive clones were isolated, of which the largest (5.0 Kb) extended 5' to nt −750. The Okayama-Berg cDNA library was rescreened with a 5' 250 bp (PstI)-EcoRI fragment (the PstI site is donated by the Okayama-Berg vector) (nts −750–1006). The longest clone isolated, of 5 positives, was 5.3 Kb, extending 5' to nt −450. To clone the 5' end of (alpha)$_1$, a random primed rabbit back skeletal muscle lambda gt11 cDNA library was synthesized as described above with the following modifications: (1) pd(N)$_6$ hexamers (Pharmacia, Inc. Piscathaway, N.J.) were used to random prime the first strand cDNA reaction, (2) Adapters containing NcoI, KpnI, and EcoRI sites:

5'-CCATGGTACCTTCGTTGACG-3'

3'-GGTACCATGGAAGCAACTGCTTAA-5' were ligated to the double-strand cDNA as described above, and (3) the double-strand cDNA was size-selected on a 1 ml Bio-Gel A50m column. Fragments>600 bp were ligated into lambda gt11. 1×10$^6$ recombinants of this library were screened in duplicate with the 1,648 bp EcoRI/XhoI fragment corresponding to nt 1006–2653 and an oligonucleotide probe spanning the initiating methionine: 5'-GGGAAGC-CATGGAGCCATCCTCACCCCAGG-3'. Forty clones were positive with both probes, of which one (1.55 Kb) extended 78 nts 5' of the start codon and −450 bp 3' of the EcoRI site.

FIGS. 1a–1j show the 5,975 nucleotide sequence of the cDNA encoding the (alpha)$_1$-subunit. There is a 5,619 nucleotide sequence reading frame which encodes a sequence of 1,873 amino acids (FIGS. 1a–1j). The sequence context of the designated initiation codon is consistent with the proposed consensus sequence of Kozak, Nucleic Acids Res. 15, 8125–8132 (1987). The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract. This cDNA sequence is consistent with an −6,500 nucleotide DHP receptor (alpha)$_1$ mRNA. Furthermore, the DNA sequence is 99.4% identical to the cDNA sequence encoding the DHP receptor reported by Tanabe, et. al., supra. Nucleotide differences were identified at 33 positions, of which three, nucleotides 5423, 5444 and 5504 also result in amino acid changes.

As pertains to the (alpha)$_2$-subunit, in an initial screen with the guinea pig (alpha)$_2$-specific polyclonal antisera, three cDNA clones were isolated and shown to be related to each other but not any (alpha)$_1$ cDNA sequences by cross-hybridization. Two of these cDNA clones were used to rescreen the lambda gt11 cDNA library to isolate overlapping cDNA clones. The cDNA clones were analyzed to establish the coding DNA sequence of the (alpha)$_2$ subunit of the calcium channel and a restriction map was made. Approximately 7,850 nucleotides of (alpha)$_2$ cDNA was cloned, which is consistent with an −8,000 nucleotide (alpha)$_2$ mRNA.

An oligo-dT-primed expression cDNA library was constructed in lambda gt11, using young adult rabbit back skeletal muscle poly (A+) RNA as described for the (alpha) 1-subunit. Double-stranded cDNA fragments>1500 bp were ligated into lambda gt11 and a primary plating of 1×10$^6$ recombinants was screened with guinea pig anti-160 Kd (alpha)$_2$ polyclonal anti-sera. Three positive plaques were visualized by binding HRP-Protein A, followed by color development with 4-chloro-1-naphthol. Two clones, (2.5 Kb and 3.6 Kb) overlapped to encode 4.75 Kb of an −8 Kb transcript identified by Northern analysis. (alpha)$_2$ cDNA clones extending in the 5' and 3' direction (oriented by DNA sequencing and identification of a long open reading frame) were isolated by rescreening the same lambda gt11 cDNA library with the (EcoRI)-HindIII fragment of one clone (nts 43–272, 5' proximal; EcoRI site from adapter) or the EcoRI-(EcoRI) fragment of a second clone (−1.0 Kb in the 3' untranslated region). A total of 14 clones were isolated, seven from each end, of which an overlapping pair of clones (one extending −2,750 nts 3' and the other extending 350 nts 5') encoded −7850 nts of the (alpha)$_2$ transcript; 308 nts of 5' untranslated sequence, 3318 nts of coding sequence, and −4224 nts of 3' untranslated sequence. Only 176 nts of 3' untranslated sequence was confirmed in both directions and is reported.

FIGS. 2a–2f represent the 3,802 nucleotides of the cDNA sequence encoding the (alpha)$_2$-subunit and its precursor, including 308 nucleotides of 5' untranslated sequence, a 3,318 nucleotide open reading frame, and 176 nucleotides of 3' untranslated sequence.

FIGS. 2a–2f also show the signal peptide of the (alpha)$_2$-subunit, shown as the first 26 negatively numbered amino acids. An arrow identifies the cleavage site between the signal peptide and the mature (alpha)$_2$-subunit. The N-terminal amino acid sequence previously determined is shown in bold sequence (Thr(+8), Trp(+12), and Asp(+14) were not previously determined.) The nucleotide sequence shown was determined from two clones which overlapped to span the coding sequence of the (alpha)$_2$-subunit. Five nucleotide differences among individual clones were observed resulting in four amino acid changes. Differences occurred in the sequence at positions 169, 347, 348, 984, and a deletion of nts 1858–1860. The amino acids were finally determined to be as follows: Asn at residue 31, Lys at residue 90, and a deletion of Ser at residue 594. An in-frame upstream stop codon is underlined as well as the start and stop codons of an upstream short open reading frame. Three putative transmembrane regions are enclosed in boxes. Potential N-glycosylation and phosphorylation sites are indicated as described for FIGS. 1a–1j.

The open reading frame encodes a sequence of 1,106 amino acids (FIGS. 2a–2f). The previously determined NH$_2$-terminal amino acid sequence of the (alpha)$_2$ protein is encoded by nucleotides 79–129 in the same open reading frame (amino acid residues 1–17. FIGS. 2a–2f). The nucleotide sequence adjacent to the designated initiating codon agrees with the proposed consensus sequence. An in-frame termination codon is present upstream beginning at nucleotide −27. In addition, an out-of-frame potential initiation codon is located beginning at nucleotide −229 and is followed by a nonsense codon at nucleotides −179 to −181. The 5' untranslated sequence of the (alpha)$_2$ cDNA, 308 nucleotides cloned and sequenced thus far, is unusually long. This region is extremely G+C rich, approximately 80% G+C, which is similar to other relatively long 5' non-coding sequences which have been reported.

FIGS. 1a–1j show the 1,873 amino acid sequence deduced from the cDNA of the (alpha)$_1$ subunit of the rabbit skeletal muscle calcium channel. Based on the identification of a clone using the (alpha)$_1$-specific IIF7 monoclonal antibody, we have determined that the protein sequence encoded by the 453 bp cDNA insert (amino acid residues 950—1,100) contains the epitope recognized by this monoclonal antibody. The complete sequence yields a calculated Mr of 212,143 for the (alpha)$_1$ protein, in contrast to the observed Mr 155K–170K, previously reported by others using SDS polyacrylamide gel electrophoresis. The amino acid sequence determined and reported here is 99.8% identical to that recently described by Tanabe et al., supra, showing three amino acid differences at residues 1,808 (Thr to Met), 1,815 (Ala to Val), and 1,835 (Ala to Glu). The calcium channel (alpha)$_1$-subunit protein contains five potential N-glycosylation sites at Asn residues 79, 257, 797, 1,464, and 1,674 and seven potential cAMP-dependent phosphorylation sites at Ser residues 687, 1,502, 1,575, 1,757, 1,772, and 1,854, and Thr 1,552. Analogous to the (alpha)-subunit of the sodium channel, the (alpha)$_1$-subunit of the skeletal muscle calcium channel contains four internal repeated sequence regions. An analysis of the hydropathy profile of the (alpha)$_1$-protein sequence reveals that each repeat contains five hydrophobic segments and one segment with strong positive charge. Since the (alpha)$_1$-protein sequence lacks an hydrophobic amino-terminal sequence characteristic of a signal peptide, it has been proposed that the segments of the four internally repeated regions represent twenty-four transmembrane segments and that the amino-and carboxy-termini extend intracellularly. That model is consistent with two of the potential glycosylation sites (Asn residues 79 and 257) being localized extracellularly and all of the potential phosphorylation cites being localized intracellularly. This generally agrees with previous biochemical studies suggesting that the (alpha)$_1$-subunit (which has been identified as the putative 1,4-dihydropyridine receptor) is not glycosylated but is phosphorylated.

FIGS. 2a–2f show the 1,106 amino acid sequence deduced from the cDNA of the (alpha)$_2$-subunit of the rabbit skeletal muscle calcium channel. The sequence yields a calculated $M_r$ of 125,018 for this protein, in contrast to the observed $M_r$ 165K–175K (under non-reducing conditions; $M_r$ 135K–150K under reducing conditions) determined previously by SDS polyacrylamide gel electrophoresis. The (alpha)$_2$ amino acid sequence deduced here from the cDNA confirms the sequence of 17 amino acids reported earlier as supposedly that of the amino terminal 17 amino acids of the (alpha)$_2$-subunit. The (alpha)$_2$-subunit precursor has a 26 amino acid (residues −1 to −26) signal peptide. While this proposed signal peptide is hydrophobic and of an appropriate length characteristic of signal sequences, it is somewhat unusual in that the peptide has Glu at position-1 and the Gln at position-12 defines a rather short central hydrophic region. The (alpha)$_2$ protein contains 18 potential N-glycosylation sites (Asn residues 68, 112, 160, 300, 324, 444, 451, 580, 589, 652, 671, 758, 801, 865, 872, 962, 975, and 1,005) and two potential cAMP-dependent phosphorylation sites at Thr 477 and Ser 822 (FIGS. 2a–2f).

An analysis of the (alpha)$_2$ protein sequence for regional hydropathy reveals that, in distinct contrast to similar analysis of the (alpha)$_1$ protein, this protein is substantially hydrophilic, although it does contain a number of hydrophobic regions. Further characterization of the hydrophobic regions of polarity index and hydrophobic moment analyses indicates that three segments may represent transmembrane domains of the (alpha)$_2$ protein. The topography of the (alpha)$_2$ protein is not, however, easily predicted from the deduced primary amino acid sequence. This problem is further compounded by the determination that the (alpha)$_2$ protein lacks significant homology with any protein in the Dayhoff protein sequence database or with other known ion channel and receptor proteins. If the proposed (alpha)$_2$ signal sequence is, in fact, cleaved between the Glu-residue at position −1 and the Glu residue at position, then the amino terminus of the mature protein would be extracellular. Furthermore, assuming that the three hydrophobic segments function as transmembrane domains, and that there are only three such domains, the carboxyl-terminus of the (alpha)$_2$ protein would be intracellular. Such a transmembrane topography would be consistent with 8 out of 18 potential N-glycosylation sites being localized extracellularly and the single potential phosphorylation site being localized intracellularly. Previous biochemical studies indicate that the (alpha)$_2$-subunit of the skeletal muscle calcium channel is not phosphorylated but is extensively glycosylated.

Rabbit and human genomic DNAs were digested with various restriction enzymes and Southern blots of these DNAs were hybridized with radiolabeled cDNA clones specific for the (alpha)$_1$-subunit or the (alpha)$_2$-subunit. Under conditions of high stringency, very few hybridizing bands were observed in rabbit genomic DNA with either the (alpha)$_1$- or (alpha)$_2$-specific probes. This result is consistent with a low-copy number, perhaps only a single-copy, of each of the (alpha)$_1$- and (alpha)$_2$-subunit genes in the rabbit genome. Southern blot of the same DNA preparations were also probed under conditions of low stringency with the same (alpha)$_1$- and (alpha)$_2$-specific probes. While additional hybridizing bands were observed in rabbit genomic DNA under low stringency conditions with both the (alpha)$_1$- and (alpha)$_2$-specific probes, substantially greater hybridization was observed with the (alpha)$_1$-specific cDNA probes. These results suggest that the (alpha)$_1$- and (alpha)$_2$-subunits of the skeletal muscle DHP-sensitive calcium channel may share significant homology with genes encoding other voltage-dependent DHP-sensitive calcium channels, voltage-dependent calcium channels which are not DHP-sensitive (e.g., T- and N-types), and possibly ligand-gated calcium channels (e.g., glutamate receptor). Interestingly, hybridization bands were observed in human genomic DNA with the (alpha)$_1$-specific cDNA probes under both high and low stringency conditions, whereas significant hybridization of (alpha)$_2$-specific cDNA probes were observed only under low stringency conditions. Thus, while there are human genes homologous to the rabbit (alpha)$_1$- and (alpha)$_2$-subunit genes, greater evolutionary sequence divergence may have occurred in the (alpha)$_2$ gene relative to the (alpha)$_1$ gene.

A further aspect of the invention provides for a diagnostic assay for Lambert Eaton Syndrome (LES). LES is an autoimmune disease characterized by an insufficient release of acetylcholine from motor nerve terminals which normally are responsive to nerve impulses. A recent publication (Kim and Neher, Science 239, 405–408 (1988)) demonstrates that IgG from LES patients block individual voltage-dependent calcium channels and thus prevent function. A diagnostic assay for LES based on immunological reactivity of LES IgG with calcium channel (alpha)$_2$-subunit alone or in combination with (alpha)$_1$-subunit is thus provided for. For example, such an assay may be based on immunoprecipitation of LES IgG by the calcium channels subunits of the invention.

EXAMPLE 1

Isolation of RNA for cDNA Library

On the day before RNA is isolated, prepare the following. As a precaution, all glassware should be baked and all stock solutions in the list immediately below should be sterilized by autoclaving.
200 ml of 0.1 NaOAc, pH 5.2, 1 mM EDTA
50 ml of 0.2M Na$_2$ EDTA, pH 8.0.
50 ml of 1M Tris, pH 7.5
50 ml of 3.2 Tris, pH 7.2
50 ml of 0.01M Tris (pH 8.0), 1 mM EDTA
50 ml PK buffer (0.1M Tris, pH 7.2, 50 mM NaCl, 10 mM EDTA)
50 ml of 10% SDS,
4 l of ultrapure H$_2$O
On the morning of the RNA isolation, combine:
100 ml H$_2$O
100 g guanidine isothiocyanate (IBI)
10.6 ml 1M Tris, pH 7.5
10.6 ml 0.2M EDTA
Stir, but do not heat above 65° C. to dissolve guanidine isothiocyanate.

Dissect young adult rabbit back skeletal muscle on a clean glass plate and add about 10 g of muscle tissue (cut in ~4 mm pieces) to 50 ml of the guanidine isothiocyanate solution in e.g., a 100 ml Wheaton bottle.

Homogenize using "tissuemizer" from Tekman (large blade) for 10–20 sec., or until small pieces are no longer visible.

Place in 60° H$_2$O bath, add 30 ml of redistilled phenol which has been made 0.1% in 8-OH quinoline, 0.2% B-ME. Solution should be clear and homogenous after this addition.

Add 30 ml of a 1:1 solution of chloroform:acetate buffer.

Shake vigorously at 60° for 10 minutes; the solutions should appear opaque; if not, add sufficient chloroform:acetate until it turns milky.

Cool on ice, spin to separate phases (7000×g, 10–20 minutes)

Take off and pass it vigorously through a 22 gauge needle.

Treat with phenol:chloroform (1:1) saturated with acetate buffer. Extract aqueous layer with 3× volume of chloroform. Add 2 vol of −20° EtOH, and ppt for 1–2 hours, but no longer.

Collect precipitate; dry briefly (<5 minutes) under vacuum. Resuspend in 7 ml of PK buffer made 0.2% with respect to SDS. If precipitate develops, heat at 65° until solution clears. Add 1.5 mg of proteinase K.

Incubate 20 minutes at 37° (if you have dried for too long, RNA will be very difficult to get into solution and vigorous pipetting will be necessary throughout the incubation).

Extract reaction with 1:1 phenol:chloroform (made 0.1% in 8-OH quinoline, 0.2% B-ME, saturate with 100 mM Tris, pH 8.5 or PK buffer pH 7.7), 2× with chloroform, ppt by addition of 1/10 volume of 3.2M Tris, pH 7.5 and 2 vol. of EtOH. Poly A$^+$ RNA may then be isolated from the RNA mixture by well-known hybridization methods utilizing matrix-immobilized oligo (dT).

EXAMPLE 2 cDNA Cloning Procedure

1. First Strand Synthesis a. The following reagents and compositions are combined together and incubated on ice for 5 minutes:

| Reagent | Volume | Final concentration |
|---|---|---|
| ~5 µg poly A + RNA, plus water | to 10.5 µl | |
| 5X reverse transcriptase buffer | 10 µl | 1X |
| 0.5M DTT | 1 µl | 10 mM |
| RNasin (24 U/µl) | 2 µl | ~1U/µl |
| 5X dNTPs | 10 µl | 1X |
| oligo dT (250 µg/ml) | 5 µl | 25 µg/ml | b. Next, the following three reagents are added to (a) and the mixture is incubated at 37° C. for 60 minutes:

| | | |
|---|---|---|
| actinomycin D (600 µg/ml) | 4 µl | ~50 µg/ml |
| $^{32}$P-gammadCTP (3200 Ci/mmol) | 2.5 µl | — |
| MMLV-reverse transcriptase (BRL-200 U/µl) | 5 µl | 200 U/µg RNA |
| | 50 µl (total a + b) | | c. The following reagents are added to (b) and the mixture is incubated at 37° C. for 30 minutes:

| | |
|---|---|
| RNasin (24 U/µl) | 1 µl |
| MMLV-reverse transcriptase (BRL-200 U/µl) | 3 µl | d. Take aliquots for analysis:
1 µl at time 0 for TCA
1 µl at 90 minutes for TCA
0.5 µl at 90 minutes for gel e. The reaction is stopped after 30 minutes by adding 2 µl of 0.5M EDTA and performing one phenol/chloroform extraction, followed by one chloroform extraction. Then 10 µl of 10M NH$_4$OAc plus two volumes of ethanol are added to precipitate the first strand.

f. To analyze the synthesis, 0.5 µl of the reaction are run on a 1.5% agarose mini-gel, the gel is photographed, dried, and placed under film (generally an overnight exposure with an intensifying screen is adequate).

g. Calculate the mass of cDNA from the percent incorporation of label above background. 1 µg ss cDNA=1.4% incorporation.

2. Second Strand Synthesis a. The cDNA-RNA is spun down by centrifugation in a benchtop microfuge for 15 minutes. The pellet is washed in 95% ethanol and dried.

b. The following mixture is assembled and incubated at 12° C. for 60 minutes.

|  | Volume | Final Concentration |
|---|---|---|
| cDNA RNA, plus water | to 68 µl |  |
| 5X 2nd strand buffer | 20 µl | 1X |
| 10 mM B-NAD | 1.5 µl | 0.15 mM |
| 4 mM dNTPs | 5 µl | 200 µM/ml |
| DNA polymerase I (10 U/µl) | 2.5 µl | 250 U/ml |
| E. coli DNA ligase (2 U/µl) | 2 µl | 40 U/ml |
| RNase H (2.3 U/µl) | 1 µl | 23 U/ml |
|  | 100 µl |  | c. To this mix is added the following, and incubation continues at 22° C. for 60 minutes:

| DNA polymerase I (10 U/µl) | 1.5 µl |
|---|---|
| E. coli DNA ligase (2 U/µl) | 1.5 µl | d. The reaction is stopped after 60 minutes by adding 4 µl of 0.5M EDTA and performing one phenol/chloroform extraction and one chloroform extraction.

e. The aqueous phase is run over a G-50 column in a short Pasteur pipet and 100 µl fractions are collected. The 500 µls containing the cDNA is collected and pooled, and butanol extracted down to a volume of ~50 µl. The cDNA is precipitated by adding 10 µl of 10M NH$_4$OAc plus two volumes of ethanol.

3. T4 Polymerase Reaction a. The cDNA is spun down in a microfuge for 15 minutes. A 95% ethanol wash is performed and the cDNA pellet is dried. The dry pellet is counted in a scintillation counter. Assume 100% efficiency of the 2nd strand reaction, and calculate mass of double-stranded cDNA from the first strand calculation.

b. To the cDNA is added the following, and the mixture is incubated at 37° C. for 20 minutes.

| cDNA | + |
|---|---|
| 10X T4 buffer | 5 µl |
| H$_2$O | 40.75 µl |
| 4mM dNTPs | 1.25 µl |
| 0.1 mM DTT | 2.5 µl |
| T4 polymerase (10 U/µl) | 0.5 µl |
|  | 50 µl | c. Aliquots are taken:
0.5 µl for gel at time 0
0.5 µl for gel at 20 minutes d. The reaction is stopped after 20 minutes by adding 2 µl of 0.5M EDTA, followed by a phenol/chloroform extraction and a chloroform extraction.

e. The aqueous phase is run over a G-50 column in a short Pasteur pipet and 100 µl fractions are collected. The 500 µls containing the cDNA is collected and pooled, and butanol extracted down to a volume of ~50 µl. The cDNA is precipitated by adding 10 µl of 10M NH$_4$OAc plus two volumes of ethanol.

f. The 0.5 µl samples taken at time 0 and 20 minutes are run on a 1.5% agarose mini-gel, which is subsequently photographed, dried, and placed under film.

4. Addition of EcoRI Adapters (for insertion into lambda gt11)

a. Oligos are synthesized having the following sequences:

20 mer: 5'-CCATGGTACCTTCGTTGACG-3'

24 mer: 3'-GGTACCATGGAAGCAACTGCTTAA-5' b. The 20 mer is phosphorylated by combining the following reagents and incubated at 37° C. for 15 minutes.:

| 225 pmoles 20 mer | + |
|---|---|
| water | 6.8 µl |
| 10X kinase buffer | 1.2 µl |
| $^{32}$P-gammaATP (7000 Ci/mmole) | 1.0 µl |
| kinase (2 U/µl) | 1.0 µl |
|  | 10 µl | c. The following two reagents are added to above mixture and it is incubated at 37° C. for 30 minutes:

| 10 mM ATP | 1 µl |
|---|---|
| kinase (2 U/ml) | 1 µl |
|  | 12 µl (total b + c) | d. The enzyme is then inactivated by boiling for 10 minutes.

e. The 24 mer is hybridized to the phosphorylated 20 mer by addition of 225 pmoles of the 24 mer (plus water to bring volume to 15 µl), and incubation at 65° C. for 5 minutes. The reaction is then allowed to slow cool to room temperature.

The adapters are now present at a concentration of 15 pmoles/µl, and are ready for cDNA-vector ligation.

f. Combine the following:

| cDNA | + |
|---|---|
| hybridized adapters (15 pmol/µl) | 50-fold molar excess over cDNA |
| water | 16 µl |
| 10X ligase buffer | 2 µl |
| ligase (10 U/µl) | 2 µl |
|  | 20 µl |

5. Phosphorylation of cDNA a. The ligase is inactivated by heating the mixture to 72° C. for 15 minutes.

b. The following reagents are added to the cDNA ligation reaction and it is heated at 37° C. for 30 minutes:

| cDNA ligation reaction | 20 μl |
|---|---|
| water | 24 μl |
| 10X kinase buffer | 3 μl |
| 10 mM ATP | 1 μl |
| kinase (2 U/μl) | 2 μl |
| | 50 μl | c. The reaction is stopped by the addition of 2 μl 0.5M EDTA, followed by one phenol/chloroform extraction and one chloroform extraction.

6. Purification and Size-Selection of cDNA a. The cDNA is run over a BIO-GEL A-50 column that has been washed with ≧5 ml of TE buffer. The column has 0.8 ml bed resin in a 0.2 cm (inner diameter)×30 cm siliconized glass tube with a glass wool plug in a yellow pipet tip at the bottom.

b. The cDNA is dried down in a speed vac to −20 μl. 2.5 μl of gel loading dye is added and the cDNA is run over the column. The counts begin coming off after running 200–250 μl TE buffer through the column. 5 minute fractions (−30 μl) are collected and counted in a scintillation counter. Free adapters may begin to elute off 350–400 μl after the cDNA starts to elute.

c. 0.5 μl of several of the collected fractions are run on a 1.5% agarose minigel. The gel is photographed, dried down, and placed under film.

7. Ligation of cDNA to lambda gt11 vector a. The fractions containing cDNA are pooled, butanol extracted down to 20–30 μl, and 5 μl of 10M NH$_4$OAc plus two volumes of ethanol is added to precipitate the cDNA. It is spun in a microfuge for 15 minutes, and then subjected to a 95% ethanol wash and dry.

b. The pellet is counted, and the mass of cDNA is calculated relative to the mass after the second strand synthesis.

c. The cDNA is resuspended in TE (−0.10 pmol/μl).

d. The ligation reaction contains the following, which is incubated at 14°–16° C. overnight:

| lambda gt11 (1 g/μl) | 1 μl |
|---|---|
| cDNA insert | (2–4 fold molar excess of cDNA over vector) |
| water | to 3 μl |
| 5X ligase buffer | 1 μl |
| ligase (10 U/μl) | 1 μl |
| | 5 μl |

8. Packaging

The vector is packaged using the Gigapack in vitro packaging kit supplied by Strategene, and following the instructions contained therein.

| REAGENTS | |
|---|---|
| 5x RT buffer | |
| 250 mM Tris, pH 7.4 | 250 μl of 1M |
| 375 mM KCl | 375 μl of 1M |
| 15 mM MgCl$_2$ | 75 μl of 0.2M |
| H$_2$O | 300 μl |
| | 1000 μl |
| 5X dNTPs | |
| 5 mM dATP | 14.1 μl |
| 3 mM dCTP | 9.1 μl |
| 5 mM dGTP | 13.6 μl |
| 5 mM dTTP | 13.3 μl |
| | 50 μl |
| 5X 2nd Strand Buffer | |
| 100 mM Tris, pH 7.5 | 100 μl of 1M |
| 500 mM KCl | 500 μl of 1M |
| 50 mM (NH$_4$)$_2$SO$_4$ | 50 μl of 1M |
| 25 mM MgCl$_2$ | 125 μl of 0.2M |
| 250 μg/ml BSA | 5 μl of 50 mg/ml |
| water | 220 μl |
| | 1000 μl |
| 10X T4 buffer | |
| 670 mM Tris, pH 8.0 | 670 μl of 1M |
| 167 mM (NH$_4$)$_2$SO$_4$ | 167 μl of 1M |
| 67 mM MgCl$_2$ | 67 μl of 1M |
| H$_2$O | 96 μl |
| | 1000 μl |

EXAMPLE 3

Screening cDNA Library with Antibody

Plate lambda gt11 library on Y1090 in LB agar and 50 μg/ml ampicillin. Grow overnight in 15 ml of LB, 0.2% maltose and 50 μg/ml ampicillin. Pellet the cells and resuspend in 3 ml of 10 mM MgSO$_4$. Plate four plates at 250,000 plaques/plate using 25 μl of phage (10,000/μl) and 300 μl of said 3 ml solution of cells in 10 ml soft agar containing 50 μg/ml ampicillin.

Grow at 42° C. for 2.5 hours and overlay IPTG-treated filters which were soaked in 10 mM IPTG (Boehringer Mannheim Biochemicals, Indianapolis, Ind.). Dry filters until just moist, lay them in the plates and incubate overnight at 37° C.

Orient the plates and spot 0.5 μl of purified DHP receptor on one plate as a positive control. Wash the filters for 10 min at room temperature TBS (50 mM TRIS, 150 mM NaCl, pH 8.0). Wash filters in TBS, 20% FCS (filtered) for 30 min at room temp.

Incubate the filters for 2 hours in TBS, 20% FCS, anti-DHS-receptor antibody (monoclonal or polyclonal). Wash for 10 min in TBS. Transfer filters to new plates and wash for 1 min in TBS, 0.1% NP40. Wash for 10 min in TBS and transfer to new plates.

Incubate for at least 1 hour with TBS, 20% FCS containing an appropriate second antibody (e.g. HRP-Protein A; or HRP-goat anti-mouse IgG).

Wash filters as described above for the first antibody.

Develop the positive clones using about 40 ml/plate of 4-chloro-1-naphthol reagent which is made by dissolving 60 mg of said developer in 20 ml of ice cold MeOH and mixing 4-chloro-1-naphthol (Aldrich Chemical Company, Milwaukee, Wis.) into 100 ml of TBS containing 60 μl of 30% H$_2$O$_2$.

EXAMPLE 4

An Human Neuronal Calcium Channel (Alpha)$_2$-Subunit-Encoding cDNA

Because of the indications, mentioned supra, that human calcium channel (alpha)$_2$-subunit genes had diverged somewhat from rabbit calcium channel (alpha)$_2$-subunit genes, human (alpha)$_2$-subunit-encoding fragments were isolated to use as probes to screen human brain cDNA libraries under high stringency conditions.

Thus, an EcoRI-digested human genomic Southern blot was probed under both low and high stringency conditions with a fragment of rabbit (alpha)$_2$-subunit-encoding cDNA (the fragment from nucleotide 43 to nucleotide 272 indicated in FIGS. 2a–2f). Under low stringency conditions, two genomic fragments were identified, of 3.0 kbp and 3.5 kbp in size. Under high stringency conditions, only the 3.5 kbp fragment maintained a stable hybrid. These two fragments were cloned into lambda-gt11. The 3.5 kbp fragment includes a small PstI-XbaI fragment, of about 300 bp, which includes an 82 bp exon with 96.4% homology to nucleotides 102 to 183 of the sequence in FIGS. 2a–2f. This exon is preceded by the dinucleotide AG (splice donor) and followed by the dinucleotide GT (splice acceptor), as understood in the art. The 3.0 kbp fragment includes an XbaI-BglII fragment, of about 585 bp, which includes 104 bp of an exon (which includes the BglII site at its downstream end) which, in the 104 bp, has 93.3% homology to nucleotides 184 to 287 of the sequence in FIGS. 2a–2f. Both the 300 bp, PstI-XbaI fragment and the 585 bp, XbaI-BglII fragments were used to probe duplicate lifts of a human basal ganglia cDNA library in lambda-gt11 (the library having been obtained from the American Type Culture Collection, Rockville, Md., USA, and containing about 10$^6$ independent recombinants with an average insert size of 800–1000 bp). Three positive clones were identified which hybridized to both probes under high stringency conditions, one with an insert size of about 1150 bp, another with an insert size of about 790 bp, and the third with an insert size of about 670 bp. The 1150 bp insert in the one clone extended into the coding region from about nucleotide 200 in the coding region and was found to have a sequence more than 90% homologous to that of the corresponding segment of the cDNA whose sequence is presented in FIGS. 2a–2f. Using the lambda genome with the 1150 bp insert as probe, an human brain stem cDNA library (also purchased from the American Type Culture Collection, and having about 4×10$^6$ independent recombinants with an average insert size of 800–1000 bp) was probed under high stringency conditions. In this probing, four positive clones were identified, with inserts of about 950 bp, 1120 bp, 3000 bp and 2500 bp. Most of the 1120 bp insert overlapped the 1150 bp insert of the DNA used as probe but extended somewhat upstream from the upstream end of the 1150 bp insert. The 2500 bp insert extended downstream from about 650 bp from the 5'-end of the 1120 bp insert. The DNA with the 2500 bp insert was used to again probe the brain stem library, and a clone with a 2750 bp insert was found. The 2750 bp insert was found by restriction analysis and sequencing to extend in the 3'-direction beyond the translational stop signal of a reading frame that was found to begin in the 1120 bp insert described above. The 2750 bp insert and 1120 bp insert have a PvuII site in common and have been ligated using the PvuII site to provide a cDNA that encodes a human neuronal calcium channel (alpha)$_2$-subunit. The 5'-1560 bp of this cDNA have been sequenced and, as illustrated in FIGS. 3a–3d, found to be 91.2% homologous with the corresponding 1575 bp segment indicated in FIGS. 2a–2f.

The human (alpha)$_2$-subunit-encoding cDNA will be subcloned into the mammalian expression vector pSV2DHFR, which is available in the art, for expression in mammalian tissue culture cells.

We obtained the human neuroblastoma cell line IMR32 from the American Type Culture Collection (accession no. CCL127). A northern blot analysis was carried out on poly A$^+$ RNA from this cell line using the full-length human (alpha)$_2$-subunit-encoding cDNA. Under low stringency washing, a single 8.2 kb fragment was found. The rabbit skeletal muscle (alpha)$_2$-encoding messenger RNA also had a size similar to 8.2 kb. While the invention has been described herein with some specificity, the ordinarily skilled in the art will recognize numerous variations and modifications, in what is described, that are within the spirit of the invention. Such variations and modifications are within the scope of the invention as described in the claims herein.

Various features of the invention are also described in the following claims.

What is claimed is:

1. A eukaryotic cell comprising a heterologous calcium channel, wherein the calcium channel is produced by a process comprising expressing in the cell cDNA that encodes the α₁ subunit of a calcium channel of an animal of a first species, and cDNA that encodes the α₂ subunit of an animal of a second species, wherein:

the first and second species are the same or different; and the cDNA that encodes the α₂ subunit comprises a sequence of nucleotides that encodes the α₂ subunit of a naturally occurring mammalian calcium channel, wherein the sequence of nucleotides hybridizes under conditions of high stringency with DNA that includes all or a portion of the nucleotide sequence set forth in FIGS. 2a to 2f (SEQ ID NO: 2), wherein the portion includes at least nucleotides 43–272 as set forth in FIGS. 2a to 2f.

2. The eukaryotic cell of claim 1, further comprising a heterologous reporter gene, wherein the heterologous reporter gene comprises a transcriptional control element which is active in the cell and the transcriptional activity of which responds to an ion or molecule capable of entering the cell through a functional calcium channel, linked operatively for expression to a structural gene for an indicator protein.

3. The cell of claim 2, wherein the DNA encoding the α₁ subunit encodes a protein having the amino acid sequence set forth in SEQ ID NO: 1 or a protein having an amino acid sequence which is identical to that set forth in SEQ ID NO: 1 except for the presence of a Thr in place of the Met at residue 1,108, an Ala in place of the Val at residue 1,185, and an Ala in place of the Glu at residue 1,835.

4. The cell of claim 2, wherein the indicator protein is selected from the group consisting of chloramphenicol acetyltransferase, luciferase, and β-galactosidase.

5. The cell of claim 3, wherein the indicator protein is selected from the group consisting of chloramphenicol acetyltransferase, luciferase, and β-galatosidase.

* * * * *

UNITED STATES PATENT AND TRADEMARK OFFICE

CERTIFICATE OF CORRECTION

PATENT NO.: 5,618,720

Page 1 of 2

DATED: April 8, 1997

INVENTOR(S): ELLIS, Steven B.; WILLAIMS, Mark E.; HARPOLD, Michael M.; SCWARTZ, Arnold; and BRENNER, Robert It is certified that error appears in the above-identified patent and that said Letters Patent is hereby corrected as shown below:

On the title page: Item [75]
IN THE INVENTORS:
    delete "Jean Sartor"; and
    delete "both of".
IN U.S. PATENT DOCUMENTS:
    Maljanich", the inventor of the U.S. Patent No. 5,424,218, should read —Miljanich—.
IN OTHER PUBLICATIONS:
    on page 1, "Green berg" should read —Greenberg—.
IN THE ABSTRACT:
    at line 1, delete "[DNAs]";
    at line 2, "a$_1$" should be —$\alpha_1$—;
    at line 2, "a$_2$" should be —$\alpha_2$—; and
    , at line 2, delete "[DNAs]".

at column 1, the first paragraph, at lines 6 to 19, should read:
—This application is a continuation of U.S. application Ser. No. 08/314,083, filed 28 Sep. 1994, and a continuation of U.S. application Ser. No. 07/914,231, filed 13 Jul. 1992, now U.S. Patent 5,407,820. U.S. application Ser. No. 08/314,083 is a divisional of U.S. application Ser. No. 07/914,231. U.S. application Ser. No. 07/914,231 is a continuation of U.S. application Ser. No. 07/603,751, which was filed on 4 Apr. 1989 as International application Serial No. PCT/US89/01408 and which entered the U.S. national phase under 35 U.S.C. §371 on 8 Nov. 1990 and is now abandoned. International application Serial No. PCT/US89/01408 is a continuation-in-part of U.S. application Ser. No. 07/176,899, filed on 4 Apr. 1988 now abandoned.—;

at column 9, line 43, "Mr" should read —M$_r$—; and
    at column 11, line 13, "were" should read —was—.

UNITED STATES PATENT AND TRADEMARK OFFICE

CERTIFICATE OF CORRECTION

PATENT NO.: 5,618,720

DATED: April 8, 1997

INVENTOR(S): ELLIS, Steven B.; WILLAIMS, Mark E.; HARPOLD, Michael M.; SCWARTZ, Arnold; and BRENNER, Robert It is certified that error appears in the above-identified patent and that said Letters Patent is hereby corrected as
shown below:

IN THE DRAWINGS:
    delete sheet 20, Figure 1h;
    delete sheet 21, Figure 2a;
    delete sheet 22, Figure 2d:
    delete sheet 24, Figure 2f; and
    delete sheet 25, Figure 3c.

Signed and Sealed this

Twenty-third Day of June, 1998

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 5975 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 79...5700
        ( D ) OTHER INFORMATION:

( x i ) SEQUENCE DESCRIPTION: SEQ ID NO:1:

```
GCGGGGAACA  CTGGGGACGC  AGGGAAGAGA  GGGCCGCGGG  GTGGGGAGC   AGCAGGAAGC              60

GCCGTGGCCA  GGGAAGCC ATG GAG CCA TCC TCA CCC CAG GAT GAG GGC CTG                  111
                    Met Glu Pro Ser Ser Pro Gln Asp Glu Gly Leu
```

|   |   |   |   |   |   |   |   |   |   |   |   |   |   |   |   |   |
|---|---|---|---|---|---|---|---|---|---|---|---|---|---|---|---|---|
|   |   |   |   | 1 |   |   |   | 5 |   |   |   |   | 10 |   |   |   |
| AGG | AAG | AAA | CAG | CCC | AAG | AAG | CCC | CTG | CCC | GAG | GTC | CTG | CCC | AGG | CCG | 159 |
| Arg | Lys | Lys | Gln | Pro | Lys | Lys | Pro | Leu | Pro | Glu | Val | Leu | Pro | Arg | Pro |   |
|   |   |   | 15 |   |   |   |   | 20 |   |   |   |   | 25 |   |   |   |
| CCG | CGG | GCT | CTG | TTC | TGC | CTG | ACC | CTG | CAG | AAC | CCG | CTG | AGG | AAG | GCG | 207 |
| Pro | Arg | Ala | Leu | Phe | Cys | Leu | Thr | Leu | Gln | Asn | Pro | Leu | Arg | Lys | Ala |   |
|   |   | 30 |   |   |   |   | 35 |   |   |   |   | 40 |   |   |   |   |
| TGC | ATC | AGC | ATC | GTG | GAA | TGG | AAA | CCC | TTC | GAG | ACC | ATC | ATC | CTG | CTC | 255 |
| Cys | Ile | Ser | Ile | Val | Glu | Trp | Lys | Pro | Phe | Glu | Thr | Ile | Ile | Leu | Leu |   |
|   | 45 |   |   |   |   | 50 |   |   |   |   | 55 |   |   |   |   |   |
| ACC | ATC | TTT | GCC | AAC | TGT | GTG | GCC | CTG | GCC | GTG | TAC | CTG | CCC | ATG | CCC | 303 |
| Thr | Ile | Phe | Ala | Asn | Cys | Val | Ala | Leu | Ala | Val | Tyr | Leu | Pro | Met | Pro |   |
| 60 |   |   |   |   | 65 |   |   |   |   | 70 |   |   |   |   | 75 |   |
| GAG | GAT | GAC | AAC | AAC | TCC | CTG | AAC | CTG | GGC | CTG | GAG | AAG | CTG | GAG | TAC | 351 |
| Glu | Asp | Asp | Asn | Asn | Ser | Leu | Asn | Leu | Gly | Leu | Glu | Lys | Leu | Glu | Tyr |   |
|   |   |   |   | 80 |   |   |   |   | 85 |   |   |   |   | 90 |   |   |
| TTC | TTC | CTC | ACC | GTC | TTC | TCC | ATC | GAA | GCC | GCC | ATG | AAG | ATC | ATC | GCC | 399 |
| Phe | Phe | Leu | Thr | Val | Phe | Ser | Ile | Glu | Ala | Ala | Met | Lys | Ile | Ile | Ala |   |
|   |   |   | 95 |   |   |   |   | 100 |   |   |   |   | 105 |   |   |   |
| TAC | GGC | TTC | CTG | TTC | CAC | CAG | GAC | GCC | TAC | CTG | CGC | AGC | GGC | TGG | AAC | 447 |
| Tyr | Gly | Phe | Leu | Phe | His | Gln | Asp | Ala | Tyr | Leu | Arg | Ser | Gly | Trp | Asn |   |
|   |   | 110 |   |   |   |   | 115 |   |   |   |   | 120 |   |   |   |   |
| GTG | CTG | GAC | TTC | ATC | ATC | GTC | TTC | CTG | GGG | GTC | TTC | ACG | GCG | ATT | CTG | 495 |
| Val | Leu | Asp | Phe | Ile | Ile | Val | Phe | Leu | Gly | Val | Phe | Thr | Ala | Ile | Leu |   |
|   | 125 |   |   |   |   | 130 |   |   |   |   | 135 |   |   |   |   |   |
| GAA | CAG | GTC | AAC | GTC | ATC | CAG | AGC | AAC | ACG | GCC | CCG | ATG | AGC | AGC | AAA | 543 |
| Glu | Gln | Val | Asn | Val | Ile | Gln | Ser | Asn | Thr | Ala | Pro | Met | Ser | Ser | Lys |   |
| 140 |   |   |   |   | 145 |   |   |   |   | 150 |   |   |   |   | 155 |   |
| GGA | GCC | GGC | CTG | GAC | GTC | AAG | GCC | CTG | AGG | GCC | TTC | CGT | GTG | CTC | AGA | 591 |
| Gly | Ala | Gly | Leu | Asp | Val | Lys | Ala | Leu | Arg | Ala | Phe | Arg | Val | Leu | Arg |   |
|   |   |   |   | 160 |   |   |   |   | 165 |   |   |   |   | 170 |   |   |
| CCC | CTC | CGG | CTG | GTG | TCG | GGG | GTG | CCT | AGT | TTG | CAG | GTG | GTC | CTC | AAC | 639 |
| Pro | Leu | Arg | Leu | Val | Ser | Gly | Val | Pro | Ser | Leu | Gln | Val | Val | Leu | Asn |   |
|   |   |   | 175 |   |   |   |   | 180 |   |   |   |   | 185 |   |   |   |
| TCC | ATC | TTC | AAG | GCC | ATG | CTC | CCC | CTG | TTC | CAC | ATC | GCC | CTG | CTC | GTC | 687 |
| Ser | Ile | Phe | Lys | Ala | Met | Leu | Pro | Leu | Phe | His | Ile | Ala | Leu | Leu | Val |   |
|   |   | 190 |   |   |   |   | 195 |   |   |   |   | 200 |   |   |   |   |
| CTC | TTC | ATG | GTC | ATC | ATC | TAC | GCC | ATC | ATC | GGG | CTG | GAG | CTC | TTC | AAG | 735 |
| Leu | Phe | Met | Val | Ile | Ile | Tyr | Ala | Ile | Ile | Gly | Leu | Glu | Leu | Phe | Lys |   |
|   | 205 |   |   |   |   | 210 |   |   |   |   | 215 |   |   |   |   |   |
| GGC | AAG | ATG | CAC | AAG | ACC | TGC | TAC | TAC | ATC | GGG | ACA | GAC | ATC | GTG | GCC | 783 |
| Gly | Lys | Met | His | Lys | Thr | Cys | Tyr | Tyr | Ile | Gly | Thr | Asp | Ile | Val | Ala |   |
| 220 |   |   |   |   | 225 |   |   |   |   | 230 |   |   |   |   | 235 |   |
| ACA | GTG | GAG | AAT | GAG | AAG | CCC | TCG | CCC | TGC | GCT | AGG | ACG | GGC | TCG | GGG | 831 |
| Thr | Val | Glu | Asn | Glu | Lys | Pro | Ser | Pro | Cys | Ala | Arg | Thr | Gly | Ser | Gly |   |
|   |   |   | 240 |   |   |   |   | 245 |   |   |   |   | 250 |   |   |   |
| CGC | CCC | TGC | ACC | ATC | AAC | GGC | AGC | GAG | TGC | CGG | GGC | GGC | TGG | CCG | GGG | 879 |
| Arg | Pro | Cys | Thr | Ile | Asn | Gly | Ser | Glu | Cys | Arg | Gly | Gly | Trp | Pro | Gly |   |
|   |   |   | 255 |   |   |   |   | 260 |   |   |   |   | 265 |   |   |   |
| CCC | AAC | CAC | GGC | ATC | ACG | CAC | TTC | GAC | AAC | TTC | GGC | TTC | TCC | ATG | CTC | 927 |
| Pro | Asn | His | Gly | Ile | Thr | His | Phe | Asp | Asn | Phe | Gly | Phe | Ser | Met | Leu |   |
|   |   | 270 |   |   |   |   | 275 |   |   |   |   | 280 |   |   |   |   |
| ACC | GTG | TAC | CAG | TGC | ATC | ACC | ATG | GAG | GGC | TGG | ACA | GAT | GTC | CTC | TAC | 975 |
| Thr | Val | Tyr | Gln | Cys | Ile | Thr | Met | Glu | Gly | Trp | Thr | Asp | Val | Leu | Tyr |   |
|   | 285 |   |   |   |   | 290 |   |   |   |   | 295 |   |   |   |   |   |
| TGG | GTC | AAC | GAT | GCC | ATC | GGG | AAC | GAG | TGG | CCC | TGG | ATC | TAC | TTT | GTC | 1023 |
| Trp | Val | Asn | Asp | Ala | Ile | Gly | Asn | Glu | Trp | Pro | Trp | Ile | Tyr | Phe | Val |   |
| 300 |   |   |   |   | 305 |   |   |   |   | 310 |   |   |   |   | 315 |   |
| ACT | CTC | ATC | CTG | CTG | GGG | TCC | TTC | TTC | ATC | CTC | AAC | CTG | GTG | CTG | GGC | 1071 |
| Thr | Leu | Ile | Leu | Leu | Gly | Ser | Phe | Phe | Ile | Leu | Asn | Leu | Val | Leu | Gly |   |

|  |  |  |  |  |  |  |  |  |  |  |  |  |  |  |  |
|---|---|---|---|---|---|---|---|---|---|---|---|---|---|---|---|
|  |  |  |  | 320 |  |  |  | 325 |  |  |  | 330 |  |  |  |
| GTC | CTG | AGT | GGG | GAA | TTC | ACC | AAG | GAG | CGG | GAG | AAG | GCC | AAG | TCC | AGG | 1119 |
| Val | Leu | Ser | Gly | Glu | Phe | Thr | Lys | Glu | Arg | Glu | Lys | Ala | Lys | Ser | Arg |
|  |  |  | 335 |  |  |  | 340 |  |  |  |  | 345 |  |  |  |
| GGA | ACC | TTC | CAG | AAG | CTG | CGG | GAG | AAG | CAG | CAG | CTG | GAG | GAG | GAC | CTT | 1167 |
| Gly | Thr | Phe | Gln | Lys | Leu | Arg | Glu | Lys | Gln | Gln | Leu | Glu | Glu | Asp | Leu |
|  |  | 350 |  |  |  |  | 355 |  |  |  |  | 360 |  |  |  |
| CGG | GGC | TAC | ATG | AGC | TGG | ATC | ACG | CAG | GGC | GAG | GTC | ATG | GAC | GTG | GAG | 1215 |
| Arg | Gly | Tyr | Met | Ser | Trp | Ile | Thr | Gln | Gly | Glu | Val | Met | Asp | Val | Glu |
|  | 365 |  |  |  |  | 370 |  |  |  |  | 375 |  |  |  |  |
| GAC | CTG | AGA | GAA | GGA | AAG | CTG | TCC | TTG | GAA | GAG | GGA | GGC | TCC | GAC | ACG | 1263 |
| Asp | Leu | Arg | Glu | Gly | Lys | Leu | Ser | Leu | Glu | Glu | Gly | Gly | Ser | Asp | Thr |
| 380 |  |  |  |  | 385 |  |  |  |  | 390 |  |  |  |  | 395 |
| GAA | AGC | CTG | TAC | GAA | ATC | GAG | GGC | TTG | AAC | AAA | ATC | ATC | CAG | TTC | ATC | 1311 |
| Glu | Ser | Leu | Tyr | Glu | Ile | Glu | Gly | Leu | Asn | Lys | Ile | Ile | Gln | Phe | Ile |
|  |  |  |  | 400 |  |  |  | 405 |  |  |  |  | 410 |  |  |
| CGA | CAC | TGG | AGG | CAG | TGG | AAC | CGT | GTC | TTT | CGC | TGG | AAG | TGC | CAT | GAC | 1359 |
| Arg | His | Trp | Arg | Gln | Trp | Asn | Arg | Val | Phe | Arg | Trp | Lys | Cys | His | Asp |
|  |  |  | 415 |  |  |  |  | 420 |  |  |  |  | 425 |  |  |
| CTG | GTG | AAG | TCG | AGA | GTC | TTC | TAC | TGG | CTG | GTC | ATC | CTG | ATC | GTG | GCC | 1407 |
| Leu | Val | Lys | Ser | Arg | Val | Phe | Tyr | Trp | Leu | Val | Ile | Leu | Ile | Val | Ala |
|  |  | 430 |  |  |  |  | 435 |  |  |  |  | 440 |  |  |  |
| CTC | AAC | ACC | CTG | TCC | ATC | GCC | TCG | GAG | CAC | CAC | AAC | CAG | CCG | CTC | TGG | 1455 |
| Leu | Asn | Thr | Leu | Ser | Ile | Ala | Ser | Glu | His | His | Asn | Gln | Pro | Leu | Trp |
|  | 445 |  |  |  |  | 450 |  |  |  |  | 455 |  |  |  |  |
| CTG | ACC | CAC | TTG | CAA | GAC | ATC | GCC | AAT | CGA | GTG | CTG | CTG | TCA | CTC | TTC | 1503 |
| Leu | Thr | His | Leu | Gln | Asp | Ile | Ala | Asn | Arg | Val | Leu | Leu | Ser | Leu | Phe |
| 460 |  |  |  |  | 465 |  |  |  |  | 470 |  |  |  |  | 475 |
| ACC | ATC | GAG | ATG | CTG | CTG | AAG | ATG | TAC | GGG | CTG | GGC | CTG | CGC | CAG | TAC | 1551 |
| Thr | Ile | Glu | Met | Leu | Leu | Lys | Met | Tyr | Gly | Leu | Gly | Leu | Arg | Gln | Tyr |
|  |  |  |  | 480 |  |  |  | 485 |  |  |  |  | 490 |  |  |
| TTC | ATG | TCC | ATC | TTC | AAC | CGC | TTC | GAC | TGC | TTC | GTG | GTG | TGC | AGC | GGC | 1599 |
| Phe | Met | Ser | Ile | Phe | Asn | Arg | Phe | Asp | Cys | Phe | Val | Val | Cys | Ser | Gly |
|  |  |  | 495 |  |  |  |  | 500 |  |  |  |  | 505 |  |  |
| ATC | CTG | GAG | CTG | CTG | CTG | GTG | GAG | TCG | GGC | GCC | ATG | ACG | CCG | CTG | GGC | 1647 |
| Ile | Leu | Glu | Leu | Leu | Leu | Val | Glu | Ser | Gly | Ala | Met | Thr | Pro | Leu | Gly |
|  |  | 510 |  |  |  |  | 515 |  |  |  |  | 520 |  |  |  |
| ATC | TCC | GTG | TTG | CGC | TGC | ATC | CGC | CTC | CTG | AGG | CTC | TTC | AAG | ATC | ACC | 1695 |
| Ile | Ser | Val | Leu | Arg | Cys | Ile | Arg | Leu | Leu | Arg | Leu | Phe | Lys | Ile | Thr |
|  | 525 |  |  |  |  | 530 |  |  |  |  | 535 |  |  |  |  |
| AAG | TAC | TGG | ACG | TCG | CTC | AGC | AAC | CTG | GTG | GCC | TCC | CTG | CTC | AAC | TCC | 1743 |
| Lys | Tyr | Trp | Thr | Ser | Leu | Ser | Asn | Leu | Val | Ala | Ser | Leu | Leu | Asn | Ser |
| 540 |  |  |  |  | 545 |  |  |  |  | 550 |  |  |  |  | 555 |
| ATC | CGC | TCC | ATC | GCC | TCG | CTG | CTG | CTG | CTC | TTC | CTC | TTC | ATC | ATC | | 1791 |
| Ile | Arg | Ser | Ile | Ala | Ser | Leu | Leu | Leu | Leu | Phe | Leu | Phe | Ile | Ile |
|  |  |  |  | 560 |  |  |  | 565 |  |  |  |  | 570 |  |  |
| ATC | TTC | GCC | CTG | CTG | GGC | ATG | CAG | CTC | TTC | GGG | GGG | CGG | TAC | GAC | TTC | 1839 |
| Ile | Phe | Ala | Leu | Leu | Gly | Met | Gln | Leu | Phe | Gly | Gly | Arg | Tyr | Asp | Phe |
|  |  |  | 575 |  |  |  |  | 580 |  |  |  |  | 585 |  |  |
| GAG | GAC | ACG | GAA | GTG | CGA | CGC | AGC | AAC | TTC | GAC | AAC | TTC | CCC | CAG | GCC | 1887 |
| Glu | Asp | Thr | Glu | Val | Arg | Arg | Ser | Asn | Phe | Asp | Asn | Phe | Pro | Gln | Ala |
|  |  | 590 |  |  |  |  | 595 |  |  |  |  | 600 |  |  |  |
| CTC | ATC | AGC | GTC | TTC | CAG | GTG | CTG | ACG | GGT | GAG | GAC | TGG | AAC | TCC | GTG | 1935 |
| Leu | Ile | Ser | Val | Phe | Gln | Val | Leu | Thr | Gly | Glu | Asp | Trp | Asn | Ser | Val |
|  | 605 |  |  |  |  | 610 |  |  |  |  | 615 |  |  |  |  |
| ATG | TAC | AAC | GGG | ATC | ATG | GCC | TAC | GGA | GGC | CCG | TCC | TAC | CCG | GGC | GTT | 1983 |
| Met | Tyr | Asn | Gly | Ile | Met | Ala | Tyr | Gly | Gly | Pro | Ser | Tyr | Pro | Gly | Val |
| 620 |  |  |  |  | 625 |  |  |  |  | 630 |  |  |  |  | 635 |
| CTC | GTG | TGC | ATC | TAT | TTC | ATC | ATC | CTT | TTT | GTC | TGC | GGC | AAC | TAT | ATC | 2031 |
| Leu | Val | Cys | Ile | Tyr | Phe | Ile | Ile | Leu | Phe | Val | Cys | Gly | Asn | Tyr | Ile |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 640 |     |     |     |     | 645 |     |     |     |     | 650 |     |      |
| CTG | CTG | AAT | GTC | TTC | CTG | GCC | ATC | GCC | GTG | GAC | AAC | CTG | GCC | GAG | GCC | 2079 |
| Leu | Leu | Asn | Val | Phe | Leu | Ala | Ile | Ala | Val | Asp | Asn | Leu | Ala | Glu | Ala |      |
|     |     |     | 655 |     |     |     |     | 660 |     |     |     |     |     | 665 |     |      |
| GAG | AGC | CTG | ACT | TCC | GCG | CAA | AAG | GCC | AAG | GCC | GAG | GAG | AGG | AAA | CGT | 2127 |
| Glu | Ser | Leu | Thr | Ser | Ala | Gln | Lys | Ala | Lys | Ala | Glu | Glu | Arg | Lys | Arg |      |
|     |     | 670 |     |     |     |     | 675 |     |     |     |     | 680 |     |     |     |      |
| AGG | AAG | ATG | TCC | AGG | GGT | CTC | CCT | GAC | AAG | ACG | GAG | GAG | GAG | AAG | TCT | 2175 |
| Arg | Lys | Met | Ser | Arg | Gly | Leu | Pro | Asp | Lys | Thr | Glu | Glu | Glu | Lys | Ser |      |
|     | 685 |     |     |     | 690 |     |     |     |     | 695 |     |     |     |     |     |      |
| GTG | ATG | GCC | AAG | AAG | CTG | GAG | CAG | AAG | CCC | AAG | GGG | GAG | GGC | ATC | CCC | 2223 |
| Val | Met | Ala | Lys | Lys | Leu | Glu | Gln | Lys | Pro | Lys | Gly | Glu | Gly | Ile | Pro |      |
| 700 |     |     |     | 705 |     |     |     |     | 710 |     |     |     |     | 715 |     |      |
| ACC | ACT | GCC | AAG | CTC | AAG | GTC | GAT | GAG | TTC | GAA | TCT | AAC | GTC | AAC | GAG | 2271 |
| Thr | Thr | Ala | Lys | Leu | Lys | Val | Asp | Glu | Phe | Glu | Ser | Asn | Val | Asn | Glu |      |
|     |     |     |     | 720 |     |     |     |     | 725 |     |     |     |     | 730 |     |      |
| GTG | AAG | GAC | CCC | TAC | CCT | TCA | GCT | GAC | TTC | CCA | GGG | GAT | GAT | GAG | GAG | 2319 |
| Val | Lys | Asp | Pro | Tyr | Pro | Ser | Ala | Asp | Phe | Pro | Gly | Asp | Asp | Glu | Glu |      |
|     |     |     | 735 |     |     |     |     | 740 |     |     |     |     | 745 |     |     |      |
| GAC | GAG | CCT | GAG | ATC | CCA | GTG | AGC | CCC | CGA | CCG | CGC | CCG | CTG | GCC | GAG | 2367 |
| Asp | Glu | Pro | Glu | Ile | Pro | Val | Ser | Pro | Arg | Pro | Arg | Pro | Leu | Ala | Glu |      |
|     |     | 750 |     |     |     |     | 755 |     |     |     |     | 760 |     |     |     |      |
| CTG | CAG | CTC | AAA | GAG | AAG | GCA | GTG | CCC | ATC | CCG | GAA | GCC | AGC | TCC | TTC | 2415 |
| Leu | Gln | Leu | Lys | Glu | Lys | Ala | Val | Pro | Ile | Pro | Glu | Ala | Ser | Ser | Phe |      |
| 765 |     |     |     |     | 770 |     |     |     |     | 775 |     |     |     |     |     |      |
| TTC | ATC | TTC | AGT | CCC | ACC | AAT | AAG | GTC | CGT | GTC | CTG | TGT | CAC | CGC | ATC | 2463 |
| Phe | Ile | Phe | Ser | Pro | Thr | Asn | Lys | Val | Arg | Val | Leu | Cys | His | Arg | Ile |      |
| 780 |     |     |     |     | 785 |     |     |     |     | 790 |     |     |     |     | 795 |      |
| GTC | AAC | GCC | ACC | TGG | TTC | ACC | AAC | TTC | ATC | CTG | CTC | TTC | ATC | CTG | CTC | 2511 |
| Val | Asn | Ala | Thr | Trp | Phe | Thr | Asn | Phe | Ile | Leu | Leu | Phe | Ile | Leu | Leu |      |
|     |     |     |     | 800 |     |     |     |     | 805 |     |     |     |     | 810 |     |      |
| AGC | AGT | GCT | GCG | CTG | GCC | GCC | GAG | GAC | CCC | ATC | CGG | GCG | GAG | TCC | GTG | 2559 |
| Ser | Ser | Ala | Ala | Leu | Ala | Ala | Glu | Asp | Pro | Ile | Arg | Ala | Glu | Ser | Val |      |
|     |     |     | 815 |     |     |     |     | 820 |     |     |     |     | 825 |     |     |      |
| AGG | AAT | CAG | ATC | CTT | GGA | TAT | TTT | GAT | ATT | GCC | TTC | ACC | TCT | GTC | TTC | 2607 |
| Arg | Asn | Gln | Ile | Leu | Gly | Tyr | Phe | Asp | Ile | Ala | Phe | Thr | Ser | Val | Phe |      |
|     |     | 830 |     |     |     |     | 835 |     |     |     |     | 840 |     |     |     |      |
| ACT | GTG | GAG | ATT | GTC | CTC | AAG | ATG | ACA | ACC | TAC | GGC | GCC | TTC | CTG | CAC | 2655 |
| Thr | Val | Glu | Ile | Val | Leu | Lys | Met | Thr | Thr | Tyr | Gly | Ala | Phe | Leu | His |      |
|     | 845 |     |     |     |     | 850 |     |     |     |     | 855 |     |     |     |     |      |
| AAG | GGC | TCC | TTC | TGC | CGC | AAC | TAC | TTC | AAC | ATC | CTG | GAC | CTG | CTG | GTG | 2703 |
| Lys | Gly | Ser | Phe | Cys | Arg | Asn | Tyr | Phe | Asn | Ile | Leu | Asp | Leu | Leu | Val |      |
| 860 |     |     |     |     | 865 |     |     |     |     | 870 |     |     |     |     | 875 |      |
| GTG | GCC | GTG | TCT | CTC | ATC | TCC | ATG | GGT | CTC | GAG | TCC | AGC | ACC | ATC | TCC | 2751 |
| Val | Ala | Val | Ser | Leu | Ile | Ser | Met | Gly | Leu | Glu | Ser | Ser | Thr | Ile | Ser |      |
|     |     |     |     | 880 |     |     |     |     | 885 |     |     |     |     | 890 |     |      |
| GTG | GTA | AAG | ATC | CTG | AGA | GTG | CTA | AGG | GTG | CTC | CGG | CCC | CTG | CGA | GCC | 2799 |
| Val | Val | Lys | Ile | Leu | Arg | Val | Leu | Arg | Val | Leu | Arg | Pro | Leu | Arg | Ala |      |
|     |     |     | 895 |     |     |     |     | 900 |     |     |     |     | 905 |     |     |      |
| ATC | AAC | AGA | GCC | AAA | GGG | TTG | AAG | CAC | GTG | GTC | CAG | TGC | GTG | TTC | GTG | 2847 |
| Ile | Asn | Arg | Ala | Lys | Gly | Leu | Lys | His | Val | Val | Gln | Cys | Val | Phe | Val |      |
|     |     | 910 |     |     |     |     | 915 |     |     |     |     | 920 |     |     |     |      |
| GCC | ATC | CGC | ACC | ATC | GGG | AAC | ATC | GTC | CTG | GTC | ACC | ACG | CTC | CTG | CAG | 2895 |
| Ala | Ile | Arg | Thr | Ile | Gly | Asn | Ile | Val | Leu | Val | Thr | Thr | Leu | Leu | Gln |      |
|     | 925 |     |     |     |     | 930 |     |     |     |     | 935 |     |     |     |     |      |
| TTC | ATG | TTC | GCC | TGC | ATC | GGT | GTC | CAG | CTC | TTC | AAG | GGC | AAG | TTC | TTC | 2943 |
| Phe | Met | Phe | Ala | Cys | Ile | Gly | Val | Gln | Leu | Phe | Lys | Gly | Lys | Phe | Phe |      |
| 940 |     |     |     |     | 945 |     |     |     |     | 950 |     |     |     |     | 955 |      |
| AGC | TGC | AAT | GAC | CTA | TCC | AAG | ATG | ACA | GAA | GAG | GAG | TGC | AGG | GGC | TAC | 2991 |
| Ser | Cys | Asn | Asp | Leu | Ser | Lys | Met | Thr | Glu | Glu | Glu | Cys | Arg | Gly | Tyr |      |

|  |  |  |  |  |  |  |  |  |  |  |  |  |  |  |  |
|---|---|---|---|---|---|---|---|---|---|---|---|---|---|---|---|
| | | | | 960 | | | | | 965 | | | | | 970 | |

```
TAC  TAT  GTG  TAC  AAG  GAC  GGG  GAC  CCC  ACG  CAG  ATG  GAG  CTG  CGC  CCC       3039
Tyr  Tyr  Val  Tyr  Lys  Asp  Gly  Asp  Pro  Thr  Gln  Met  Glu  Leu  Arg  Pro
               975                      980                     985

CGC  CAG  TGG  ATA  CAC  AAT  GAC  TTC  CAC  TTT  GAC  AAC  GTG  CTG  TCG  GCC       3087
Arg  Gln  Trp  Ile  His  Asn  Asp  Phe  His  Phe  Asp  Asn  Val  Leu  Ser  Ala
          990                      995                    1000

ATG  ATG  TCG  CTC  TTC  ACG  GTG  TCC  ACC  TTC  GAG  GGA  TGG  CCC  CAG  CTG       3135
Met  Met  Ser  Leu  Phe  Thr  Val  Ser  Thr  Phe  Glu  Gly  Trp  Pro  Gln  Leu
     1005                     1010                    1015

CTG  TAC  AGG  GCC  ATA  GAC  TCC  AAC  GAG  GAG  GAC  ATG  GGC  CCC  GTT  TAC       3183
Leu  Tyr  Arg  Ala  Ile  Asp  Ser  Asn  Glu  Glu  Asp  Met  Gly  Pro  Val  Tyr
1020                    1025                    1030                    1035

AAC  AAC  CGA  GTG  GAG  ATG  GCC  ATC  TTC  TTC  ATC  ATC  TAC  ATC  ATC  CTC       3231
Asn  Asn  Arg  Val  Glu  Met  Ala  Ile  Phe  Phe  Ile  Ile  Tyr  Ile  Ile  Leu
                    1040                    1045                    1050

ATT  GCC  TTC  TTC  ATG  ATG  AAC  ATC  TTT  GTG  GGC  TTT  GTC  ATC  GTC  ACC       3279
Ile  Ala  Phe  Phe  Met  Met  Asn  Ile  Phe  Val  Gly  Phe  Val  Ile  Val  Thr
               1055                    1060                    1065

TTC  CAG  GAG  CAG  GGG  GAG  ACG  GAG  TAC  AAG  AAC  TGC  GAG  CTG  GAC  AAG       3327
Phe  Gln  Glu  Gln  Gly  Glu  Thr  Glu  Tyr  Lys  Asn  Cys  Glu  Leu  Asp  Lys
          1070                    1075                    1080

AAC  CAG  CGC  CAG  TGT  GTG  CAG  TAT  GCC  CTG  AAG  GCC  CGC  CCA  CTT  CGG       3375
Asn  Gln  Arg  Gln  Cys  Val  Gln  Tyr  Ala  Leu  Lys  Ala  Arg  Pro  Leu  Arg
     1085                    1090                    1095

TGC  TAC  ATC  CCC  AAG  AAC  CCA  TAC  CAG  TAC  CAG  GTG  TGG  TAC  GTC  GTC       3423
Cys  Tyr  Ile  Pro  Lys  Asn  Pro  Tyr  Gln  Tyr  Gln  Val  Trp  Tyr  Val  Val
1100                    1105                    1110                    1115

ACC  TCC  TCC  TAC  TTT  GAA  TAC  CTG  ATG  TTC  GCC  CTC  ATC  ATG  CTC  AAC       3471
Thr  Ser  Ser  Tyr  Phe  Glu  Tyr  Leu  Met  Phe  Ala  Leu  Ile  Met  Leu  Asn
                    1120                    1125                    1130

ACC  ATC  TGC  CTG  GGC  ATG  CAG  CAC  TAC  CAC  CAG  TCG  GAG  GAG  ATG  AAC       3519
Thr  Ile  Cys  Leu  Gly  Met  Gln  His  Tyr  His  Gln  Ser  Glu  Glu  Met  Asn
               1135                    1140                    1145

CAC  ATC  TCA  GAC  ATC  CTC  AAT  GTG  GCC  TTC  ACC  ATC  ATC  TTC  ACG  CTG       3567
His  Ile  Ser  Asp  Ile  Leu  Asn  Val  Ala  Phe  Thr  Ile  Ile  Phe  Thr  Leu
          1150                    1155                    1160

GAG  ATG  ATT  CTC  AAG  CTC  TTG  GCG  TTC  AAG  GCC  AGG  GGC  TAT  TTC  GGA       3615
Glu  Met  Ile  Leu  Lys  Leu  Leu  Ala  Phe  Lys  Ala  Arg  Gly  Tyr  Phe  Gly
     1165                    1170                    1175

GAC  CCC  TGG  AAT  GTG  TTC  GAC  TTC  CTG  ATC  GTC  ATC  GGC  AGC  ATC  ATT       3663
Asp  Pro  Trp  Asn  Val  Phe  Asp  Phe  Leu  Ile  Val  Ile  Gly  Ser  Ile  Ile
1180                    1185                    1190                    1195

GAC  GTC  ATC  CTC  AGC  GAG  ATC  GAC  ACT  TTC  CTG  GCC  TCC  AGC  GGG  GGA       3711
Asp  Val  Ile  Leu  Ser  Glu  Ile  Asp  Thr  Phe  Leu  Ala  Ser  Ser  Gly  Gly
                    1200                    1205                    1210

CTG  TAT  TGC  CTG  GGT  GGC  GGC  TGC  GGG  AAC  GTT  GAC  CCA  GAC  GAG  AGC       3759
Leu  Tyr  Cys  Leu  Gly  Gly  Gly  Cys  Gly  Asn  Val  Asp  Pro  Asp  Glu  Ser
               1215                    1220                    1225

GCC  CGC  ATC  TCC  AGT  GCC  TTC  TTC  CGC  CTG  TTC  CGG  GTT  ATG  AGG  CTG       3807
Ala  Arg  Ile  Ser  Ser  Ala  Phe  Phe  Arg  Leu  Phe  Arg  Val  Met  Arg  Leu
          1230                    1235                    1240

ATC  AAG  CTG  CTG  AGT  CGG  GCC  GAG  GGC  GTG  CGC  ACG  CTG  CTG  TGG  ACG       3855
Ile  Lys  Leu  Leu  Ser  Arg  Ala  Glu  Gly  Val  Arg  Thr  Leu  Leu  Trp  Thr
     1245                    1250                    1255

TTC  ATC  AAG  TCC  TTC  CAG  GCC  CTG  CCC  TAC  GTG  GCC  CTG  CTC  ATC  GTC       3903
Phe  Ile  Lys  Ser  Phe  Gln  Ala  Leu  Pro  Tyr  Val  Ala  Leu  Leu  Ile  Val
1260                    1265                    1270                    1275

ATG  CTG  TTC  TTC  ATC  TAC  GCC  GTC  ATC  GGC  ATG  CAG  ATG  TTT  GGA  AAG       3951
Met  Leu  Phe  Phe  Ile  Tyr  Ala  Val  Ile  Gly  Met  Gln  Met  Phe  Gly  Lys
```

|  |  |
|---|---|
| ATC GCC CTG GTG GAC GGG ACC CAG ATC AAC CGC AAC AAC AAC TTC CAG<br>Ile Ala Leu Val Asp Gly Thr Gln Ile Asn Arg Asn Asn Asn Phe Gln<br>1295                       1300                  1305 | 3999 |
| ACC TTC CCG CAG GCC GTG CTG CTG CTC TTC AGG TGT GCG ACA GGG GAG<br>Thr Phe Pro Gln Ala Val Leu Leu Leu Phe Arg Cys Ala Thr Gly Glu<br>1310                     1315                    1320 | 4047 |
| GCG TGG CAA GAG ATC CTG CTG GCC TGC AGC TAC GGG AAG TTG TGC GAC<br>Ala Trp Gln Glu Ile Leu Leu Ala Cys Ser Tyr Gly Lys Leu Cys Asp<br>1325                     1330                  1335 | 4095 |
| CCA GAG TCA GAC TAC GCC CCG GGC GAG GAG TAC ACG TGT GGC ACC AAC<br>Pro Glu Ser Asp Tyr Ala Pro Gly Glu Glu Tyr Thr Cys Gly Thr Asn<br>1340                   1345                   1350                1355 | 4143 |
| TTC GCC TAC TAC TAC TTC ATC AGC TTC TAC ATG CTC TGC GCC TTC CTG<br>Phe Ala Tyr Tyr Tyr Phe Ile Ser Phe Tyr Met Leu Cys Ala Phe Leu<br>1360                     1365                    1370 | 4191 |
| ATC ATC AAC CTC TTC GTG GCT GTC ATC ATG GAC AAC TTT GAC TAC CTG<br>Ile Ile Asn Leu Phe Val Ala Val Ile Met Asp Asn Phe Asp Tyr Leu<br>1375                     1380                  1385 | 4239 |
| ACA CGC GAC TGG TCC ATC CTG GGC CCT CAC CAC CTG GAC GAG TTC AAG<br>Thr Arg Asp Trp Ser Ile Leu Gly Pro His His Leu Asp Glu Phe Lys<br>1390                   1395                    1400 | 4287 |
| GCC ATC TGG GCA GAG TAT GAC CCA GAG GCC AAG GGG CGA ATC AAG CAC<br>Ala Ile Trp Ala Glu Tyr Asp Pro Glu Ala Lys Gly Arg Ile Lys His<br>1405                     1410                  1415 | 4335 |
| CTG GAC GTG GTG ACC CTG CTG AGA AGG ATC CAG CCC CCT CTG GGC TTC<br>Leu Asp Val Val Thr Leu Leu Arg Arg Ile Gln Pro Pro Leu Gly Phe<br>1420                     1425                    1430                1435 | 4383 |
| GGG AAG TTC TGT CCA CAC CGG GTG GCC TGT AAG CGC CTG GTG GGC ATG<br>Gly Lys Phe Cys Pro His Arg Val Ala Cys Lys Arg Leu Val Gly Met<br>1440                     1445                    1450 | 4431 |
| AAC ATG CCC CTG AAC AGT GAC GGC ACG GTC ACC TTC AAT GCC ACG CTC<br>Asn Met Pro Leu Asn Ser Asp Gly Thr Val Thr Phe Asn Ala Thr Leu<br>1455                     1460                  1465 | 4479 |
| TTT GCC CTG GTG CGC ACG GCC CTC AAG ATC AAG ACA GAA GGT AAC TTC<br>Phe Ala Leu Val Arg Thr Ala Leu Lys Ile Lys Thr Glu Gly Asn Phe<br>1470                     1475                    1480 | 4527 |
| GAG CAG GCC AAC GAG GAG CTG AGG GCC ATC ATC AAG AAG ATC TGG AAG<br>Glu Gln Ala Asn Glu Glu Leu Arg Ala Ile Ile Lys Lys Ile Trp Lys<br>1485                     1490                  1495 | 4575 |
| AGA ACC AGC ATG AAG CTA CTG GAC CAG GTC ATC CCT CCC ATA GGA GAT<br>Arg Thr Ser Met Lys Leu Leu Asp Gln Val Ile Pro Pro Ile Gly Asp<br>1500                     1505                    1510                1515 | 4623 |
| GAC GAG GTG ACC GTG GGG AAG TTC TAC GCC ACA TTC CTC ATC CAG GAG<br>Asp Glu Val Thr Val Gly Lys Phe Tyr Ala Thr Phe Leu Ile Gln Glu<br>1520                     1525                    1530 | 4671 |
| CAC TTC CGG AAG TTC ATG AAG CGC CAG GAG GAA TAT TAT GGG TAT CGG<br>His Phe Arg Lys Phe Met Lys Arg Gln Glu Glu Tyr Tyr Gly Tyr Arg<br>1535                     1540                    1545 | 4719 |
| CCC AAG AAG GAC ACC GTG CAG ATC CAG GCT GGG CTG CGG ACC ATA GAG<br>Pro Lys Lys Asp Thr Val Gln Ile Gln Ala Gly Leu Arg Thr Ile Glu<br>1550                     1555                    1560 | 4767 |
| GAG GAG GCG GCC CCT GAG ATC CGC CGC ACC ATC TCA GGA GAC CTG ACC<br>Glu Glu Ala Ala Pro Glu Ile Arg Arg Thr Ile Ser Gly Asp Leu Thr<br>1565                     1570                  1575 | 4815 |
| GCC GAG GAG GAG CTG GAG AGA GCC ATG GTG GAG GCT GCG ATG GAG GAG<br>Ala Glu Glu Glu Leu Glu Arg Ala Met Val Glu Ala Ala Met Glu Glu<br>1580                     1585                    1590                1595 | 4863 |
| AGG ATC TTC CGG AGG ACC GGA GGC CTG TTT GGC CAG GTG GAC ACC TTC<br>Arg Ile Phe Arg Arg Thr Gly Gly Leu Phe Gly Gln Val Asp Thr Phe | 4911 |

```
                1600                      1605                     1610
CTG  GAA  AGG  ACC  AAC  TCC  CTA  CCC  CCG  GTG  ATG  GCC  AAC  CAA  AGA  CCG      4959
Leu  Glu  Arg  Thr  Asn  Ser  Leu  Pro  Pro  Val  Met  Ala  Asn  Gln  Arg  Pro
               1615                     1620                     1625

CTC  CAG  TTT  GCT  GAG  ATA  GAA  ATG  GAA  GAG  CTT  GAG  TCG  CCT  GTC  TTC      5007
Leu  Gln  Phe  Ala  Glu  Ile  Glu  Met  Glu  Glu  Leu  Glu  Ser  Pro  Val  Phe
          1630                     1635                     1640

TTG  GAG  GAC  TTC  CCT  CAA  GAC  GCA  AGA  ACC  AAC  CCT  CTC  GCT  CGT  GCC      5055
Leu  Glu  Asp  Phe  Pro  Gln  Asp  Ala  Arg  Thr  Asn  Pro  Leu  Ala  Arg  Ala
     1645                     1650                     1655

AAT  ACC  AAC  AAC  GCC  AAT  GCC  AAT  GTT  GCC  TAT  GGC  AAC  AGC  AAC  CAT      5103
Asn  Thr  Asn  Asn  Ala  Asn  Ala  Asn  Val  Ala  Tyr  Gly  Asn  Ser  Asn  His
1660                     1665                     1670                     1675

AGC  AAC  AAC  CAG  ATG  TTT  TCC  AGC  GTC  CAC  TGT  GAA  AGG  GAG  TTC  CCG      5151
Ser  Asn  Asn  Gln  Met  Phe  Ser  Ser  Val  His  Cys  Glu  Arg  Glu  Phe  Pro
                    1680                    1685                     1690

GGA  GAG  GCG  GAG  ACA  CCG  GCT  GCC  GGA  CGA  GGA  GCC  CTC  AGC  CAC  TCC      5199
Gly  Glu  Ala  Glu  Thr  Pro  Ala  Ala  Gly  Arg  Gly  Ala  Leu  Ser  His  Ser
               1695                     1700                     1705

CAC  AGG  GCC  CTG  GGA  CCT  CAC  AGC  AAG  CCC  TGT  GCT  GGA  AAA  CTG  AAT      5247
His  Arg  Ala  Leu  Gly  Pro  His  Ser  Lys  Pro  Cys  Ala  Gly  Lys  Leu  Asn
          1710                     1715                     1720

GGG  CAG  CTG  GTC  CAG  CCG  GGA  ATG  CCC  ATC  AAC  CAG  GCA  CCT  CCT  GCC      5295
Gly  Gln  Leu  Val  Gln  Pro  Gly  Met  Pro  Ile  Asn  Gln  Ala  Pro  Pro  Ala
     1725                     1730                     1735

CCC  TGC  CAG  CAG  CCT  AGC  ACA  GAT  CCC  CCA  GAG  CGC  GGG  CAG  AGG  AGG      5343
Pro  Cys  Gln  Gln  Pro  Ser  Thr  Asp  Pro  Pro  Glu  Arg  Gly  Gln  Arg  Arg
1740                     1745                     1750                     1755

ACC  TCC  CTG  ACA  GGG  TCT  CTG  CAA  GAC  GAA  GCA  CCC  CAG  AGG  AGG  AGC      5391
Thr  Ser  Leu  Thr  Gly  Ser  Leu  Gln  Asp  Glu  Ala  Pro  Gln  Arg  Arg  Ser
                    1760                     1765                     1770

TCC  GAG  GGG  AGC  ACC  CCC  AGG  CGC  CCG  GCT  CCT  GCT  ACA  GCT  CTG  CTG      5439
Ser  Glu  Gly  Ser  Thr  Pro  Arg  Arg  Pro  Ala  Pro  Ala  Thr  Ala  Leu  Leu
               1775                     1780                     1785

ATC  CAA  GAG  GCT  CTG  GTT  CGA  GGG  GGC  CTG  GAC  ACC  TTG  GCA  GCT  GAT      5487
Ile  Gln  Glu  Ala  Leu  Val  Arg  Gly  Gly  Leu  Asp  Thr  Leu  Ala  Ala  Asp
          1790                     1795                     1800

GCT  GGC  TTC  GTC  ATG  GCA  ACA  AGC  CAG  GCC  CTG  GTA  GAC  GCC  TGT  CAG      5535
Ala  Gly  Phe  Val  Met  Ala  Thr  Ser  Gln  Ala  Leu  Val  Asp  Ala  Cys  Gln
     1805                     1810                     1815

ATG  GAA  CCG  GAG  GAA  GTA  GAG  GTC  GCA  GCC  ACA  GAG  CTA  CTG  AAA  GAG      5583
Met  Glu  Pro  Glu  Glu  Val  Glu  Val  Ala  Ala  Thr  Glu  Leu  Leu  Lys  Glu
1820                     1825                     1830                     1835

CGA  GAG  TCC  GTC  CAG  GGC  ATG  GCC  AGT  GTC  CCG  GGA  AGC  CTG  AGC  CGC      5631
Arg  Glu  Ser  Val  Gln  Gly  Met  Ala  Ser  Val  Pro  Gly  Ser  Leu  Ser  Arg
                    1840                     1845                     1850

AGG  TCC  TCC  CTG  GGC  AGC  CTT  GAC  CAG  GTC  CAG  GGC  TCC  CAG  GAA  ACC      5679
Arg  Ser  Ser  Leu  Gly  Ser  Leu  Asp  Gln  Val  Gln  Gly  Ser  Gln  Glu  Thr
               1855                     1860                     1865

CTT  ATT  CCT  CCC  AGG  CCG  TGA  TGGCTGTGCA  GTGTCCACAT  GACCAAGGCG  AGGGG         5735
Leu  Ile  Pro  Pro  Arg  Pro  *
          1870

GACAGTGCGT  GCAGAAGCTC  AGCCCTGCAT  GGCAGCCTCC  CTCTGTCTCA  GCCCTCCTGC              5795

TGAGCTGGGG  CGGTCTGGAA  CCGACCAGGA  AGCCAGGAGC  CTCCCTGGC   CAGCAAGAGG              5855

CATGATTCTA  AAGCATCCAG  AAAGGCCTGG  TCAGTGCCAC  TCCCCAGCAG  GACATTAAAG              5915

TCTCTAGGTC  TGTGGCAAAA  AAAAAAAAA   AAAAAAAAAA  AAAAAAAAAA  AAAAAAAAAA              5975
```

( 2 ) INFORMATION FOR SEQ ID NO:2:

( i ) SEQUENCE CHARACTERISTICS:
   ( A ) LENGTH: 3802 base pairs
   ( B ) TYPE: nucleic acid
   ( C ) STRANDEDNESS: single
   ( D ) TOPOLOGY: linear ( i i ) MOLECULE TYPE: cDNA ( i x ) FEATURE:
   ( A ) NAME/KEY: Coding Sequence
   ( B ) LOCATION: 309...3630
   ( A ) NAME/KEY: mat_peptide
   ( B ) LOCATION: 387...3626
   ( D ) OTHER INFORMATION:

( x i ) SEQUENCE DESCRIPTION: SEQ ID NO:2:

```
AGAAGGGAGG GCGAGCGTGG TGTGTGCGCG CTCGGGCGCC GGCGGCACCG CCGAGGTCTG        60

TTGGCAAAAG TCGCCCTTGA TGGCGGCGGA GGCGAGGCAG CCGCGGCGCC GAACAGCCGA       120

CGCGCGCTAG CGGGGTCCGC CCGCCCCTTT CCCAGAGCCC AGCGCCGCCG TTCGCCGCCG       180

CCGCCGCCCG CCCGCGCGCC GTTCGCCGCC GCCGCCGCCC GCGGGTGGCA GCGCCGCTCG       240

GTCCCCGGCC CCGGGGCCGG CTGGGGGGCG GTCGGGGCGT GTGAGGGGCT TGCTCCCAGC       300

TCGCGAAG ATG GCT GCG GGC CGC CCG CTG GCC TGG ACG CTG ACA CTT TGG       350
         Met Ala Ala Gly Arg Pro Leu Ala Trp Thr Leu Thr Leu Trp
         -26 -25                -20                    -15

CAG GCG TGG CTG ATC CTG ATC GGG CCC TCG TCG GAG GAG CCG TTC CCT       398
Gln Ala Trp Leu Ile Leu Ile Gly Pro Ser Ser Glu Glu Pro Phe Pro
        -10              -5               -1  1

TCA GCC GTC ACT ATC AAG TCA TGG GTG GAT AAG ATG CAA GAA GAC CTG       446
Ser Ala Val Thr Ile Lys Ser Trp Val Asp Lys Met Gln Glu Asp Leu
 5                   10                  15                  20

GTC ACA CTG GCA AAA ACA GCA AGT GGA GTC AAT CAG CTT GTT GAT ATT       494
Val Thr Leu Ala Lys Thr Ala Ser Gly Val Asn Gln Leu Val Asp Ile
                 25                  30                  35

TAT GAG AAA TAT CAA GAT TTG TAT ACT GTG GAA CCA AAT AAT GCA CGT       542
Tyr Glu Lys Tyr Gln Asp Leu Tyr Thr Val Glu Pro Asn Asn Ala Arg
             40                  45                  50

CAG CTG GTG GAA ATT GCA GCC AGA GAC ATT GAG AAG CTT CTC AGC AAC       590
Gln Leu Val Glu Ile Ala Ala Arg Asp Ile Glu Lys Leu Leu Ser Asn
         55                  60                  65

AGA TCT AAA GCC CTG GTG CGC CTG GCT TTG GAA GCA GAG AAA GTT CAA       638
Arg Ser Lys Ala Leu Val Arg Leu Ala Leu Glu Ala Glu Lys Val Gln
     70                  75                  80

GCA GCC CAC CAA TGG AGG GAA GAT TTT GCA AGC AAT GAA GTT GTC TAC       686
Ala Ala His Gln Trp Arg Glu Asp Phe Ala Ser Asn Glu Val Val Tyr
 85                  90                  95                 100

TAT AAC GCG AAG GAT GAT CTT GAT CCT GAA AAA AAT GAC AGT GAA CCA       734
Tyr Asn Ala Lys Asp Asp Leu Asp Pro Glu Lys Asn Asp Ser Glu Pro
                105                 110                 115

GGC AGC CAG AGG ATC AAA CCT GTT TTC ATT GAC GAT GCT AAC TTT AGA       782
Gly Ser Gln Arg Ile Lys Pro Val Phe Ile Asp Asp Ala Asn Phe Arg
            120                 125                 130

AGA CAA GTA TCC TAT CAG CAC GCA GCT GTC CAT ATC CCC ACT GAC ATC       830
Arg Gln Val Ser Tyr Gln His Ala Ala Val His Ile Pro Thr Asp Ile
        135                 140                 145

TAT GAA GGA TCG ACA ATC GTG TTA AAC GAA CTC AAC TGG ACA AGT GCC       878
Tyr Glu Gly Ser Thr Ile Val Leu Asn Glu Leu Asn Trp Thr Ser Ala
    150                 155                 160

TTA GAT GAC GTT TTC AAA AAA AAT CGA GAA GAA GAC CCT TCA CTG TTG       926
Leu Asp Asp Val Phe Lys Lys Asn Arg Glu Glu Asp Pro Ser Leu Leu
165                 170                 175                 180
```

```
TGG CAG GTG TTT GGC AGT GCC ACT GGC CTG GCC CGG TAT TAC CCA GCT         974
Trp Gln Val Phe Gly Ser Ala Thr Gly Leu Ala Arg Tyr Tyr Pro Ala
                185                 190                 195

TCT CCA TGG GTT GAT AAT AGC CGA ACC CCA AAC AAG ATT GAT CTT TAT        1022
Ser Pro Trp Val Asp Asn Ser Arg Thr Pro Asn Lys Ile Asp Leu Tyr
                200                 205                 210

GAT GTA CGC AGA AGA CCA TGG TAC ATC CAA GGT GCT GCA TCC CCT AAA        1070
Asp Val Arg Arg Arg Pro Trp Tyr Ile Gln Gly Ala Ala Ser Pro Lys
            215                 220                 225

GAT ATG CTT ATT CTG GTG GAT GTG AGT GGA AGC GTT AGT GGA CTG ACA        1118
Asp Met Leu Ile Leu Val Asp Val Ser Gly Ser Val Ser Gly Leu Thr
        230                 235                 240

CTC AAA CTC ATC CGG ACA TCC GTC TCC GAA ATG TTG GAA ACC CTC TCA        1166
Leu Lys Leu Ile Arg Thr Ser Val Ser Glu Met Leu Glu Thr Leu Ser
245                 250                 255                 260

GAT GAT GAT TTT GTG AAC GTG GCT TCA TTT AAC AGC AAT GCT CAG GAT        1214
Asp Asp Asp Phe Val Asn Val Ala Ser Phe Asn Ser Asn Ala Gln Asp
                265                 270                 275

GTA AGC TGC TTT CAG CAC CTT GTC CAA GCA AAT GTA AGA AAT AAG AAA        1262
Val Ser Cys Phe Gln His Leu Val Gln Ala Asn Val Arg Asn Lys Lys
                280                 285                 290

GTG TTG AAA GAT GCA GTG AAT AAT ATC ACA GCA AAA GGA ATC ACA GAT        1310
Val Leu Lys Asp Ala Val Asn Asn Ile Thr Ala Lys Gly Ile Thr Asp
            295                 300                 305

TAT AAG AAG GGC TTT AGT TTT GCT TTT GAG CAG CTG CTT AAT TAT AAT        1358
Tyr Lys Lys Gly Phe Ser Phe Ala Phe Glu Gln Leu Leu Asn Tyr Asn
        310                 315                 320

GTA TCC AGA GCC AAC TGC AAT AAG ATT ATC ATG TTG TTC ACG GAC GGA        1406
Val Ser Arg Ala Asn Cys Asn Lys Ile Ile Met Leu Phe Thr Asp Gly
325                 330                 335                 340

GGA GAA GAG AGA GCC CAG GAG ATA TTT GCC AAA TAC AAT AAA GAC AAG        1454
Gly Glu Glu Arg Ala Gln Glu Ile Phe Ala Lys Tyr Asn Lys Asp Lys
                345                 350                 355

AAA GTA CGT GTA TTC ACA TTC TCA GTT GGC CAA CAT AAT TAC GAC AGA        1502
Lys Val Arg Val Phe Thr Phe Ser Val Gly Gln His Asn Tyr Asp Arg
                360                 365                 370

GGA CCT ATT CAG TGG ATG GCT TGC GAA AAT AAA GGT TAT TAT TAT GAA        1550
Gly Pro Ile Gln Trp Met Ala Cys Glu Asn Lys Gly Tyr Tyr Tyr Glu
            375                 380                 385

ATT CCA TCC ATT GGA GCC ATA AGA ATT AAT ACT CAG GAA TAC CTA GAT        1598
Ile Pro Ser Ile Gly Ala Ile Arg Ile Asn Thr Gln Glu Tyr Leu Asp
        390                 395                 400

GTT CTG GGA AGA CCG ATG GTT TTA GCA GGA GAC AAA GCT AAG CAA GTC        1646
Val Leu Gly Arg Pro Met Val Leu Ala Gly Asp Lys Ala Lys Gln Val
405                 410                 415                 420

CAA TGG ACA AAT GTG TAC CTG GAT GCA CTG GAA CTG GGA CTT GTC ATT        1694
Gln Trp Thr Asn Val Tyr Leu Asp Ala Leu Glu Leu Gly Leu Val Ile
                425                 430                 435

ACT GGA ACT CTT CCG GTC TTC AAC ATA ACT GGC CAA TTT GAA AAT AAG        1742
Thr Gly Thr Leu Pro Val Phe Asn Ile Thr Gly Gln Phe Glu Asn Lys
                440                 445                 450

ACA AAC TTA AAG AAC CAG CTG ATT CTT GGA GTG ATG GGA GTT GAT GTG        1790
Thr Asn Leu Lys Asn Gln Leu Ile Leu Gly Val Met Gly Val Asp Val
            455                 460                 465

TCT TTG GAA GAT ATT AAA AGA CTG ACA CCA CGT TTT ACA CTC TGC CCC        1838
Ser Leu Glu Asp Ile Lys Arg Leu Thr Pro Arg Phe Thr Leu Cys Pro
        470                 475                 480

AAT GGC TAC TAT TTT GCA ATT GAT CCT AAT GGT TAT GTG TTA TTA CAT        1886
Asn Gly Tyr Tyr Phe Ala Ile Asp Pro Asn Gly Tyr Val Leu Leu His
485                 490                 495                 500
```

| | | | | | | | | | | | | | | | | |
|---|---|---|---|---|---|---|---|---|---|---|---|---|---|---|---|---|
| CCA | AAT | CTT | CAG | CCA | AAG | CCT | ATT | GGT | GTA | GGT | ATA | CCA | ACA | ATT | AAT | 1934 |
| Pro | Asn | Leu | Gln 505 | Pro | Lys | Pro | Ile | Gly | Val 510 | Gly | Ile | Pro | Thr | Ile 515 | Asn | |
| TTG | AGA | AAA | AGG | AGA | CCC | AAT | GTT | CAG | AAC | CCC | AAA | TCT | CAG | GAG | CCA | 1982 |
| Leu | Arg | Lys 520 | Arg | Arg | Pro | Asn | Val | Gln 525 | Asn | Pro | Lys | Ser | Gln 530 | Glu | Pro | |
| GTG | ACA | TTG | GAT | TTC | CTC | GAT | GCA | GAG | TTG | GAG | AAT | GAC | ATT | AAA | GTG | 2030 |
| Val | Thr | Leu 535 | Asp | Phe | Leu | Asp | Ala 540 | Glu | Leu | Glu | Asn | Asp 545 | Ile | Lys | Val | |
| GAG | ATT | CGA | AAT | AAA | ATG | ATC | GAT | GGA | GAA | AGT | GGA | GAA | AAA | ACA | TTC | 2078 |
| Glu | Ile | Arg 550 | Asn | Lys | Met | Ile 555 | Asp | Gly | Glu | Ser | Gly 560 | Glu | Lys | Thr | Phe | |
| AGA | ACT | CTG | GTT | AAA | TCT | CAA | GAT | GAG | AGA | TAT | ATT | GAC | AAA | GGA | AAC | 2126 |
| Arg 565 | Thr | Leu | Val | Lys | Ser 570 | Gln | Asp | Glu | Arg | Tyr 575 | Ile | Asp | Lys | Gly | Asn 580 | |
| AGG | ACA | TAC | ACG | TGG | ACT | CCT | GTC | AAC | GGC | ACA | GAT | TAT | AGC | AGT | TTG | 2174 |
| Arg | Thr | Tyr | Thr | Trp 585 | Thr | Pro | Val | Asn | Gly 590 | Thr | Asp | Tyr | Ser | Ser 595 | Leu | |
| GCC | TTG | GTA | TTA | CCA | ACC | TAC | AGT | TTT | TAC | TAT | ATA | AAA | GCC | AAA | ATA | 2222 |
| Ala | Leu | Val | Leu 600 | Pro | Thr | Tyr | Ser | Phe 605 | Tyr | Tyr | Ile | Lys | Ala 610 | Lys | Ile | |
| GAA | GAG | ACA | ATA | ACT | CAG | GCC | AGA | TAT | TCA | GAA | ACA | CTG | AAA | CCG | GAT | 2270 |
| Glu | Glu | Thr 615 | Ile | Thr | Gln | Ala | Arg 620 | Tyr | Ser | Glu | Thr | Leu 625 | Lys | Pro | Asp | |
| AAT | TTT | GAA | GAA | TCT | GGC | TAC | ACA | TTC | CTA | GCA | CCA | AGA | GAT | TAC | TGC | 2318 |
| Asn | Phe 630 | Glu | Glu | Ser | Gly | Tyr 635 | Thr | Phe | Leu | Ala | Pro 640 | Arg | Asp | Tyr | Cys | |
| AGT | GAC | CTT | AAA | CCT | TCA | GAT | AAT | AAC | ACT | GAA | TTT | CTT | TTA | AAT | TTC | 2366 |
| Ser 645 | Asp | Leu | Lys | Pro | Ser 650 | Asp | Asn | Asn | Thr | Glu 655 | Phe | Leu | Leu | Asn | Phe 660 | |
| AAT | GAG | TTT | ATT | GAT | AGA | AAA | ACT | CCA | AAC | AAC | CCA | TCC | TGT | AAT | ACA | 2414 |
| Asn | Glu | Phe | Ile | Asp 665 | Arg | Lys | Thr | Pro | Asn 670 | Asn | Pro | Ser | Cys | Asn 675 | Thr | |
| GAC | TTG | ATT | AAT | AGA | GTC | TTG | CTG | GAT | GCA | GGC | TTT | ACA | AAT | GAA | CTT | 2462 |
| Asp | Leu | Ile | Asn | Arg 680 | Val | Leu | Leu | Asp | Ala 685 | Gly | Phe | Thr | Asn | Glu 690 | Leu | |
| GTT | CAA | AAT | TAC | TGG | AGT | AAG | CAG | AAG | AAT | ATC | AAG | GGA | GTG | AAA | GCA | 2510 |
| Val | Gln | Asn 695 | Tyr | Trp | Ser | Lys | Gln 700 | Lys | Asn | Ile | Lys | Gly 705 | Val | Lys | Ala | |
| CGG | TTT | GTT | GTG | ACT | GAT | GGT | GGG | ATT | ACC | AGA | GTT | TAT | CCC | AAA | GAG | 2558 |
| Arg | Phe 710 | Val | Val | Thr | Asp | Gly 715 | Gly | Ile | Thr | Arg | Val 720 | Tyr | Pro | Lys | Glu | |
| GCT | GGA | GAA | AAT | TGG | CAG | GAA | AAC | CCA | GAG | ACA | TAT | GAA | GAC | AGC | TTC | 2606 |
| Ala 725 | Gly | Glu | Asn | Trp | Gln 730 | Glu | Asn | Pro | Glu | Thr 735 | Tyr | Glu | Asp | Ser | Phe 740 | |
| TAT | AAA | AGG | AGC | CTC | GAT | AAT | GAT | AAC | TAC | GTT | TTC | ACT | GCT | CCC | TAC | 2654 |
| Tyr | Lys | Arg | Ser | Leu 745 | Asp | Asn | Asp | Asn | Tyr 750 | Val | Phe | Thr | Ala | Pro 755 | Tyr | |
| TTT | AAC | AAA | AGT | GGA | CCT | GGG | GCC | TAT | GAG | TCA | GGC | ATT | ATG | GTA | AGC | 2702 |
| Phe | Asn | Lys | Ser 760 | Gly | Pro | Gly | Ala | Tyr 765 | Glu | Ser | Gly | Ile | Met 770 | Val | Ser | |
| AAA | GCT | GTA | GAA | ATA | TAT | ATC | CAA | GGA | AAA | CTT | CTT | AAA | CCT | GCA | GTT | 2750 |
| Lys | Ala | Val 775 | Glu | Ile | Tyr | Ile | Gln 780 | Gly | Lys | Leu | Leu | Lys 785 | Pro | Ala | Val | |
| GTT | GGA | ATT | AAA | ATT | GAT | GTA | AAT | TCT | TGG | ATA | GAG | AAT | TTC | ACC | AAA | 2798 |
| Val | Gly | Ile 790 | Lys | Ile | Asp | Val | Asn 795 | Ser | Trp | Ile | Glu | Asn 800 | Phe | Thr | Lys | |
| ACT | TCA | ATC | AGG | GAT | CCG | TGT | GCT | GGT | CCA | GTT | TGT | GAC | TGC | AAA | CGA | 2846 |
| Thr 805 | Ser | Ile | Arg | Asp | Pro 810 | Cys | Ala | Gly | Pro | Val 815 | Cys | Asp | Cys | Lys | Arg 820 | |

```
AAC AGT GAT GTA ATG GAT TGT GTG ATT CTA GAT GAC GGT GGG TTT CTT       2894
Asn Ser Asp Val Met Asp Cys Val Ile Leu Asp Asp Gly Gly Phe Leu
            825                 830                     835

TTG ATG GCC AAC CAT GAT GAT TAT ACC AAT CAG ATT GGA AGA TTC TTT       2942
Leu Met Ala Asn His Asp Asp Tyr Thr Asn Gln Ile Gly Arg Phe Phe
            840                 845                     850

GGA GAG ATT GAT CCA AGC TTG ATG AGA CAC CTG GTC AAT ATA TCA GTT       2990
Gly Glu Ile Asp Pro Ser Leu Met Arg His Leu Val Asn Ile Ser Val
            855                 860                     865

TAT GCC TTT AAC AAA TCT TAT GAT TAT CAG TCG GTG TGT GAA CCT GGT       3038
Tyr Ala Phe Asn Lys Ser Tyr Asp Tyr Gln Ser Val Cys Glu Pro Gly
870                 875                     880

GCT GCG CCA AAG CAG GGA GCA GGG CAC CGC TCG GCT TAT GTG CCA TCA       3086
Ala Ala Pro Lys Gln Gly Ala Gly His Arg Ser Ala Tyr Val Pro Ser
885                 890                     895                 900

ATA GCA GAC ATA CTG CAG ATT GGA TGG TGG GCC ACT GCT GCT GCC TGG       3134
Ile Ala Asp Ile Leu Gln Ile Gly Trp Trp Ala Thr Ala Ala Ala Trp
            905                 910                     915

TCT ATT CTT CAG CAG TTT CTG TTG AGT TTG ACT TTT CCA CGG CTC CTT       3182
Ser Ile Leu Gln Gln Phe Leu Leu Ser Leu Thr Phe Pro Arg Leu Leu
            920                 925                     930

GAG GCA GCT GAT ATG GAG GAT GAC GAC TTC ACT GCC TCC ATG TCA AAG       3230
Glu Ala Ala Asp Met Glu Asp Asp Asp Phe Thr Ala Ser Met Ser Lys
            935                 940                     945

CAG AGC TGC ATC ACT GAG CAA ACC CAG TAT TTC TTC GAT AAT GAC AGC       3278
Gln Ser Cys Ile Thr Glu Gln Thr Gln Tyr Phe Phe Asp Asn Asp Ser
            950                 955                     960

AAA TCG TTC AGT GGG GTA TTA GAC TGT GGG AAT TGT TCC AGA ATC TTT       3326
Lys Ser Phe Ser Gly Val Leu Asp Cys Gly Asn Cys Ser Arg Ile Phe
965                 970                     975                 980

CAT GTA GAA AAG CTC ATG AAC ACC AAT TTA ATA TTC ATA ATG GTA GAG       3374
His Val Glu Lys Leu Met Asn Thr Asn Leu Ile Phe Ile Met Val Glu
            985                 990                     995

AGC AAG GGG ACA TGT CCC TGT GAC ACA CGG CTG CTC ATA CAA GCA GAG       3422
Ser Lys Gly Thr Cys Pro Cys Asp Thr Arg Leu Leu Ile Gln Ala Glu
            1000                1005                    1010

CAA ACT TCT GAT GGA CCA GAT CCT TGT GAT ATG GTT AAG CAA CCC AGA       3470
Gln Thr Ser Asp Gly Pro Asp Pro Cys Asp Met Val Lys Gln Pro Arg
            1015                1020                    1025

TAT CGA AAA GGG CCA GAT GTC TGC TTT GAC AAC AAT GTC CTG GAG GAT       3518
Tyr Arg Lys Gly Pro Asp Val Cys Phe Asp Asn Asn Val Leu Glu Asp
            1030                1035                    1040

TAT ACT GAC TGC GGT GGG GTC TCT GGA TTA AAT CCT TCC CTG TGG TCC       3566
Tyr Thr Asp Cys Gly Gly Val Ser Gly Leu Asn Pro Ser Leu Trp Ser
1045                1050                    1055                1060

ATC ATC GGG ATA CAG TTT GTA CTG CTT TGG CTG GTT TCT GGC AGC AGA       3614
Ile Ile Gly Ile Gln Phe Val Leu Leu Trp Leu Val Ser Gly Ser Arg
            1065                1070                    1075

CAC TGC CTG TTA TGA C CTTCTAAAAC CAAATCTCCA TAATTAAACT CCAGACCCTG     3670
His Cys Leu Leu *
            1080

CCACAACATG ATCCCTCCGT TATGTTAAAG TAGGGTCAAC TGTTAAATCA GAACATTAGC     3730

TGGGCCTCTG CCATGGCAGA GCCCTAAGGC GCAGACTCAT CAGGCACCCA CTGGCTGCAT     3790

GTCAGGGTGT CC                                                         3802
```

( 2 ) INFORMATION FOR SEQ ID NO:3:

( i ) SEQUENCE CHARACTERISTICS:
        ( A ) LENGTH: 1560 base pairs
        ( B ) TYPE: nucleic acid 5,618,720

-continued ( C ) STRANDEDNESS: single
( D ) TOPOLOGY: unknown ( i i ) MOLECULE TYPE: Genomic DNA ( i x ) FEATURE:
( A ) NAME/KEY: Coding Sequence
( B ) LOCATION: 35...1558

( x i ) SEQUENCE DESCRIPTION: SEQ ID NO:3:

| GGGCGGGGGA GGGGGATTGA TCTTCGATCG CAAG | ATG | GCT | GCT | GGC | TGC | CTG | CTG | 55 |
| | Met | Ala | Ala | Gly | Cys | Leu | Leu | |
| | 1 | | | | 5 | | | |

| GCC | TTG | ACT | CTG | ACA | CTT | TTC | CAA | TCT | TTG | CTC | ATC | GGC | CCC | TCG | TCG | 103 |
| Ala | Leu | Thr | Leu | Thr | Leu | Phe | Gln | Ser | Leu | Leu | Ile | Gly | Pro | Ser | Ser | |
| | | | 10 | | | | 15 | | | | | 20 | | | | |

| GAG | GAG | CCG | TTC | CCT | TCG | GCC | GTC | ACT | ATC | AAA | TCA | TGG | GTG | GAT | AAG | 151 |
| Glu | Glu | Pro | Phe | Pro | Ser | Ala | Val | Thr | Ile | Lys | Ser | Trp | Val | Asp | Lys | |
| | 25 | | | | | 30 | | | | | 35 | | | | | |

| ATG | CAA | GAA | GAC | CTT | GTC | ACA | CTG | GCA | AAA | ACA | GCA | AGT | GGA | GTC | AAT | 199 |
| Met | Gln | Glu | Asp | Leu | Val | Thr | Leu | Ala | Lys | Thr | Ala | Ser | Gly | Val | Asn | |
| 40 | | | | | 45 | | | | | 50 | | | | | 55 | |

| CAG | CTT | GTT | GAT | ATT | TAT | GAG | AAA | TAT | CAA | GAT | TTG | TAT | ACT | GTG | GAA | 247 |
| Gln | Leu | Val | Asp | Ile | Tyr | Glu | Lys | Tyr | Gln | Asp | Leu | Tyr | Thr | Val | Glu | |
| | | | | 60 | | | | | 65 | | | | | 70 | | |

| CCA | AAT | AAT | GCA | CGC | CAG | CTG | GTA | GAA | ATT | GCA | GCC | AGG | GAT | ATT | GAG | 295 |
| Pro | Asn | Asn | Ala | Arg | Gln | Leu | Val | Glu | Ile | Ala | Ala | Arg | Asp | Ile | Glu | |
| | | | 75 | | | | | 80 | | | | | 85 | | | |

| AAA | CTT | CTG | AGC | AAC | AGA | TCT | AAA | GCC | CTG | GTG | AGC | CTG | GCA | TTG | GAA | 343 |
| Lys | Leu | Leu | Ser | Asn | Arg | Ser | Lys | Ala | Leu | Val | Ser | Leu | Ala | Leu | Glu | |
| | | 90 | | | | | 95 | | | | | 100 | | | | |

| GCG | GAG | AAA | GTT | CAA | GCA | GCT | CAC | CAG | TGG | AGA | GAA | GAT | TTT | GCA | AGC | 391 |
| Ala | Glu | Lys | Val | Gln | Ala | Ala | His | Gln | Trp | Arg | Glu | Asp | Phe | Ala | Ser | |
| | 105 | | | | | 110 | | | | | 115 | | | | | |

| AAT | GAA | GTT | GTC | TAC | TAC | AAT | GCA | AAG | GAT | GAT | CTC | GAT | CCT | GAG | AAA | 439 |
| Asn | Glu | Val | Val | Tyr | Tyr | Asn | Ala | Lys | Asp | Asp | Leu | Asp | Pro | Glu | Lys | |
| 120 | | | | | 125 | | | | | 130 | | | | | 135 | |

| AAT | GAC | AGT | GAG | CCA | GGC | AGC | CAG | AGG | ATA | AAA | CCT | GTT | TTC | ATT | GAA | 487 |
| Asn | Asp | Ser | Glu | Pro | Gly | Ser | Gln | Arg | Ile | Lys | Pro | Val | Phe | Ile | Glu | |
| | | | | 140 | | | | | 145 | | | | | 150 | | |

| GAT | GCT | AAT | TTT | GGA | CGA | CAA | ATA | TCT | TAT | CAG | CAC | GCA | GCA | GTC | CAT | 535 |
| Asp | Ala | Asn | Phe | Gly | Arg | Gln | Ile | Ser | Tyr | Gln | His | Ala | Ala | Val | His | |
| | | | 155 | | | | | 160 | | | | | 165 | | | |

| ATT | CCT | ACT | GAC | ATC | TAT | GAG | GGC | TCA | ACA | ATT | GTG | TTA | AAT | GAA | CTC | 583 |
| Ile | Pro | Thr | Asp | Ile | Tyr | Glu | Gly | Ser | Thr | Ile | Val | Leu | Asn | Glu | Leu | |
| | | 170 | | | | | 175 | | | | | 180 | | | | |

| AAC | TGG | ACA | AGT | GCC | TTA | GAT | GAA | GTT | TTC | AAA | AAG | AAT | CGC | GAG | GAA | 631 |
| Asn | Trp | Thr | Ser | Ala | Leu | Asp | Glu | Val | Phe | Lys | Lys | Asn | Arg | Glu | Glu | |
| | 185 | | | | | 190 | | | | | 195 | | | | | |

| GAC | CCT | TCA | TTA | TTG | TGG | CAG | GTT | TTT | GGC | AGT | GCC | ACT | GGC | CTA | GCT | 679 |
| Asp | Pro | Ser | Leu | Leu | Trp | Gln | Val | Phe | Gly | Ser | Ala | Thr | Gly | Leu | Ala | |
| 200 | | | | | 205 | | | | | 210 | | | | | 215 | |

| CGA | TAT | TAT | CCA | GCT | TCA | CCA | TGG | GTT | GAT | AAT | GGT | AGA | ACT | CCA | AAT | 727 |
| Arg | Tyr | Tyr | Pro | Ala | Ser | Pro | Trp | Val | Asp | Asn | Gly | Arg | Thr | Pro | Asn | |
| | | | 220 | | | | | 225 | | | | | 230 | | | |

| ATG | ATT | GAC | CTT | TAT | GAT | GTA | CGC | AGA | AGA | CCA | TGG | TAC | ATC | CAA | GGA | 775 |
| Met | Ile | Asp | Leu | Tyr | Asp | Val | Arg | Arg | Arg | Pro | Trp | Tyr | Ile | Gln | Gly | |
| | | | 235 | | | | | 240 | | | | | 245 | | | |

| GCT | GCA | TCT | CCT | AAA | GAC | ATG | CTT | ATT | CTG | GTG | GAT | GTG | AGT | GGA | AGT | 823 |
| Ala | Ala | Ser | Pro | Lys | Asp | Met | Leu | Ile | Leu | Val | Asp | Val | Ser | Gly | Ser | |
| | | 250 | | | | | 255 | | | | | 260 | | | | |

| GTT | AGT | GGA | TTG | ACA | CTT | AAA | CTG | ATC | CGA | ACA | TCT | GTC | TCC | GAA | ATG | 871 |

| | | | | | | | | | | | | | | | | |
|---|---|---|---|---|---|---|---|---|---|---|---|---|---|---|---|---|
| Val | Ser 265 | Gly | Leu | Thr | Leu | Lys 270 | Leu | Ile | Arg | Thr | Ser 275 | Val | Ser | Glu | Met | |
| TTA | GAA | ACC | CTC | TCA | GAT | GAT | GAT | TTC | GTG | AAT | GTA | GCT | TCA | TTT | AAC | 919 |
| Leu 280 | Glu | Thr | Leu | Ser | Asp 285 | Asp | Asp | Phe | Val | Asn 290 | Val | Ala | Ser | Phe | Asn 295 | |
| AGC | AAT | GCT | CAG | GAT | GTA | AGC | TGT | TTT | CAG | CAC | CTT | GTC | CAA | GCA | AAT | 967 |
| Ser | Asn | Ala | Gln | Asp 300 | Val | Ser | Cys | Phe | Gln 305 | His | Leu | Val | Gln | Ala 310 | Asn | |
| GTA | AGA | AAT | AAA | AAA | GTG | TTG | AAA | GAC | GCG | GTG | AAT | AAT | ATC | ACA | GCC | 1015 |
| Val | Arg | Asn | Lys 315 | Lys | Val | Leu | Lys | Asp 320 | Ala | Val | Asn | Asn | Ile 325 | Thr | Ala | |
| AAA | GGA | ATT | ACA | GAT | TAT | AAG | AAG | GGC | TTT | AGT | TTT | GCT | TTT | GAA | CAG | 1063 |
| Lys | Gly | Ile 330 | Thr | Asp | Tyr | Lys 335 | Lys | Gly | Phe | Ser | Phe 340 | Ala | Phe | Glu | Gln | |
| CTG | CTT | AAT | TAT | AAT | GTT | TCC | AGA | GCA | AAC | TGC | AAT | AAG | ATT | ATT | ATG | 1111 |
| Leu | Leu 345 | Asn | Tyr | Asn | Val | Ser 350 | Arg | Ala | Asn | Cys | Asn 355 | Lys | Ile | Ile | Met | |
| CTA | TTC | ACG | GAT | GGA | GAA | GAG | AGA | GCC | CAG | GAG | ATA | TTT | AAC | AAA | TAC | 1159 |
| Leu 360 | Phe | Thr | Asp | Gly | Glu 365 | Glu | Arg | Ala | Gln | Glu 370 | Ile | Phe | Asn | Lys | Tyr 375 | |
| AAT | AAA | GAT | AAA | AAA | CTA | CCT | GTA | TTC | ACC | TTC | TCA | GTT | GGT | CAA | CAC | 1207 |
| Asn | Lys | Asp | Lys | Lys 380 | Leu | Pro | Val | Phe | Thr 385 | Phe | Ser | Val | Gly | Gln 390 | His | |
| AAT | TAT | GAC | AGA | GGA | CCT | ATT | CAG | TGG | ATG | GCC | TGT | GAA | AAC | AAA | GGT | 1255 |
| Asn | Tyr | Asp | Arg 395 | Gly | Pro | Ile | Gln | Trp 400 | Met | Ala | Cys | Glu | Asn 405 | Lys | Gly | |
| TAT | TAT | TAT | GAA | ATT | CCT | TCC | ATT | GGT | GCA | ATA | AGA | ATC | AAT | ACT | CAG | 1303 |
| Tyr | Tyr | Tyr 410 | Glu | Ile | Pro | Ser | Ile 415 | Gly | Ala | Ile | Arg | Ile 420 | Asn | Thr | Gln | |
| GAA | TAT | TTG | GAT | GTT | TTG | GGA | AGA | CCA | ATG | GTT | TTA | GCA | GGA | GAC | AAA | 1351 |
| Glu | Tyr 425 | Leu | Asp | Val | Leu | Gly 430 | Arg | Pro | Met | Val | Leu 435 | Ala | Gly | Asp | Lys | |
| GCT | AAG | CAA | GTC | CAA | TGG | ACA | AAT | GTG | TAC | CTG | GAT | GCA | TTG | GAA | CTG | 1399 |
| Ala 440 | Lys | Gln | Val | Gln | Trp 445 | Thr | Asn | Val | Tyr | Leu 450 | Asp | Ala | Leu | Glu | Leu 455 | |
| GGA | CTT | GTC | ATT | ACT | GGA | ACT | CTT | CCG | GTC | TTC | AAC | ATA | ACC | GGC | CAA | 1447 |
| Gly | Leu | Val | Ile | Thr 460 | Gly | Thr | Leu | Pro | Val 465 | Phe | Asn | Ile | Thr | Gly 470 | Gln | |
| TTT | GAA | AAT | AAG | ACA | AAC | TTA | AAG | AAC | CAG | CTG | ATT | CTT | GGT | GTG | ATG | 1495 |
| Phe | Glu | Asn | Lys 475 | Thr | Asn | Leu | Lys | Asn 480 | Gln | Leu | Ile | Leu | Gly 485 | Val | Met | |
| GGA | GTA | GAT | GTG | TCT | TTG | GAA | GAT | ATT | AAA | AGA | CTG | ACA | CCA | CGT | TTT | 1543 |
| Gly | Val | Asp 490 | Val | Ser | Leu | Glu | Asp 495 | Ile | Lys | Arg | Leu | Thr 500 | Pro | Arg | Phe | |
| ACA | CTG | TGC | CCC | AAT | GG | | | | | | | | | | | 1560 |
| Thr | Leu 505 | Cys | Pro | Asn | | | | | | | | | | | | |